US009353085B2

(12) United States Patent
Balaganesan et al.

(10) Patent No.: US 9,353,085 B2
(45) Date of Patent: May 31, 2016

(54) COMPOUND FOR ORGANIC ELECTROLUMINESCENT DEVICE AND ORGANIC ELECTROLUMINESCENT DEVICES USING THE SAME

(75) Inventors: Banumathy Balaganesan, Taoyuan (TW); Yi-Huan Fu, Taoyuan (TW); Kun-Feng Chiang, Taoyuan (TW); Fang-Shih Lin, Taipei (TW); Zheng-Feng Ye, Taoyuan (TW); Chang-Ying Chu, Taoyuan (TW)

(73) Assignee: E-RAY OPTOELECTRONICS TECHNOLOGY CO., LTD., Chung-Li (TW)

( * ) Notice: Subject to any disclaimer, the term of this patent is extended or adjusted under 35 U.S.C. 154(b) by 674 days.

(21) Appl. No.: 13/492,036

(22) Filed: Jun. 8, 2012

(65) Prior Publication Data
US 2013/0048956 A1 Feb. 28, 2013

Related U.S. Application Data

(60) Provisional application No. 61/527,683, filed on Aug. 26, 2011.

(51) Int. Cl.
| | | |
|---|---|---|
| H01L 51/54 | (2006.01) | |
| C09K 11/06 | (2006.01) | |
| C07D 401/14 | (2006.01) | |
| C07D 413/14 | (2006.01) | |
| C07D 403/14 | (2006.01) | |
| C07D 409/14 | (2006.01) | |
| C07D 417/14 | (2006.01) | |
| H05B 33/14 | (2006.01) | |
| C07D 235/08 | (2006.01) | |
| C07D 487/16 | (2006.01) | |
| H01L 51/00 | (2006.01) | |
| H01L 51/50 | (2006.01) | |

(52) U.S. Cl.
CPC .......... *C07D 401/14* (2013.01); *C07D 235/08* (2013.01); *C07D 403/14* (2013.01); *C07D 409/14* (2013.01); *C07D 413/14* (2013.01); *C07D 417/14* (2013.01); *C07D 487/16* (2013.01); *C09K 11/06* (2013.01); *H01L 51/0067* (2013.01); *H01L 51/0071* (2013.01); *H01L 51/0072* (2013.01); *H05B 33/14* (2013.01); *C09K 2211/1011* (2013.01); *C09K 2211/1029* (2013.01); *C09K 2211/1044* (2013.01); *C09K 2211/185* (2013.01); *H01L 51/0085* (2013.01); *H01L 51/5072* (2013.01)

(58) Field of Classification Search
None
See application file for complete search history.

(56) References Cited

U.S. PATENT DOCUMENTS

| | | | | |
|---|---|---|---|---|
| 2006/0199943 | A1* | 9/2006 | Falcou et al. | 528/422 |
| 2007/0051944 | A1* | 3/2007 | Vestweber et al. | 257/40 |
| 2010/0060154 | A1* | 3/2010 | Nomura | C07D 263/57 313/504 |
| 2010/0200054 | A1* | 8/2010 | Jung | C09K 11/06 136/256 |
| 2011/0095282 | A1* | 4/2011 | Pflumm et al. | 257/40 |

FOREIGN PATENT DOCUMENTS

| | | | |
|---|---|---|---|
| WO | WO 2010044607 A1 * | 4/2010 | |
| WO | WO 2010072300 A1 * | 7/2010 | |

* cited by examiner

*Primary Examiner* — Andrew K Bohaty
(74) *Attorney, Agent, or Firm* — Amin, Turocy & Watson, LLP

(57) ABSTRACT

The present invention provides a compound of formula (I) for an organic electroluminescent device:

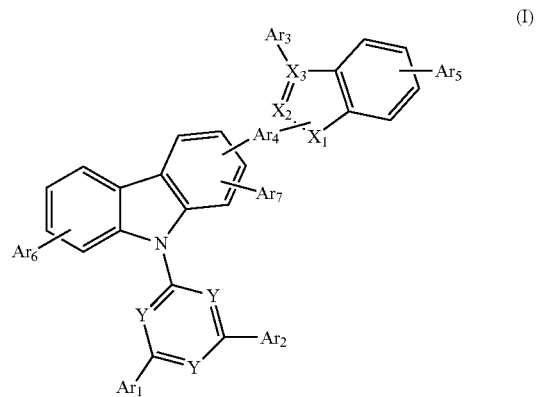

(I)

wherein $X_1$, $X_2$, $X_3$, Y, $Ar_1$, $Ar_2$, $Ar_3$, $Ar_4$, $Ar_5$, $Ar_6$, and $Ar_7$ are as defined in the description.

7 Claims, 13 Drawing Sheets

COMPOUND FOR ORGANIC ELECTROLUMINESCENT DEVICE AND ORGANIC ELECTROLUMINESCENT DEVICES USING THE SAME

BACKGROUND OF THE INVENTION

1. Field of the Invention

The present invention relates to a novel material for electron transportation/injection and emitting layers, and an organic electroluminescence device using the said material, and more particularly to a material for organic electroluminescence (EL) devices providing an electroluminescent device exhibiting a high luminous efficiency, a longer lifetime with reduced driving voltage.

2. Description of Related Art

There has been an increasing interest in developing novel organic materials that cater to organic light emitting device (OLED) applications. Such devices are commercially attractive because they offer the cost-advantageous fabrication of high density pixeled displays exhibiting brilliant luminance with long life times, high efficiency, low driving voltages and wide color range.

A typical OLED comprises at least one organic emissive layer sandwiched between an anode and a cathode. When a current is applied, the anode injects holes and the cathode injects electrons into the organic layer(s). The injected holes and electrons each migrate toward the oppositely charged electrode. When an electron and hole localize on the same molecule, an "exciton", which is a localized electron-hole pair having an excited energy state, is formed. Light is emitted when the exciton relaxes through a photoemissive mechanism. To improve the charge transport capabilities and also the luminous efficiency of such devices, additional layers around the emissive layer, such as an electron transporting layer and/or a hole transporting layer, or an electron blocking and/or hole blocking layer(s) have been incorporated. Doping the host material with another material (guest) has been well demonstrated in literature to enhance the device performance and to tune the chromaticity. Several OLED materials and device configurations are described in U.S. Pat. Nos. 4,769,292, 5,844,363, and 5,707,745, which are incorporated herein by reference in their entirety.

The reason for manufacturing an organic EL display with a multi-layered thin film structure includes stabilization of the interfaces between the electrodes and the organic layers. In addition, in organic materials, the mobility of electrons and holes significantly differ, and thus, if appropriate hole transportation and electron transportation layers are used, holes and electrons can be efficiently transferred to the luminescent layer. Also, if the density of the holes and electrons are balanced in the emitting layer, luminous efficiency can be increased. The proper combination of organic layers described above can enhance the device efficiency and lifetime. However, it has been very difficult to find an organic material that satisfies all the requirements for use in practical display applications.

Tris (8-hydroxyquinoline) aluminum ($Alq_3$) is one of the widely used electron transporting material; however, it has an intense green emission and devices using the same exhibits higher driving voltages. Therefore, it is crucial to find an electron transporting molecule that has excellent properties compared to the conventional material in all practical aspects, such as high efficiency, reduced driving voltage and operational stability.

Organic small molecules having imidazole groups, oxazole groups and thiazole groups have been frequently reported as materials for electron injection and transportation layers, as described in the literature Chem. Mater. 2004, No. 16, p. 4556.

U.S. Pat. Nos. 5,645,948 and 5,766,779 disclose a representative material, 1,3,5-tris (1-phenyl-1H-benzimidazol-2-yl) benzene (TPBI), for electron transportation having blue emission. TPBI has three N-phenyl benzimidazole groups, in 1,3,5-substitution sites of benzene and functions both as an electron transporting and an emitting material. However, TPBI has lower operational stability.

U.S. Pat. No. 6,878,469 discloses a compound, wherein the 2-phenyl benzimidazolyl group is linked to the C-2, C-6 positions of anthracene framework. US20080125593and KR20100007143 disclose electron transporting materials comprising imidazopyridyl or benzimidazolyl groups in its molecular skeleton, exhibiting low driving voltage and high efficiency. However, these materials also lack operational stability.

SUMMARY OF THE INVENTION

1. The inventors made an extensive research to solve the above mentioned problems, by using a compound of specified structure for organic electroluminescent device, represented by the general formula (I) of:

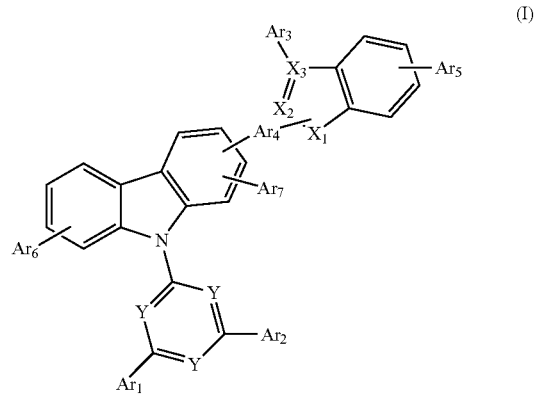

(I)

wherein $X_1$, $X_2$, $X_3$, and Y individually represent a heteroatom selected from the group consisting of N, O, B, and S, with at least 2 heteroatoms forming a ring structure; $X_1$, $X_2$, $X_3$, Y may be the same or different;

$Ar_1$, $Ar_2$, $Ar_3$, and $Ar_4$ each independently represent $C_{1-16}$ alkyl substituted, $C_{6-18}$ is aryl substituted, unsubstituted $C_{6-14}$ aromatic hydrocarbon group; or $C_{3-15}$ heterocyclic aromatic hydrocarbon group containing heteroatoms selected from the group consisting of N, O, and S;

$Ar_5$, $Ar_6$, and $Ar_7$ each represent $C_{1-16}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

2. In another aspect of the present invention, there is provided a process for producing the specific compounds represented by the general formula (I).

3. The compound according to the present invention represented by the general formula (I) is capable of being made into an amorphous thin film by means of vacuum deposition method or spin coating method, for organic electroluminescent devices.
4. Further aspect of this invention relates to an organic electroluminescent device that utilizes the aforementioned compound represented by the general formula (I), in electron transporting layer or electron injection layer as a single material or in combination with a n-type dopant material.
5. Another aspect of this invention relates to an organic electroluminescent device that utilizes the aforementioned compound represented by the general formula (I), in one of the layers described as light emitting layer or hole blocking layer or electron blocking layer.
6. Yet another aspect of this invention relates to an organic electroluminescent device that utilizes the aforementioned compound represented by the general formula (I), in the light emitting layer used in combination with a fluorescent or a phosphorescent emitter.
7. Furthermore, the invention compound represented by the general formula (I), employed in fabricating fluorescent or phosphorescent organic electroluminescent devices.
8. Organic electroluminescent devices comprising the invention compound represented by the general formula (I), employed in any of the organic layers described above, exhibit a longer lifetime and better thermal stability with high efficiency and low driving voltage.
9. In addition, by using the organic compound of the present invention represented by the general formula (I), employed in any of the organic layers described above, it becomes possible to provide an organic electroluminescent device which can emit white light.

DETAILED DESCRIPTION OF THE PREFERRED EMBODIMENTS

Figure 1:
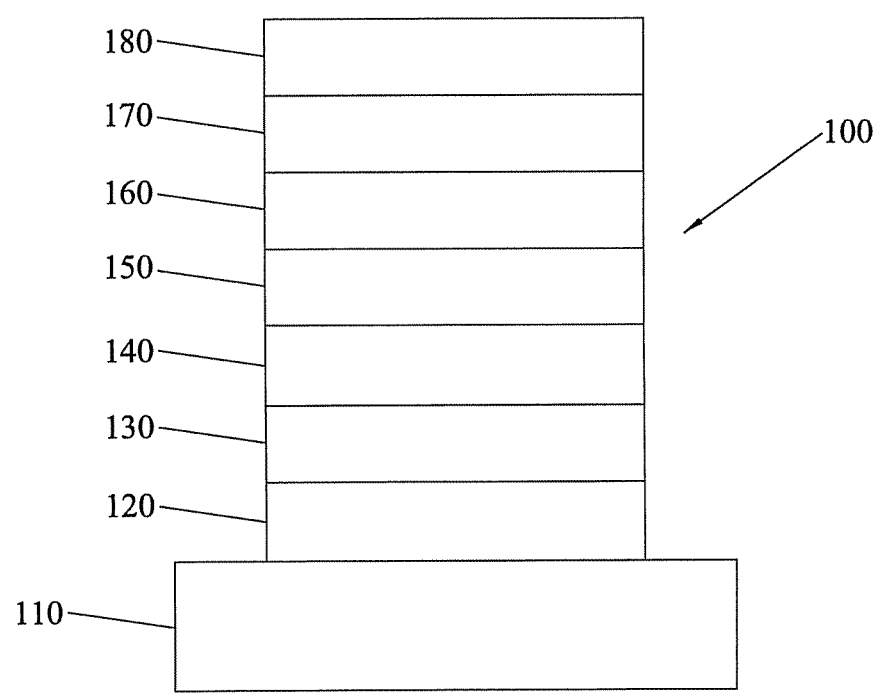
FIG. 1 is a cross-sectional view illustrating one example of an organic light emitting device according to an embodiment of the present invention.

The detailed description of the present invention is illustrated by the following specific examples. Persons skilled in the art can conceive the other advantages and effects of the present invention based on the disclosure contained in the specification of the present invention.

A compound for an organic electroluminescent device according to this invention is represented general formula (I). Preferable examples of the compounds represented by general formula (I) are shown in Table 1, but not limited thereto.

In the general formula (I), wherein $X_1$, $X_2$, $X_3$, and Y individually represent a heteroatom selected from the group consisting of N, O, B, and S, with at least 2 heteroatoms forming a ring structure; $X_1$, $X_2$, $X_3$, Y may be the same or different;

$Ar_1$, $Ar_2$, $Ar_3$, and $Ar_4$ each independently represent $C_{1-16}$ alkyl substituted, $C_{6-18}$ aryl substituted, unsubstituted $C_{6-14}$ aromatic hydrocarbon group; or $C_{3-15}$ heterocyclic aromatic hydrocarbon group containing heteroatoms selected from the group consisting of N, O, and S;

$Ar_5$, $Ar_6$, and $Ar_7$ each represent $C_{1-16}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

TABLE 1
Compound
1-1
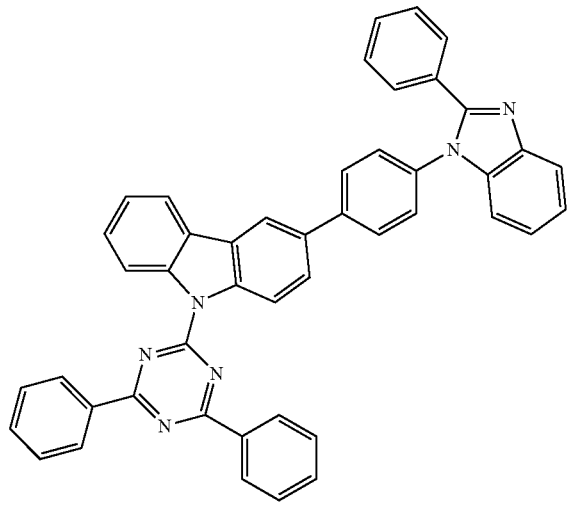 [SMILES: c1ccc(-c2nc(-c3ccccc3)nc(-n3c4ccccc4c4cc(-c5ccc(-n6c(-c7ccccc7)nc7ccccc76)cc5)ccc43)n2)cc1]
Compound
1-2
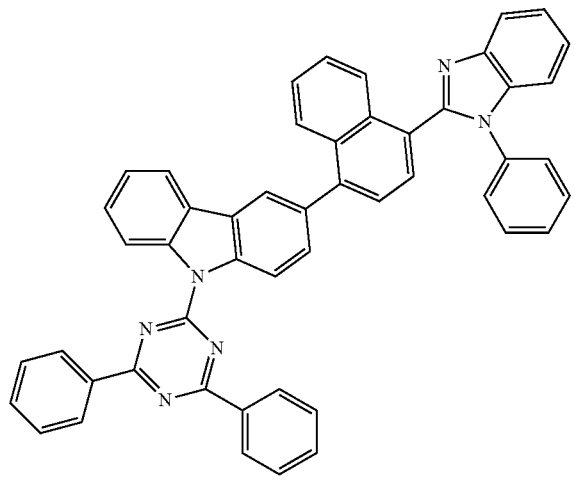 [SMILES: c1ccc(-c2nc(-c3ccccc3)nc(-n3c4ccccc4c4cc(-c5ccc(-c6nc7ccccc7n6-c6ccccc6)c6ccccc56)ccc43)n2)cc1]
Compound
1-3
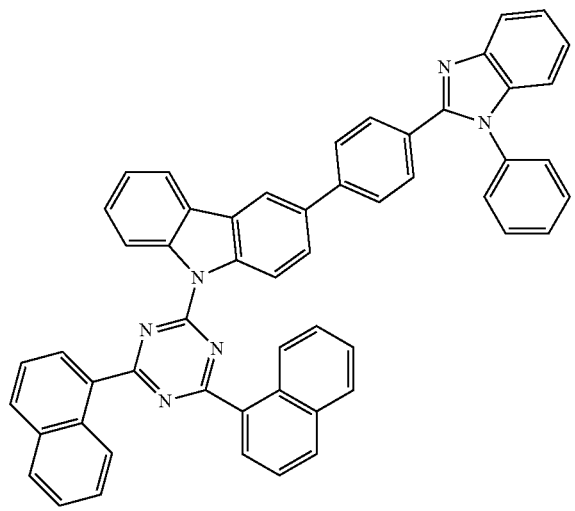 [SMILES: c1ccc(-n2c(-c3ccc(-c4ccc5c(c4)c4ccccc4n5-c4nc(-c5cccc6ccccc56)nc(-c5cccc6ccccc56)n4)cc3)nc3ccccc32)cc1]

TABLE 1-continued
Compound 1-4
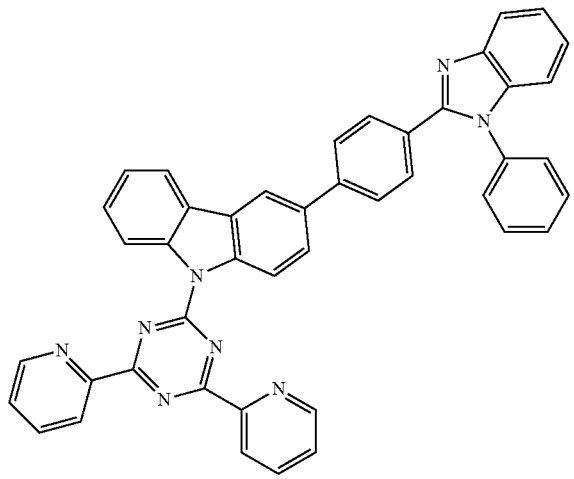
Compound 1-5
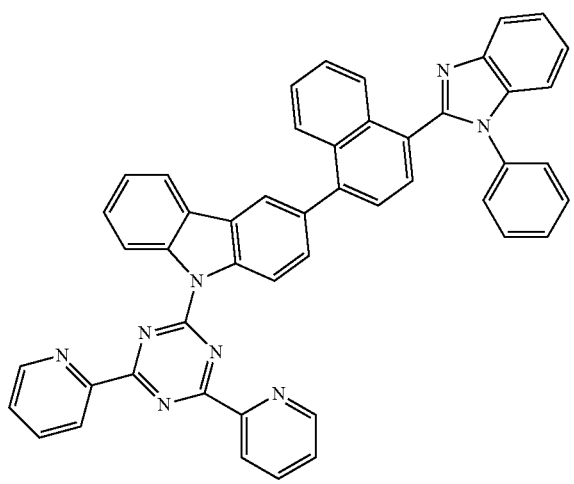 [SMILES: c1ccc(-n2c(-c3ccc(-c4ccc5c(c4)c4ccccc4n5-c4nc(-c5ccccn5)nc(-c5ccccn5)n4)c4ccccc34)nc3ccccc32)cc1]
Compound 1-6
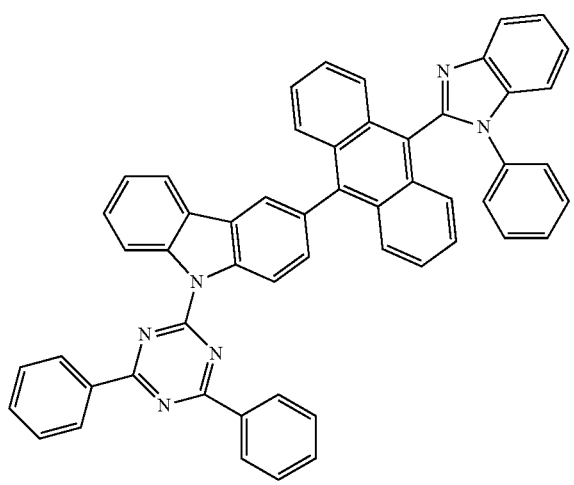 [SMILES: c1ccc(-c2nc(-c3ccccc3)nc(-n3c4ccccc4c4cc(-c5c6ccccc6c(-c6nc7ccccc7n6-c6ccccc6)c6ccccc56)ccc43)n2)cc1]

TABLE 1-continued
Compound 1-7
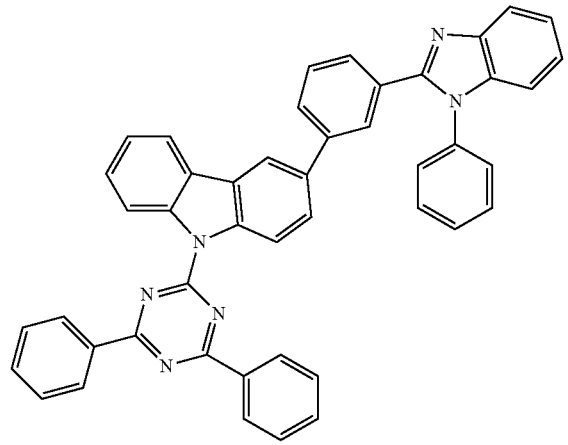 [SMILES: c1ccc(-c2nc(-c3ccccc3)nc(-n3c4ccccc4c4cc(-c5cccc(-c6nc7ccccc7n6-c6ccccc6)c5)ccc43)n2)cc1]
Compound 1-8
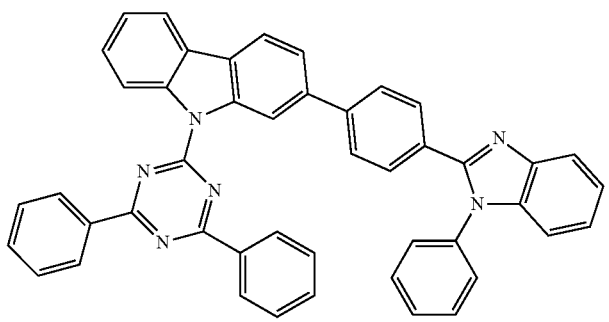 [SMILES: c1ccc(-c2nc(-c3ccccc3)nc(-n3c4ccccc4c4ccc(-c5ccc(-c6nc7ccccc7n6-c6ccccc6)cc5)cc43)n2)cc1]
Compound 1-9
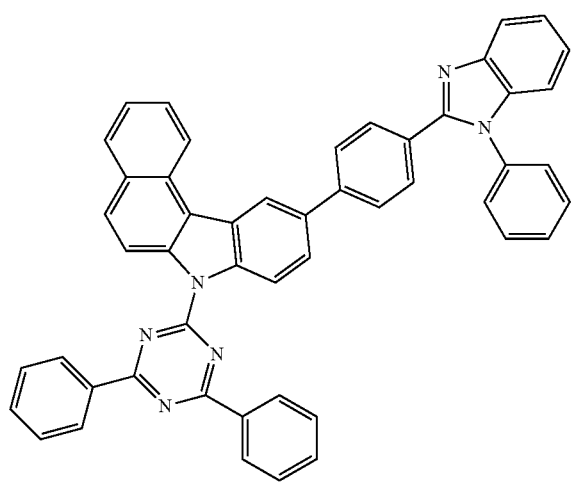 [SMILES: c1ccc(-c2nc(-c3ccccc3)nc(-n3c4ccc(-c5ccc(-c6nc7ccccc7n6-c6ccccc6)cc5)cc4c4c5ccccc5ccc43)n2)cc1]

TABLE 1-continued
Compound 1-10
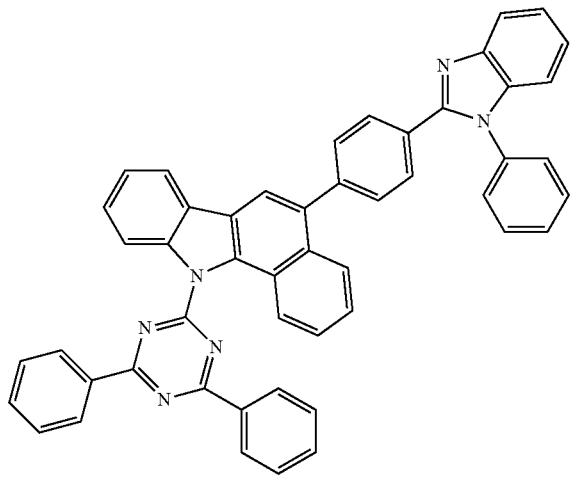 [SMILES: c1ccc(-c2nc(-c3ccccc3)nc(-n3c4ccccc4c4cc(-c5ccc(-c6nc7ccccc7n6-c6ccccc6)cc5)c5ccccc5c43)n2)cc1]
Compound 1-11
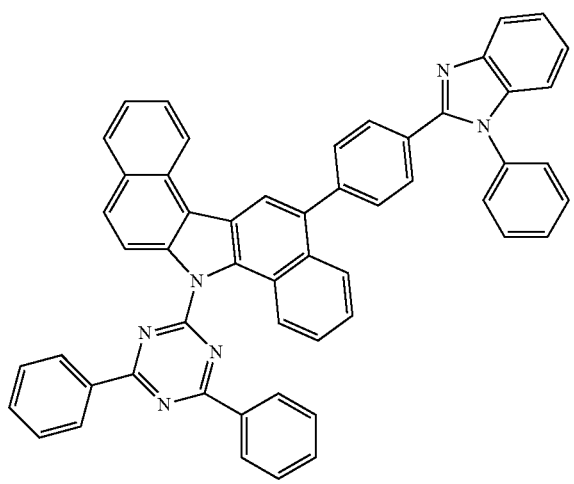 [SMILES: c1ccc(-c2nc(-c3ccccc3)nc(-n3c4ccc5ccccc5c4c4cc(-c5ccc(-c6nc7ccccc7n6-c6ccccc6)cc5)c5ccccc5c43)n2)cc1]
Compound 1-12
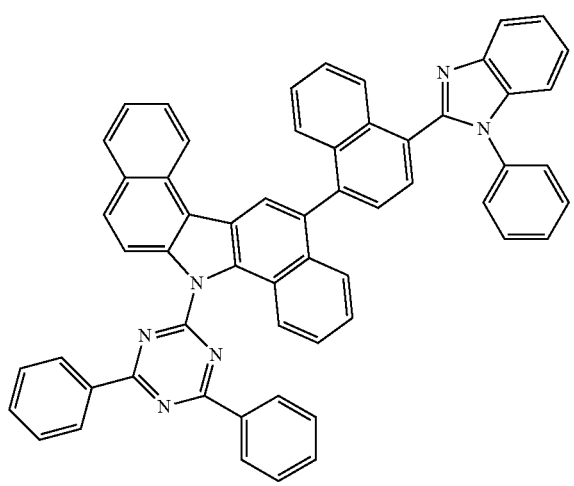 [SMILES: c1ccc(-c2nc(-c3ccccc3)nc(-n3c4ccc5ccccc5c4c4cc(-c5ccc(-c6nc7ccccc7n6-c6ccccc6)c6ccccc56)c5ccccc5c43)n2)cc1]

TABLE 1-continued
Compound 1-13
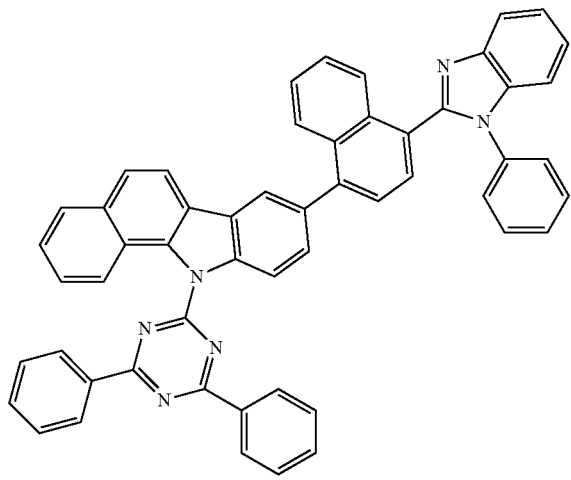 [SMILES: c1ccc(-c2nc(-c3ccccc3)nc(-n3c4ccc(-c5ccc(-c6nc7ccccc7n6-c6ccccc6)c6ccccc56)cc4c4ccc5ccccc5c43)n2)cc1]
Compound 1-14
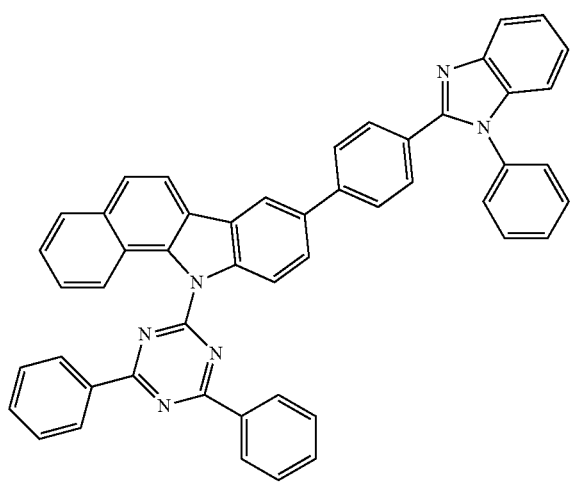 [SMILES: c1ccc(-c2nc(-c3ccccc3)nc(-n3c4ccc(-c5ccc(-c6nc7ccccc7n6-c6ccccc6)cc5)cc4c4ccc5ccccc5c43)n2)cc1]
Compound 1-15
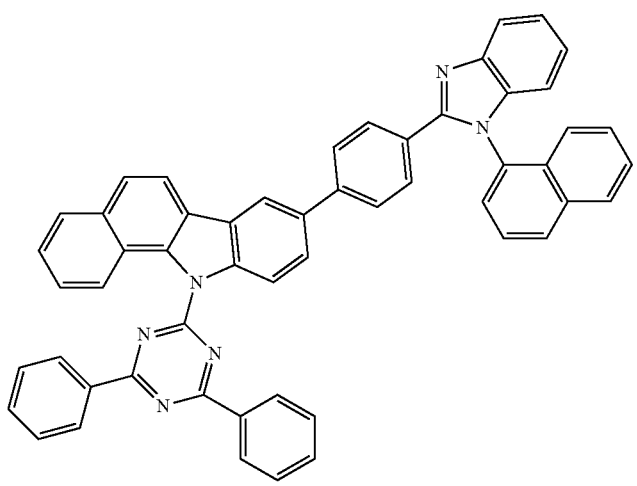 [SMILES: c1ccc(-c2nc(-c3ccccc3)nc(-n3c4ccc(-c5ccc(-c6nc7ccccc7n6-c6cccc7ccccc67)cc5)cc4c4ccc5ccccc5c43)n2)cc1]

TABLE 1-continued
Compound 1-16
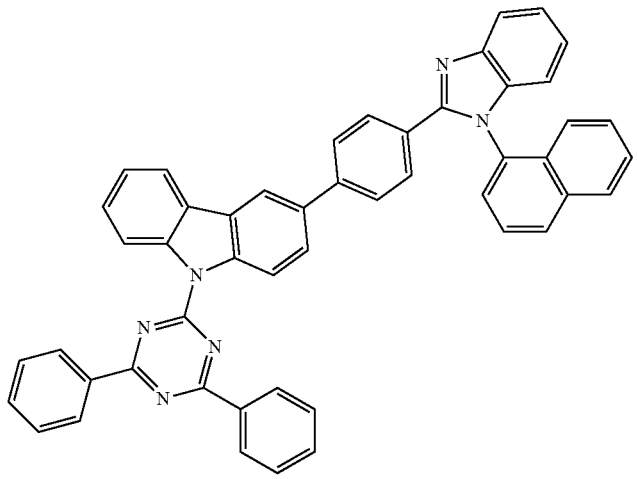 [SMILES: c1ccc(-c2nc(-c3ccccc3)nc(-n3c4ccccc4c4cc(-c5ccc(-c6nc7ccccc7n6-c6cccc7ccccc67)cc5)ccc43)n2)cc1]
Compound 1-17
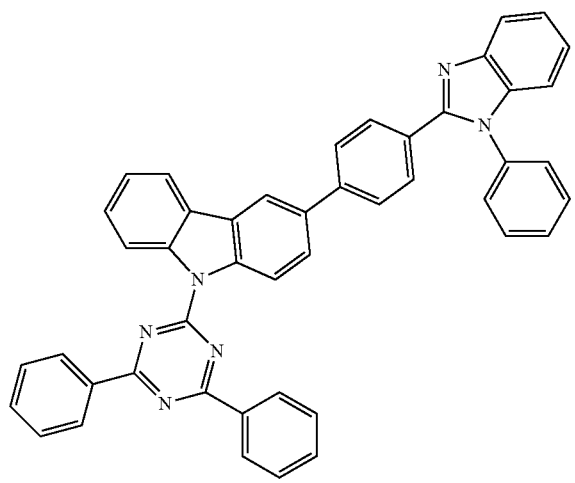 [SMILES: c1ccc(-c2nc(-c3ccccc3)nc(-n3c4ccccc4c4cc(-c5ccc(-c6nc7ccccc7n6-c6ccccc6)cc5)ccc43)n2)cc1]
Compound 1-18
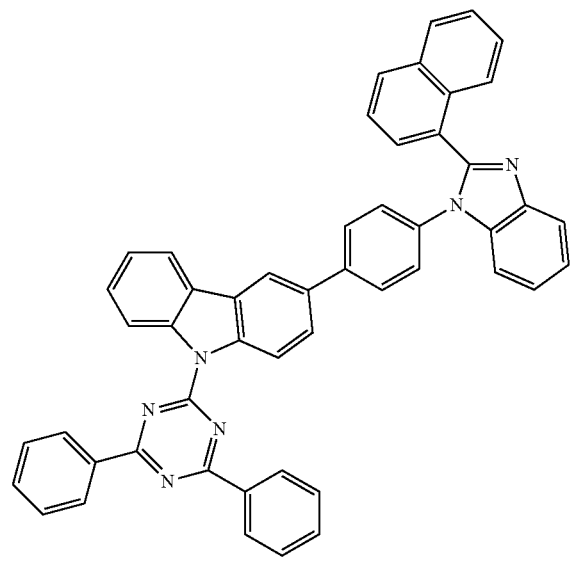 [SMILES: c1ccc(-c2nc(-c3ccccc3)nc(-n3c4ccccc4c4cc(-c5ccc(-n6c(-c7cccc8ccccc78)nc7ccccc76)cc5)ccc43)n2)cc1]

TABLE 1-continued
Compound 1-19
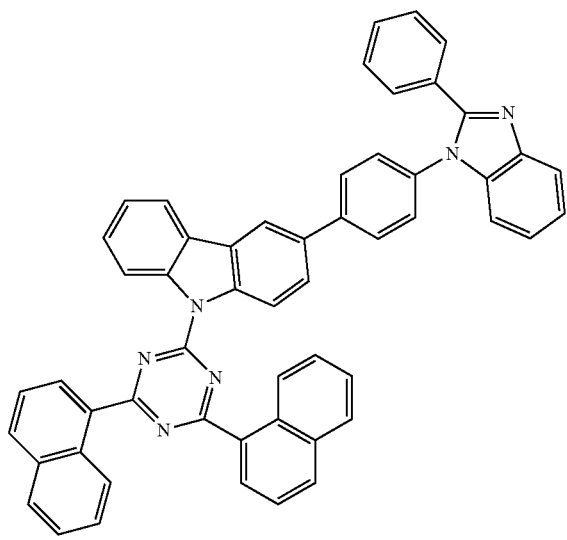 [SMILES: c1ccc(-c2nc3ccccc3n2-c2ccc(-c3ccc4c(c3)c3ccccc3n4-c3nc(-c4cccc5ccccc45)nc(-c4cccc5ccccc45)n3)cc2)cc1]
Compound 1-20
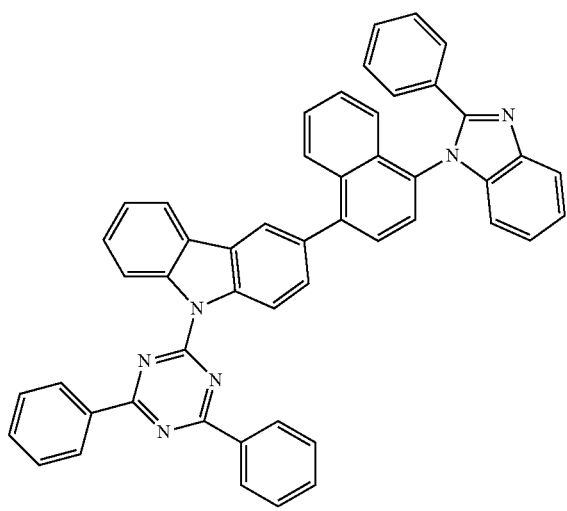 [SMILES: c1ccc(-c2nc(-c3ccccc3)nc(-n3c4ccccc4c4cc(-c5ccc(-n6c(-c7ccccc7)nc7ccccc76)c6ccccc56)ccc43)n2)cc1]
Compound 1-21
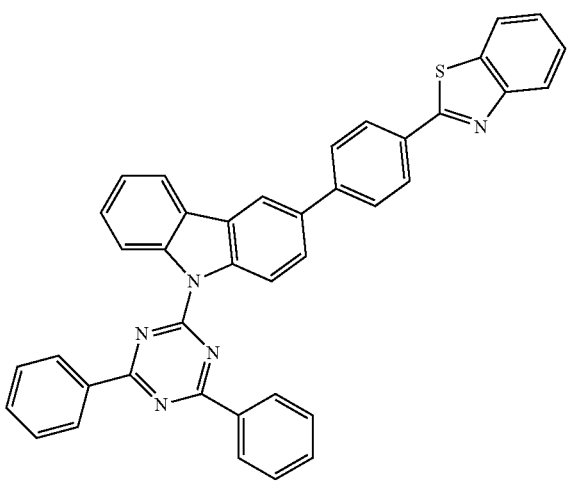 [SMILES: c1ccc(-c2nc(-c3ccccc3)nc(-n3c4ccccc4c4cc(-c5ccc(-c6nc7ccccc7s6)cc5)ccc43)n2)cc1]

TABLE 1-continued
Compound 1-22
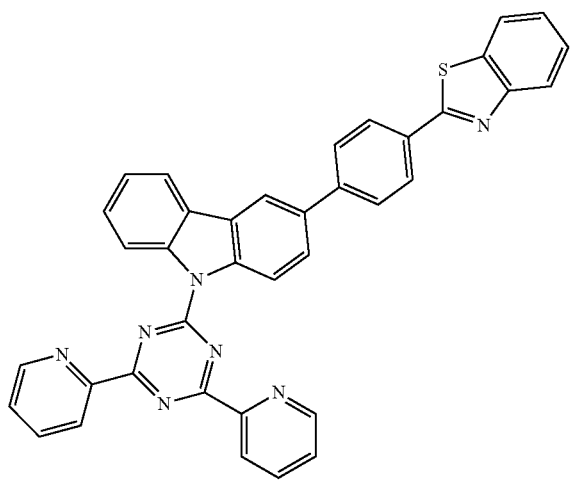 [SMILES: c1ccc(-c2nc(-c3ccccn3)nc(-n3c4ccccc4c4cc(-c5ccc(-c6nc7ccccc7s6)cc5)ccc43)n2)nc1]
Compound 1-23
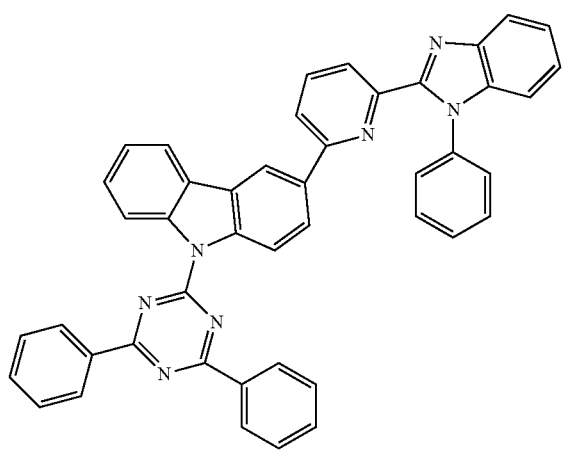 [SMILES: c1ccc(-c2nc(-c3ccccc3)nc(-n3c4ccccc4c4cc(-c5cccc(-c6nc7ccccc7n6-c6ccccc6)n5)ccc43)n2)cc1]
Compound 1-24
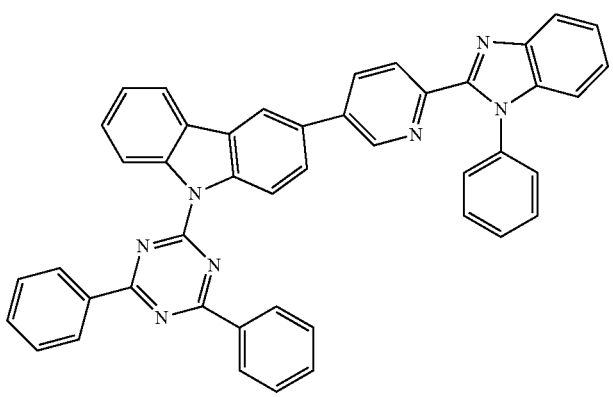 [SMILES: c1ccc(-c2nc(-c3ccccc3)nc(-n3c4ccccc4c4cc(-c5ccc(-c6nc7ccccc7n6-c6ccccc6)nc5)ccc43)n2)cc1]

TABLE 1-continued
Compound 1-25
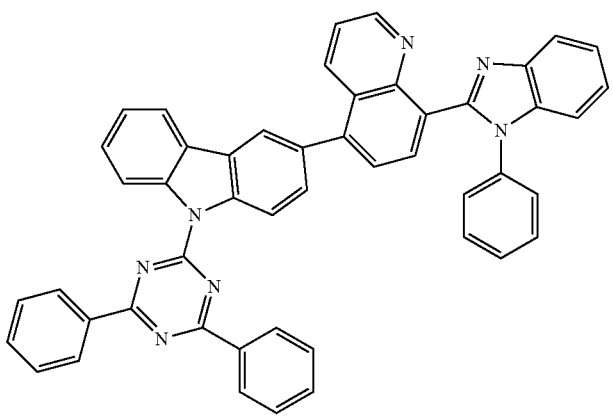 [SMILES: c1ccc(-c2nc(-c3ccccc3)nc(-n3c4ccccc4c4cc(-c5ccc(-c6nc7ccccc7n6-c6ccccc6)c6ncccc56)ccc43)n2)cc1]
Compound 1-26
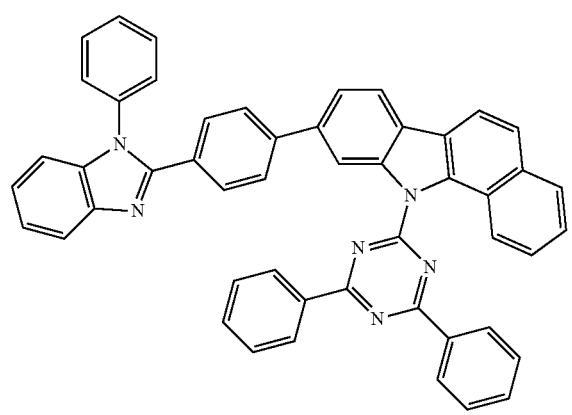 [SMILES: c1ccc(-c2nc(-c3ccccc3)nc(-n3c4cc(-c5ccc(-c6nc7ccccc7n6-c6ccccc6)cc5)ccc4c4ccc5ccccc5c43)n2)cc1]
Compound 1-27
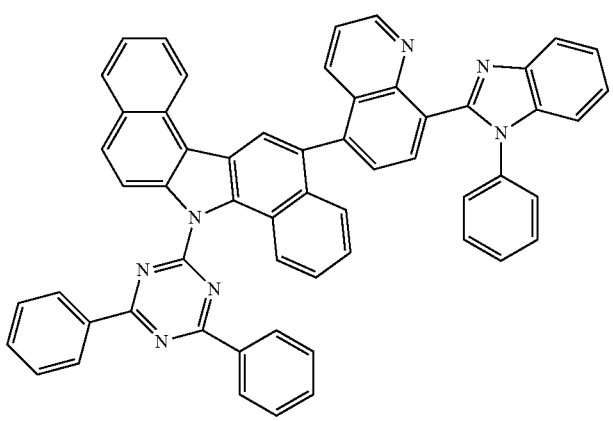 [SMILES: c1ccc(-c2nc(-c3ccccc3)nc(-n3c4ccc5ccccc5c4c4cc(-c5ccc(-c6nc7ccccc7n6-c6ccccc6)c6ncccc56)c5ccccc5c43)n2)cc1]
Compound 1-28
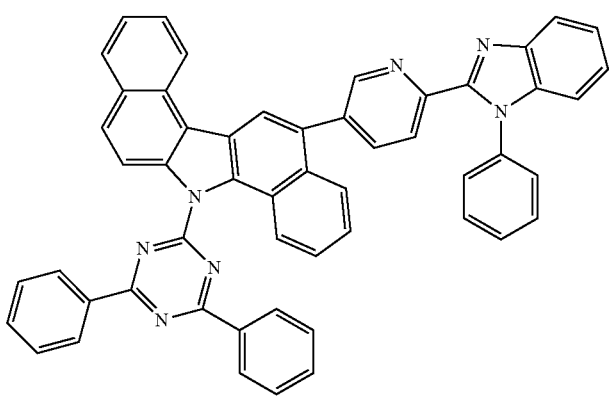 [SMILES: c1ccc(-c2nc(-c3ccccc3)nc(-n3c4ccc5ccccc5c4c4cc(-c5ccc(-c6nc7ccccc7n6-c6ccccc6)nc5)c5ccccc5c43)n2)cc1]

TABLE 1-continued
Compound
1-29
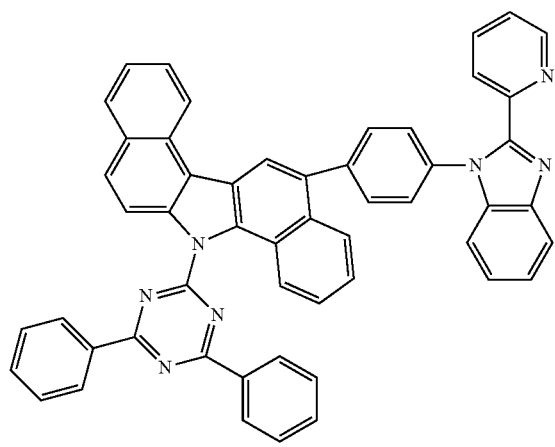 [SMILES: c1ccc(-c2nc(-c3ccccc3)nc(-n3c4ccc5ccccc5c4c4cc(-c5ccc(-n6c(-c7ccccn7)nc7ccccc76)cc5)c5ccccc5c43)n2)cc1]
Compound
1-30
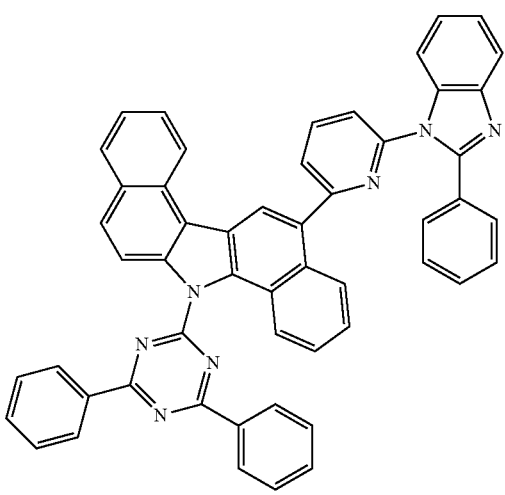 [SMILES: c1ccc(-c2nc(-c3ccccc3)nc(-n3c4ccc5ccccc5c4c4cc(-c5cccc(-n6c(-c7ccccc7)nc7ccccc76)n5)c5ccccc5c43)n2)cc1]
Compound
1-31
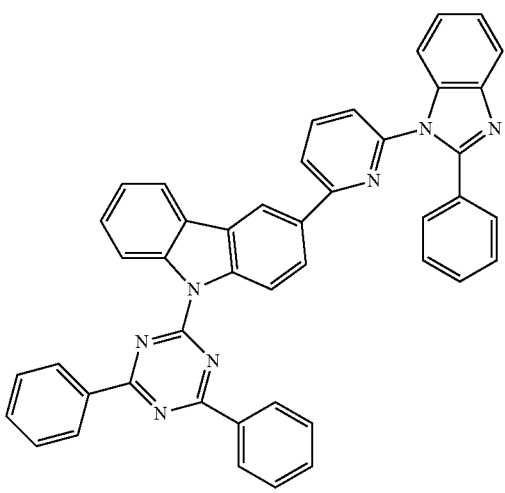 [SMILES: c1ccc(-c2nc(-c3ccccc3)nc(-n3c4ccccc4c4cc(-c5cccc(-n6c(-c7ccccc7)nc7ccccc76)n5)ccc43)n2)cc1]

TABLE 1-continued
Compound
1-32
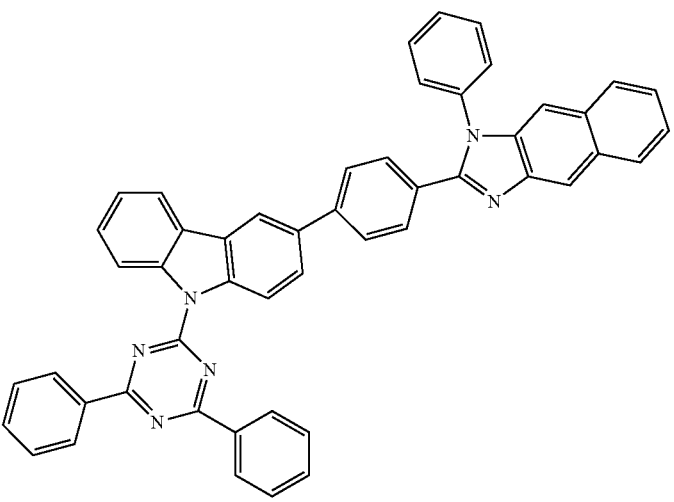 [SMILES: c1ccc(-c2nc(-c3ccccc3)nc(-n3c4ccccc4c4cc(-c5ccc(-c6nc7cc8ccccc8cc7n6-c6ccccc6)cc5)ccc43)n2)cc1]
Compound
1-33
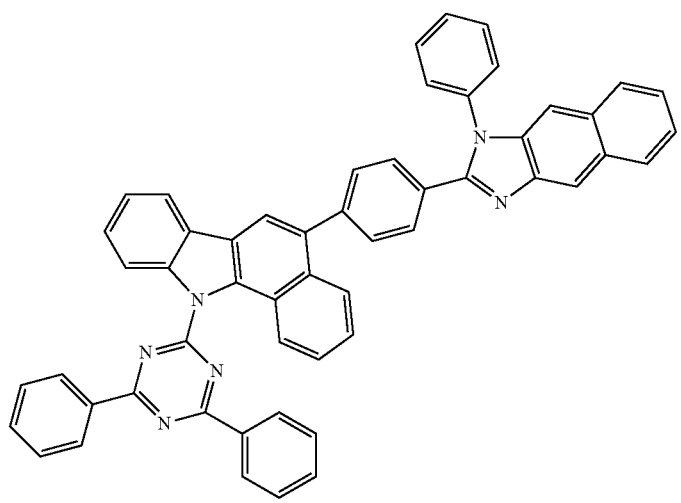 [SMILES: c1ccc(-c2nc(-c3ccccc3)nc(-n3c4ccccc4c4cc(-c5ccc(-c6nc7cc8ccccc8cc7n6-c6ccccc6)cc5)c5ccccc5c43)n2)cc1]
Compound
1-34
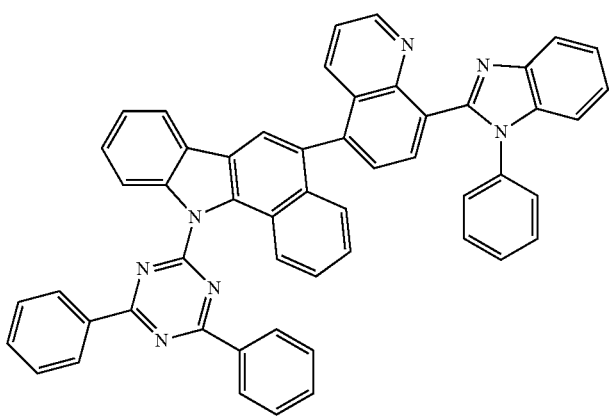 [SMILES: c1ccc(-c2nc(-c3ccccc3)nc(-n3c4ccccc4c4cc(-c5ccc(-c6nc7ccccc7n6-c6ccccc6)c6ncccc56)c5ccccc5c43)n2)cc1]

TABLE 1-continued
Compound 1-35
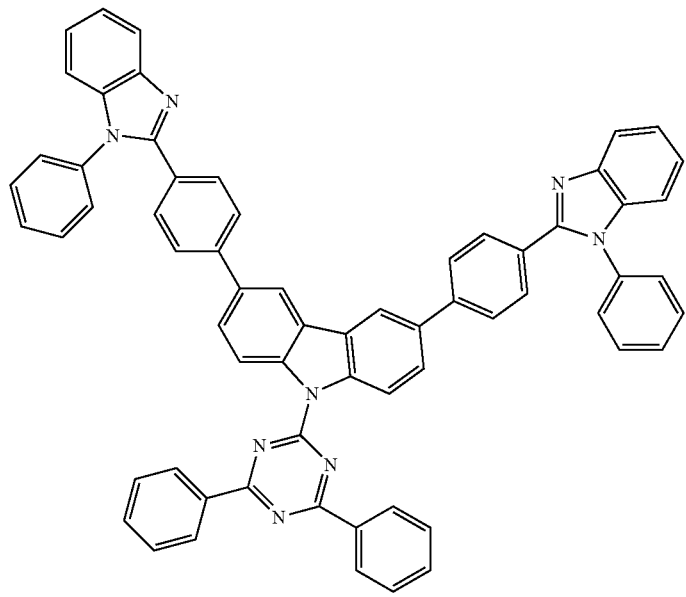 [SMILES: c1ccc(-c2nc(-c3ccccc3)nc(-n3c4ccc(-c5ccc(-c6nc7ccccc7n6-c6ccccc6)cc5)cc4c4cc(-c5ccc(-c6nc7ccccc7n6-c6ccccc6)cc5)ccc43)n2)cc1]
Compound 1-36
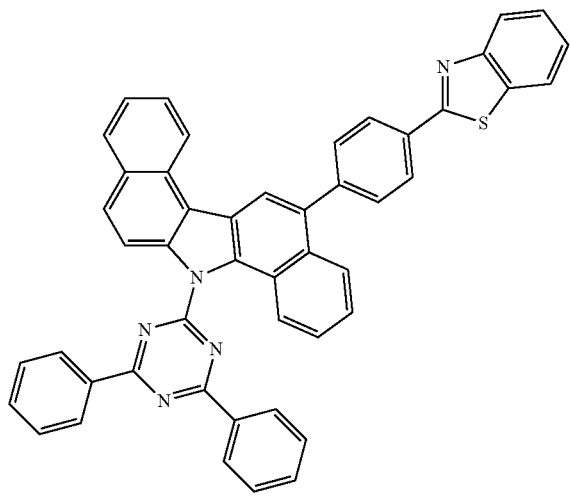 [SMILES: c1ccc(-c2nc(-c3ccccc3)nc(-n3c4ccc5ccccc5c4c4cc(-c5ccc(-c6nc7ccccc7s6)cc5)c5ccccc5c43)n2)cc1]
Compound 1-37
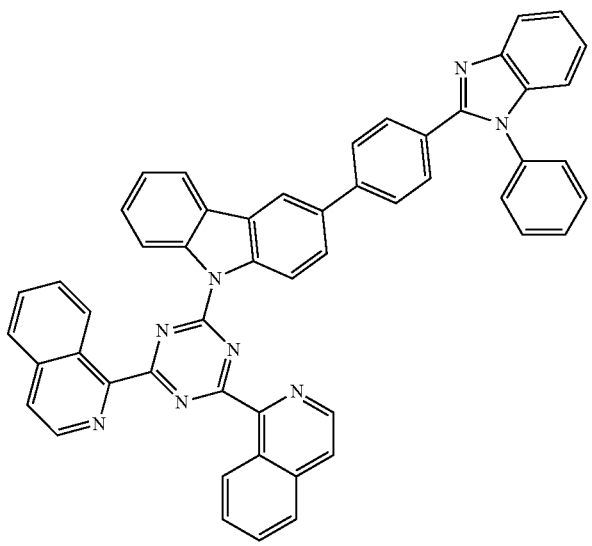 [SMILES: c1ccc(-n2c(-c3ccc(-c4ccc5c(c4)c4ccccc4n5-c4nc(-c5nccc6ccccc56)nc(-c5nccc6ccccc56)n4)cc3)nc3ccccc32)cc1]

TABLE 1-continued
Compound 1-38
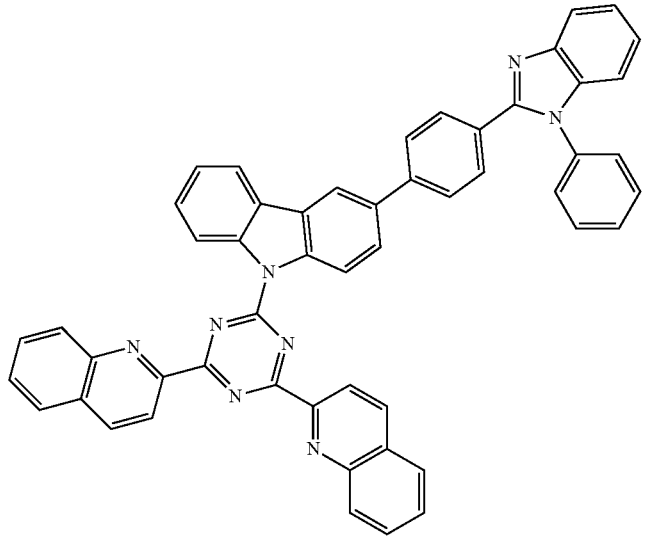 [SMILES: c1ccc(-n2c(-c3ccc(-c4ccc5c(c4)c4ccccc4n5-c4nc(-c5ccc6ccccc6n5)nc(-c5ccc6ccccc6n5)n4)cc3)nc3ccccc32)cc1]
Compound 1-39
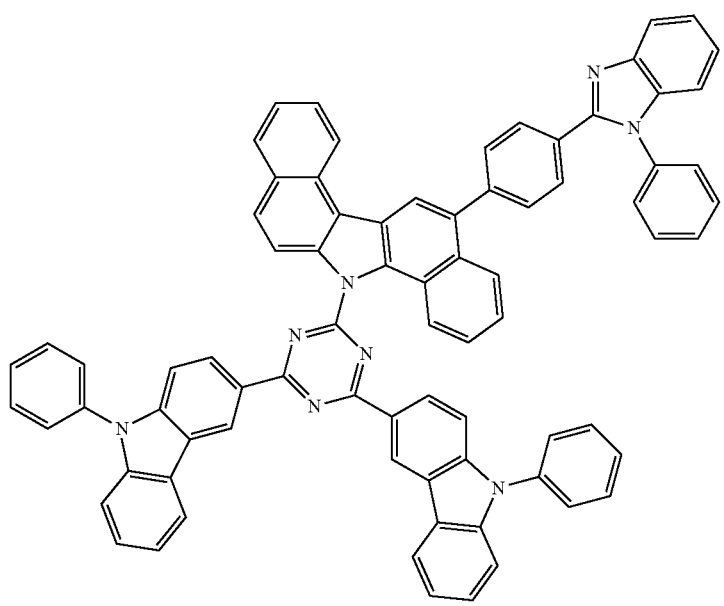 [SMILES: c1ccc(-n2c(-c3ccc(-c4cc5c6c7ccccc7ccc6n(-c6nc(-c7ccc8c(c7)c7ccccc7n8-c7ccccc7)nc(-c7ccc8c(c7)c7ccccc7n8-c7ccccc7)n6)c5c5ccccc45)cc3)nc3ccccc32)cc1]

TABLE 1-continued
Compound
1-40
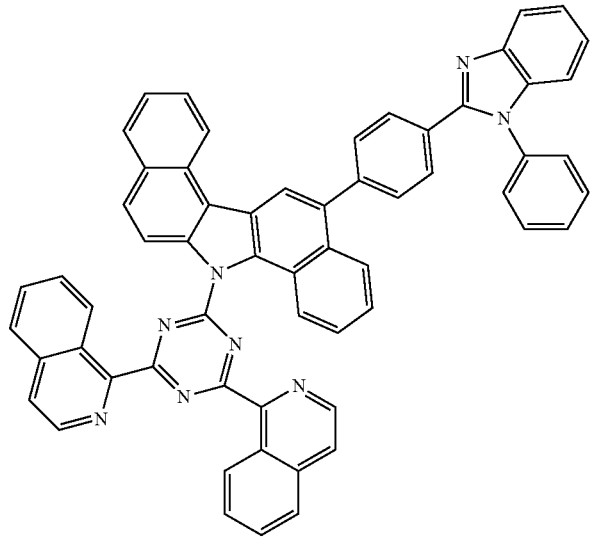 [SMILES: c1ccc(-n2c(-c3ccc(-c4cc5c6c7ccccc7ccc6n(-c6nc(-c7nccc8ccccc78)nc(-c7nccc8ccccc78)n6)c5c5ccccc45)cc3)nc3ccccc32)cc1]
Compound
1-41
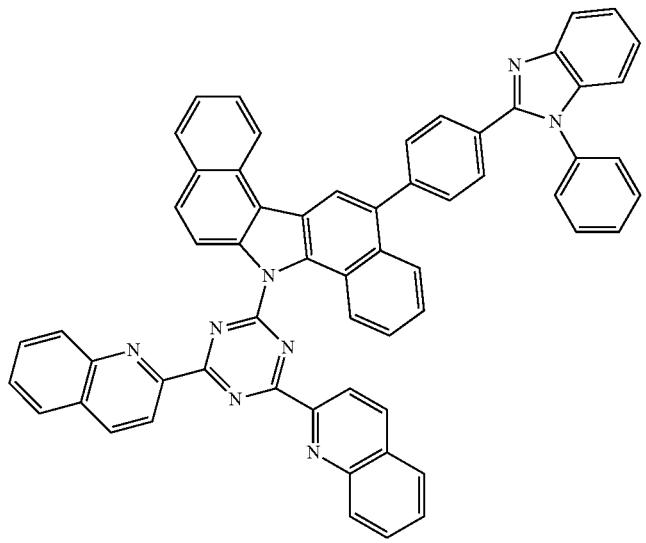 [SMILES: c1ccc(-n2c(-c3ccc(-c4cc5c6c7ccccc7ccc6n(-c6nc(-c7ccc8ccccc8n7)nc(-c7ccc8ccccc8n7)n6)c5c5ccccc45)cc3)nc3ccccc32)cc1]

TABLE 1-continued
Compound
1-42
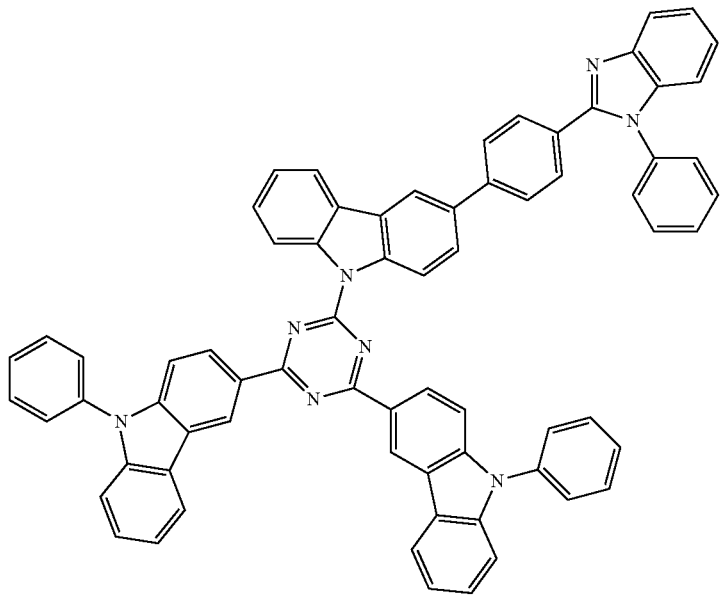 [SMILES: c1ccc(-n2c(-c3ccc(-c4ccc5c(c4)c4ccccc4n5-c4nc(-c5ccc6c(c5)c5ccccc5n6-c5ccccc5)nc(-c5ccc6c(c5)c5ccccc5n6-c5ccccc5)n4)cc3)nc3ccccc32)cc1]
Compound
1-43
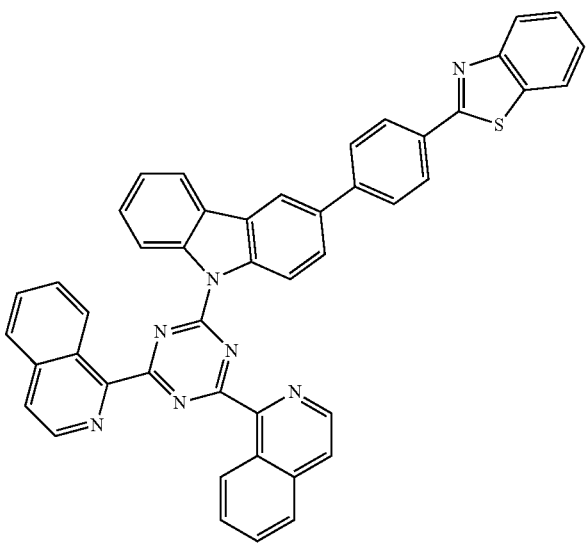 [SMILES: c1ccc2c(-c3nc(-c4nccc5ccccc45)nc(-n4c5ccccc5c5cc(-c6ccc(-c7nc8ccccc8s7)cc6)ccc54)n3)nccc2c1]
Compound
1-44
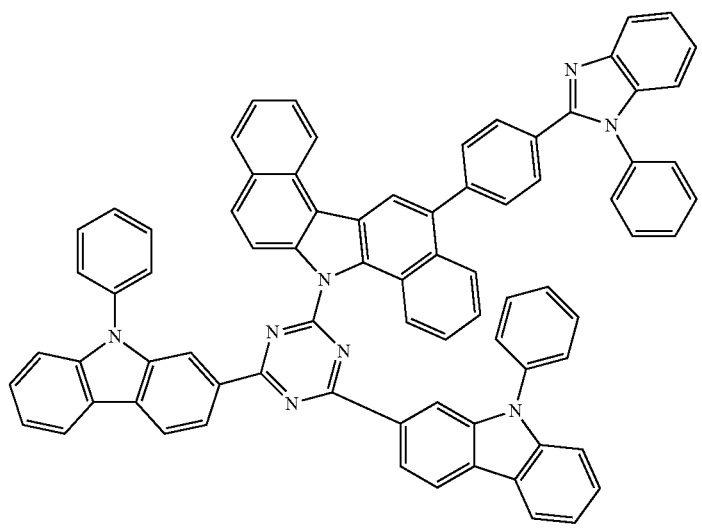 [SMILES: c1ccc(-n2c(-c3ccc(-c4cc5c6c7ccccc7ccc6n(-c6nc(-c7ccc8c9ccccc9n(-c9ccccc9)c8c7)nc(-c7ccc8c9ccccc9n(-c9ccccc9)c8c7)n6)c5c5ccccc45)cc3)nc3ccccc32)cc1]

TABLE 1-continued
Compound 1-45
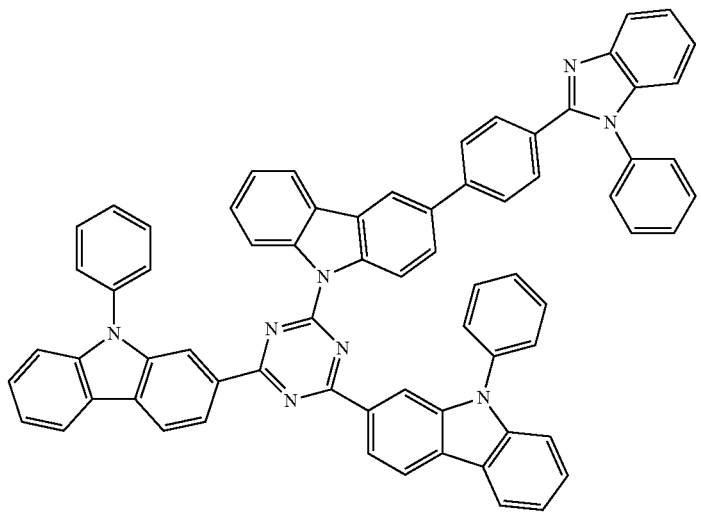 [SMILES: c1ccc(-n2c(-c3ccc(-c4ccc5c(c4)c4ccccc4n5-c4nc(-c5ccc6c7ccccc7n(-c7ccccc7)c6c5)nc(-c5ccc6c7ccccc7n(-c7ccccc7)c6c5)n4)cc3)nc3ccccc32)cc1]
Compound 1-46
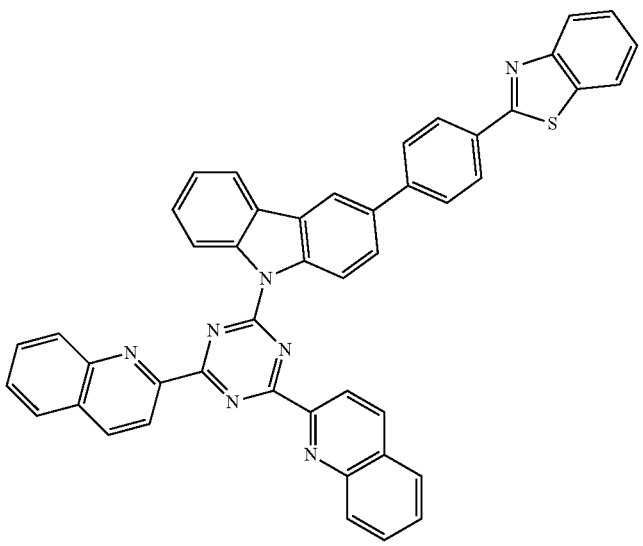 [SMILES: c1ccc2nc(-c3nc(-c4ccc5ccccc5n4)nc(-n4c5ccccc5c5cc(-c6ccc(-c7nc8ccccc8s7)cc6)ccc54)n3)ccc2c1]
Compound 1-47
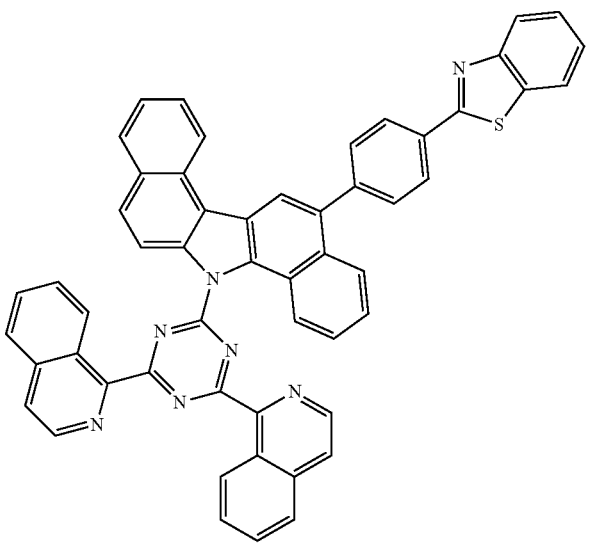 [SMILES: c1ccc2c(-c3nc(-c4nccc5ccccc45)nc(-n4c5ccc6ccccc6c5c5cc(-c6ccc(-c7nc8ccccc8s7)cc6)c6ccccc6c54)n3)nccc2c1]

TABLE 1-continued
Compound
1-48
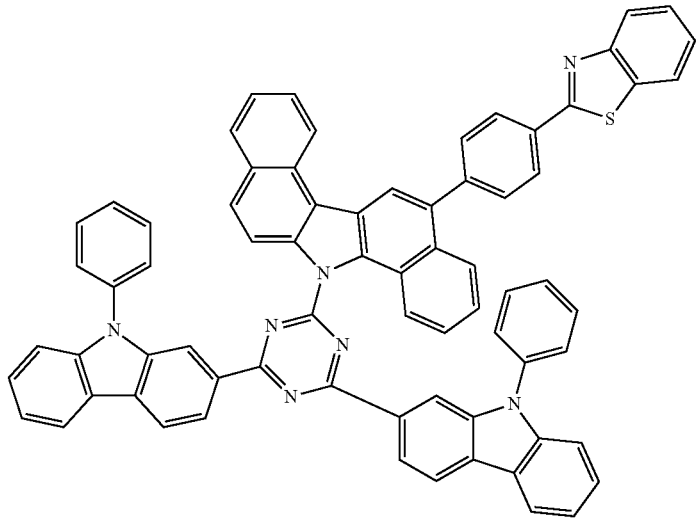 [SMILES: c1ccc(-n2c3ccccc3c3ccc(-c4nc(-c5ccc6c7ccccc7n(-c7ccccc7)c6c5)nc(-n5c6ccc7ccccc7c6c6cc(-c7ccc(-c8nc9ccccc9s8)cc7)c7ccccc7c65)n4)cc32)cc1]
Compound
1-49
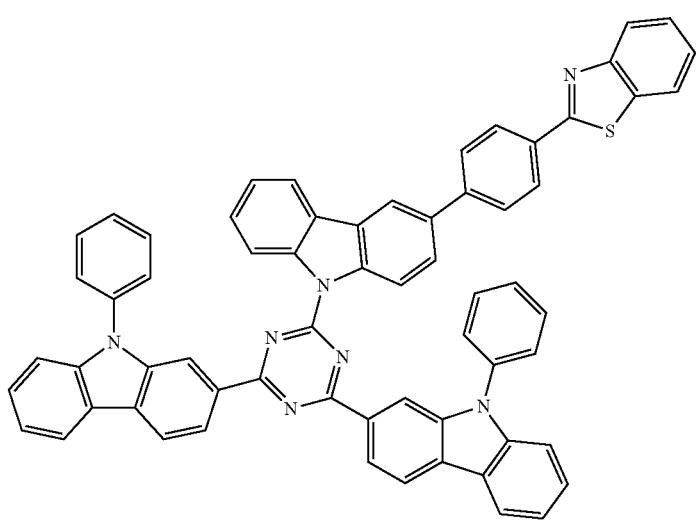 [SMILES: c1ccc(-n2c3ccccc3c3ccc(-c4nc(-c5ccc6c7ccccc7n(-c7ccccc7)c6c5)nc(-n5c6ccccc6c6cc(-c7ccc(-c8nc9ccccc9s8)cc7)ccc65)n4)cc32)cc1]
Compound
1-50
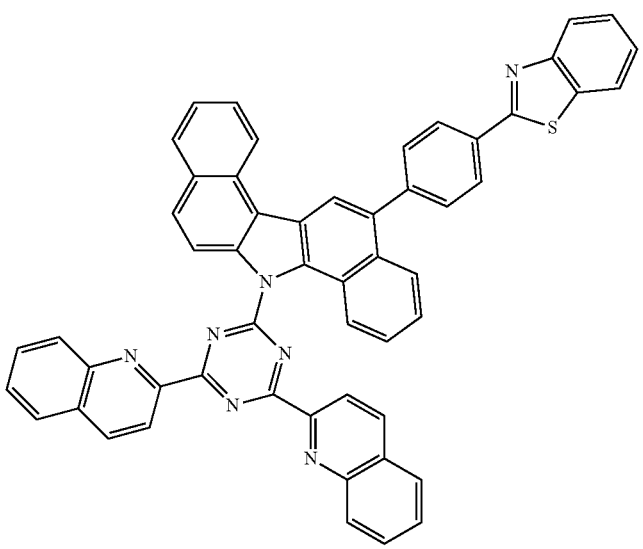 [SMILES: c1ccc2nc(-c3nc(-c4ccc5ccccc5n4)nc(-n4c5ccc6ccccc6c5c5cc(-c6ccc(-c7nc8ccccc8s7)cc6)c6ccccc6c54)n3)ccc2c1]

TABLE 1-continued
Compound 1-51
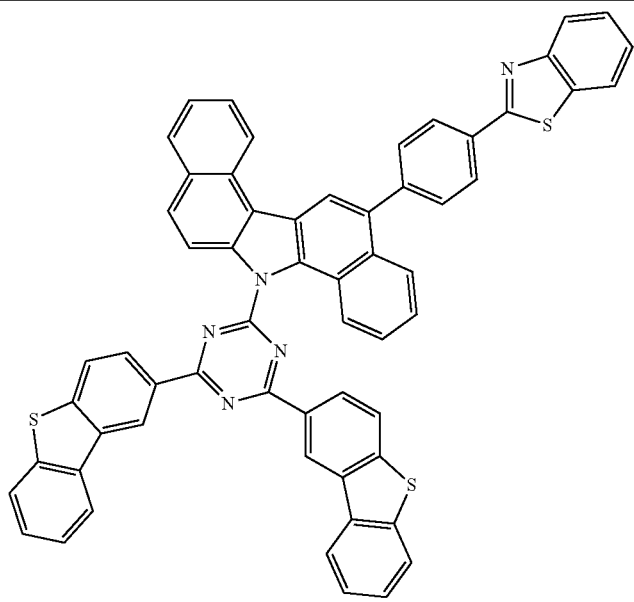
Compound 1-52
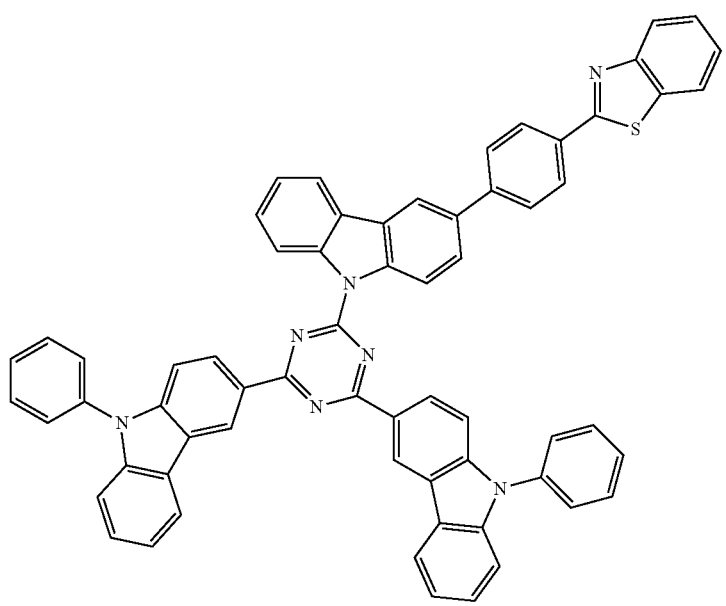 [SMILES: c1ccc(-n2c3ccccc3c3cc(-c4nc(-c5ccc6c(c5)c5ccccc5n6-c5ccccc5)nc(-n5c6ccccc6c6cc(-c7ccc(-c8nc9ccccc9s8)cc7)ccc65)n4)ccc32)cc1]

TABLE 1-continued
Compound
1-53
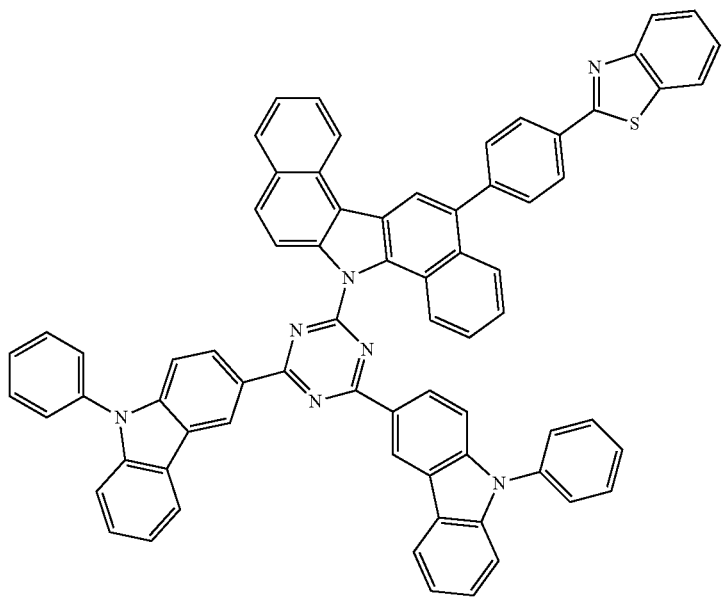 [SMILES: c1ccc(-n2c3ccccc3c3cc(-c4nc(-c5ccc6c(c5)c5ccccc5n6-c5ccccc5)nc(-n5c6ccc7ccccc7c6c6cc(-c7ccc(-c8nc9ccccc9s8)cc7)c7ccccc7c65)n4)ccc32)cc1]
Compound
1-54
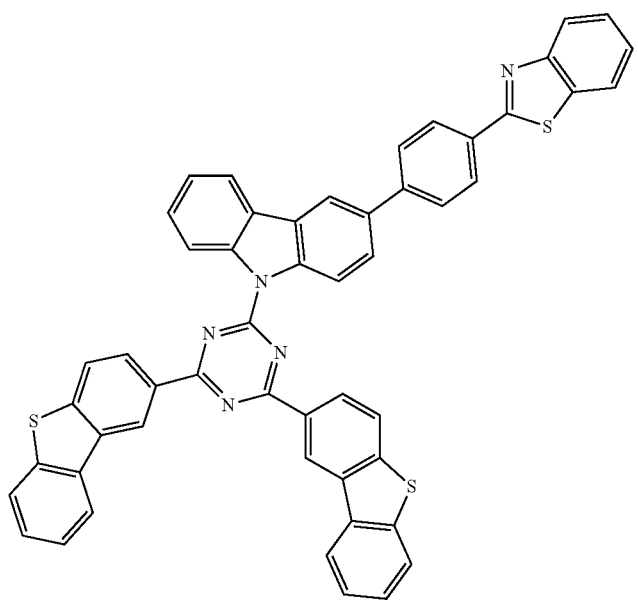 [SMILES: c1ccc2sc(-c3ccc(-c4ccc5c(c4)c4ccccc4n5-c4nc(-c5ccc6sc7ccccc7c6c5)nc(-c5ccc6sc7ccccc7c6c5)n4)cc3)nc2c1]

TABLE 1-continued
Compound
1-55
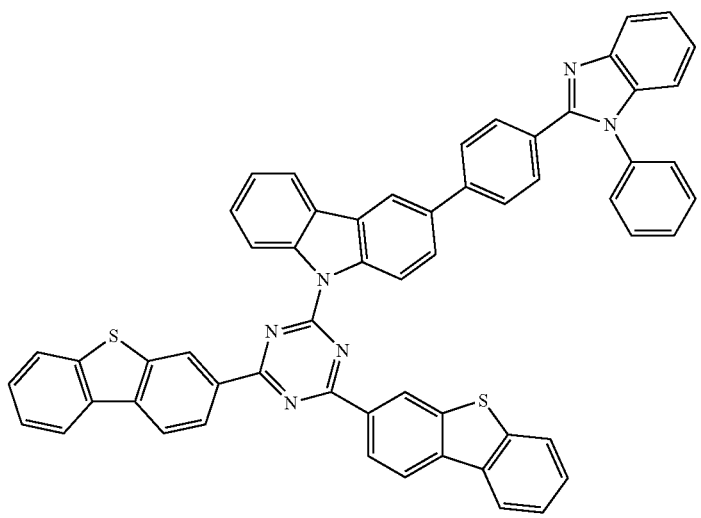 [SMILES: c1ccc(-n2c(-c3ccc(-c4ccc5c(c4)c4ccccc4n5-c4nc(-c5ccc6c(c5)sc5ccccc56)nc(-c5ccc6c(c5)sc5ccccc56)n4)cc3)nc3ccccc32)cc1]
Compound
1-56
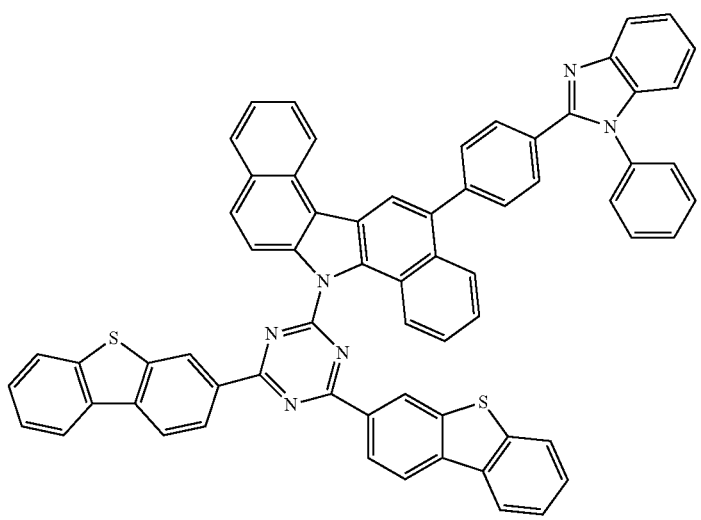 [SMILES: c1ccc(-n2c(-c3ccc(-c4cc5c6c7ccccc7ccc6n(-c6nc(-c7ccc8c(c7)sc7ccccc78)nc(-c7ccc8c(c7)sc7ccccc78)n6)c5c5ccccc45)cc3)nc3ccccc32)cc1]
Compound
1-57
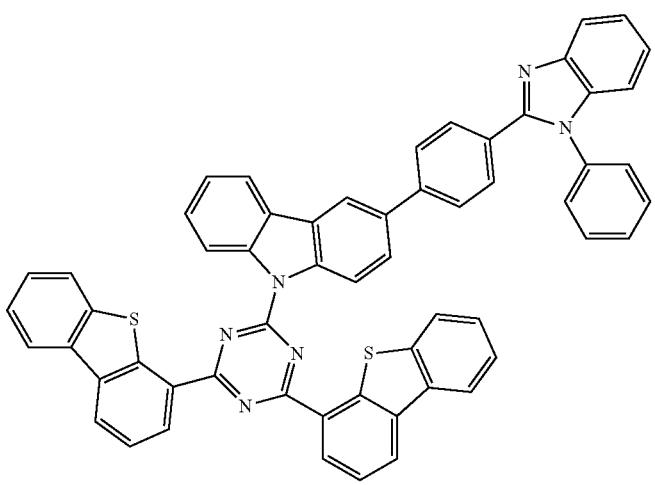 [SMILES: c1ccc(-n2c(-c3ccc(-c4ccc5c(c4)c4ccccc4n5-c4nc(-c5cccc6c5sc5ccccc56)nc(-c5cccc6c5sc5ccccc56)n4)cc3)nc3ccccc32)cc1]

TABLE 1-continued
Compound
1-58
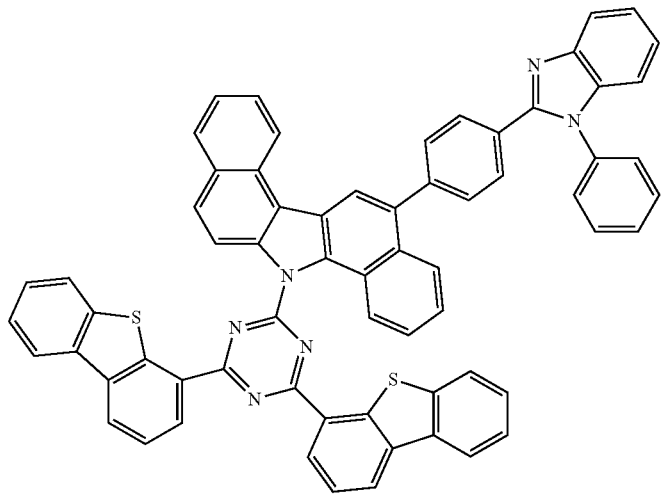 [SMILES: c1ccc(-n2c(-c3ccc(-c4cc5c6c7ccccc7ccc6n(-c6nc(-c7cccc8c7sc7ccccc78)nc(-c7cccc8c7sc7ccccc78)n6)c5c5ccccc45)cc3)nc3ccccc32)cc1]
Compound
1-59
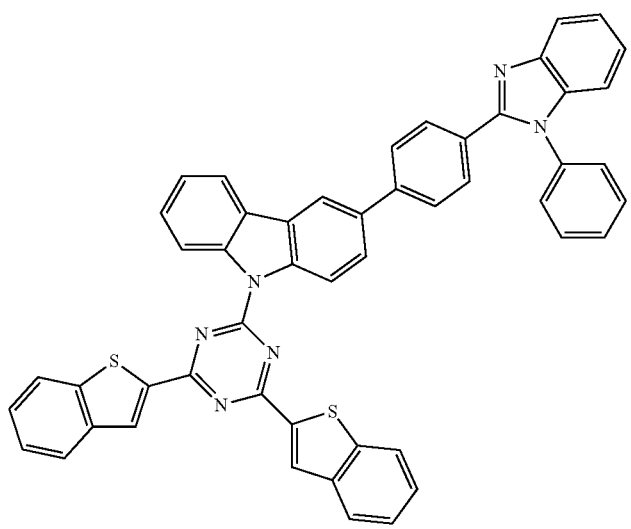 [SMILES: c1ccc(-n2c(-c3ccc(-c4ccc5c(c4)c4ccccc4n5-c4nc(-c5cc6ccccc6s5)nc(-c5cc6ccccc6s5)n4)cc3)nc3ccccc32)cc1]
Compound
1-60
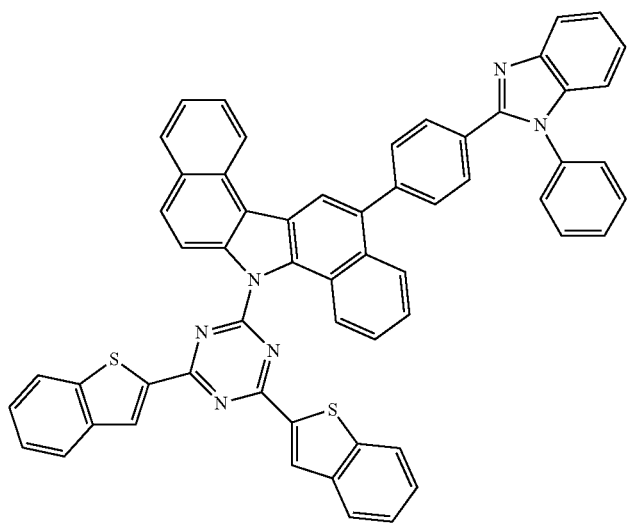 [SMILES: c1ccc(-n2c(-c3ccc(-c4cc5c6c7ccccc7ccc6n(-c6nc(-c7cc8ccccc8s7)nc(-c7cc8ccccc8s7)n6)c5c5ccccc45)cc3)nc3ccccc32)cc1]

TABLE 1-continued
Compound 1-61
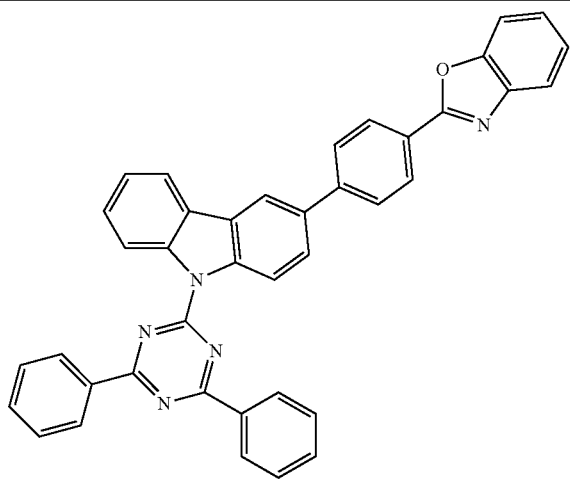
Compound 1-62
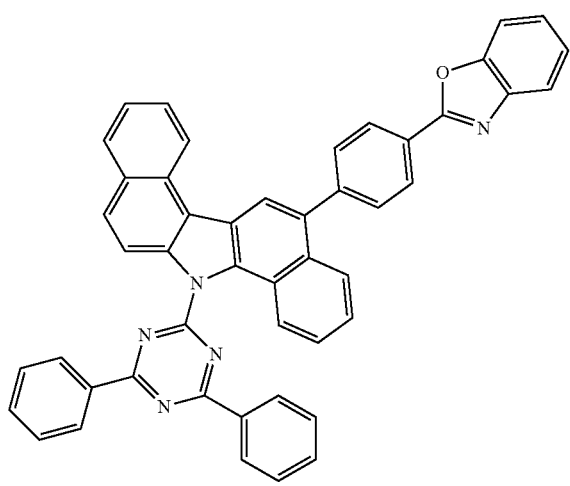 [SMILES: c1ccc(-c2nc(-c3ccccc3)nc(-n3c4ccc5ccccc5c4c4cc(-c5ccc(-c6nc7ccccc7o6)cc5)c5ccccc5c43)n2)cc1]
Exemplary compounds 1-1 to 1-62 represented by general formula (I), may be prepared through a sequence of reactions shown in the synthetic schemes 1-8, but not limited thereto.
Scheme 1
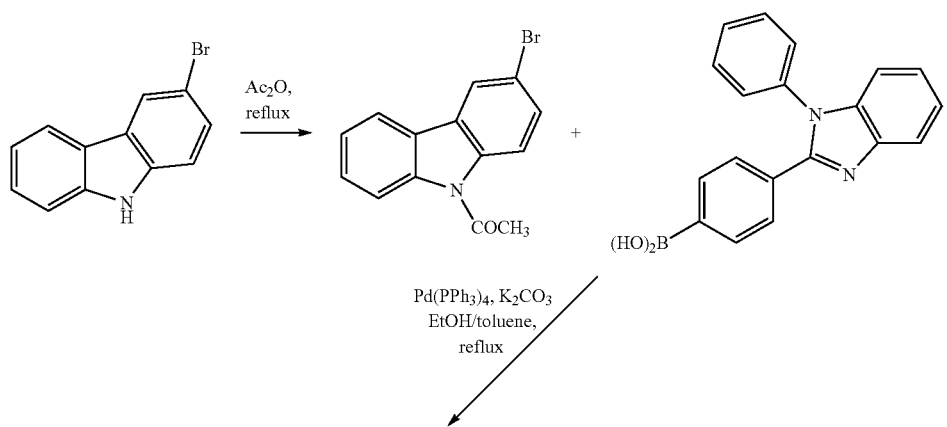

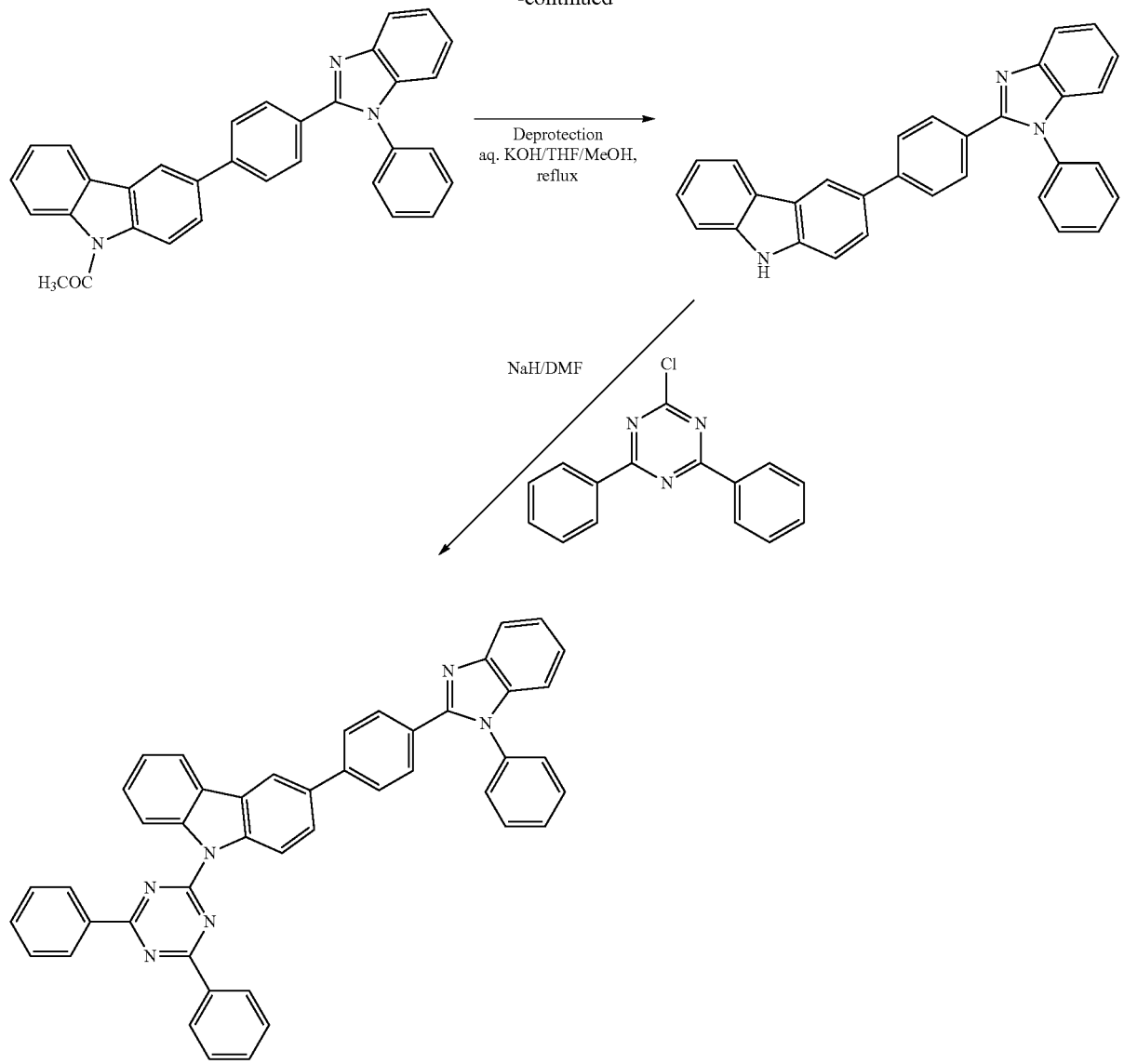
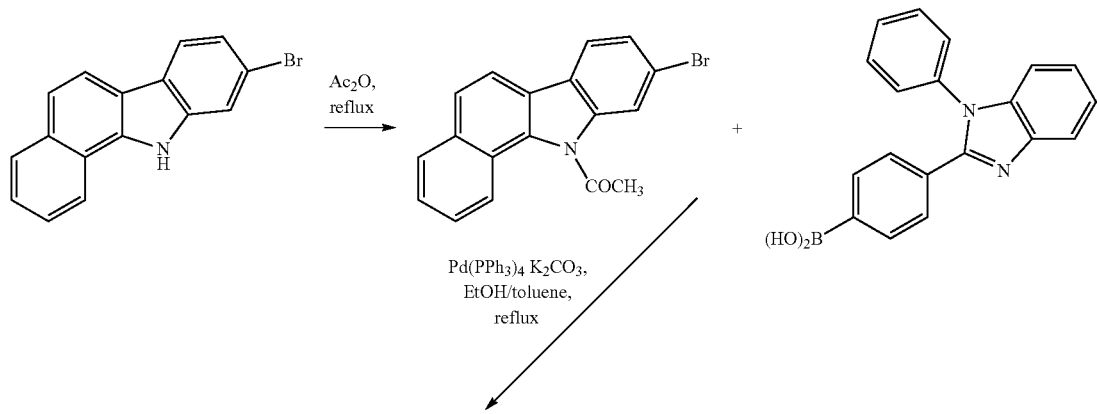
Scheme 2

51   52
-continued
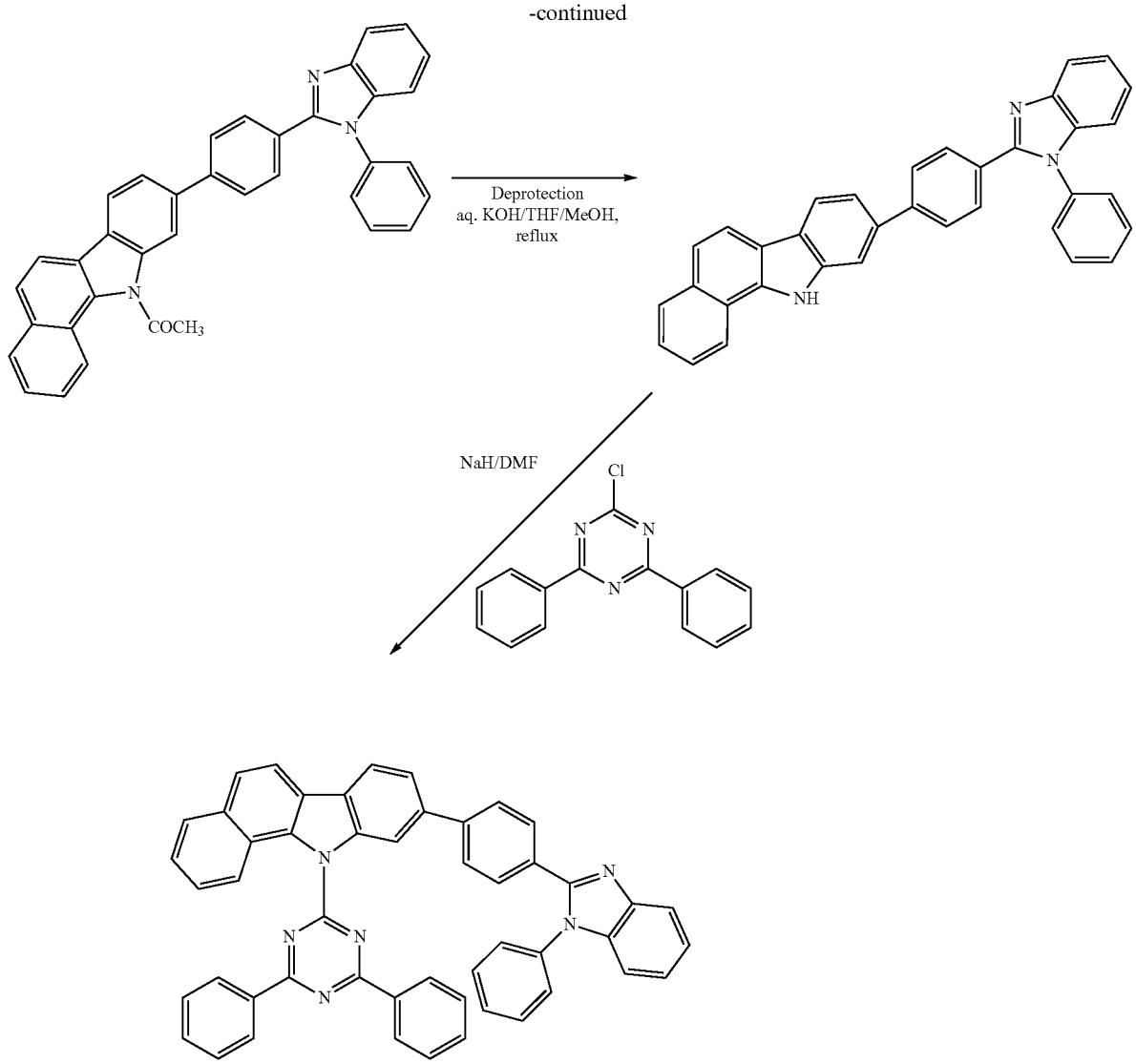
Scheme 3
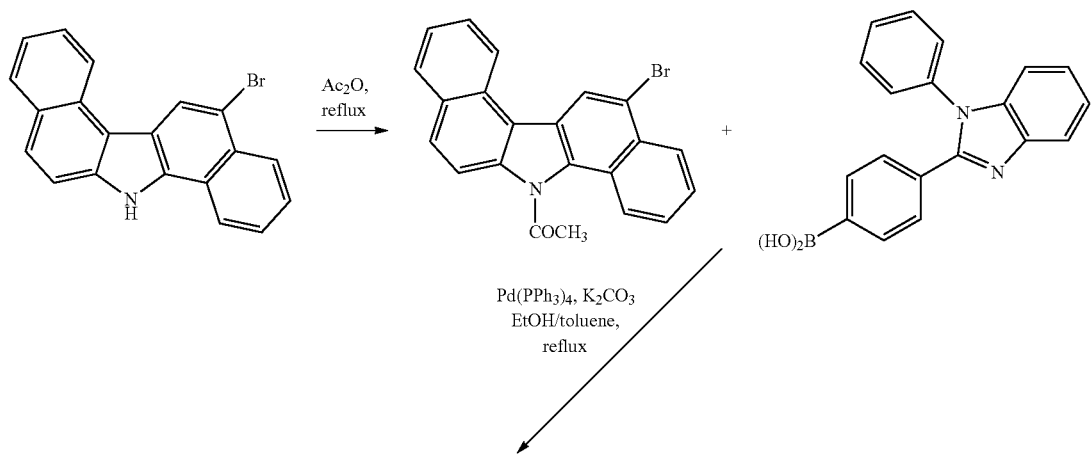

53 54
-continued
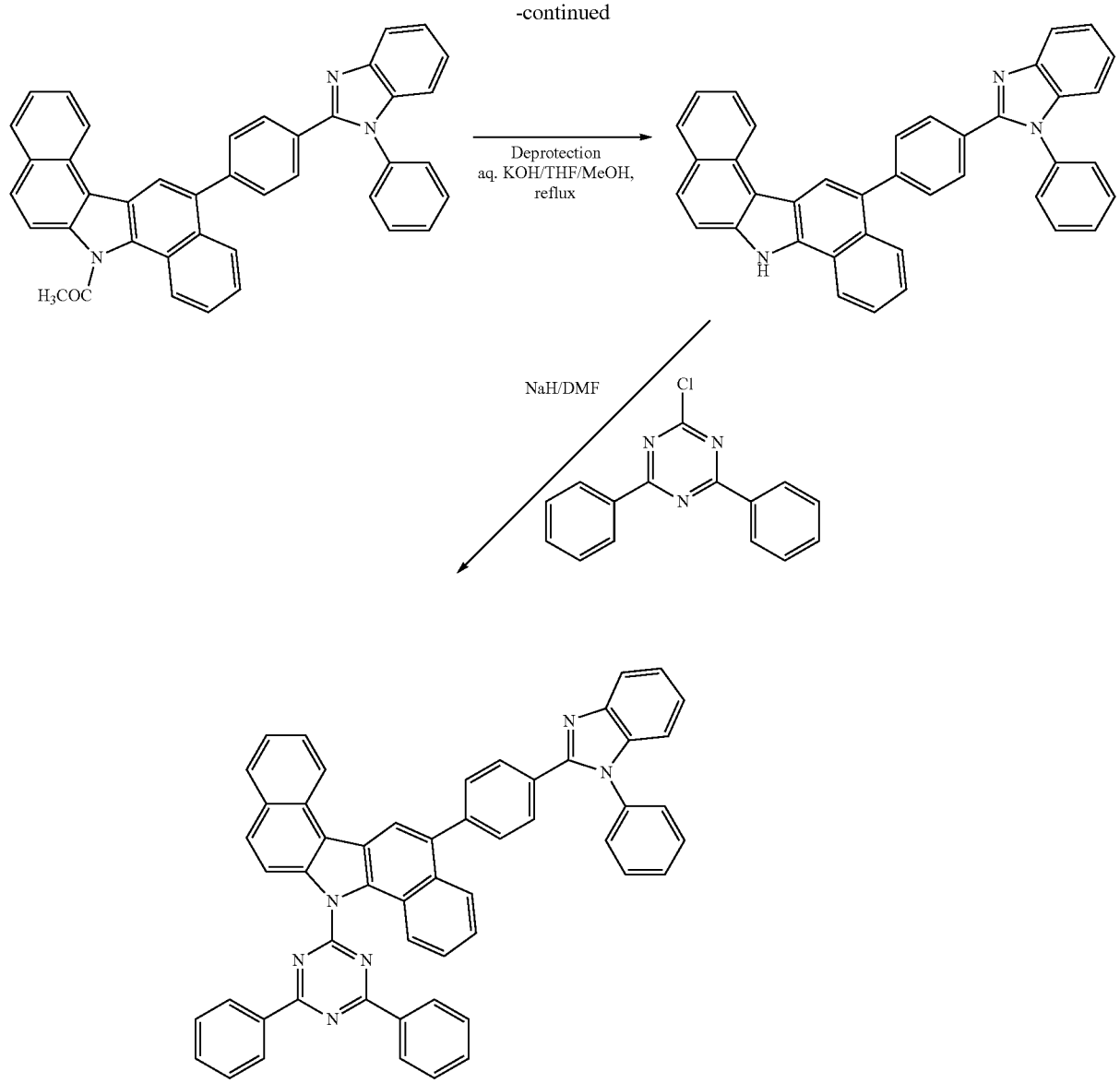
Scheme 4
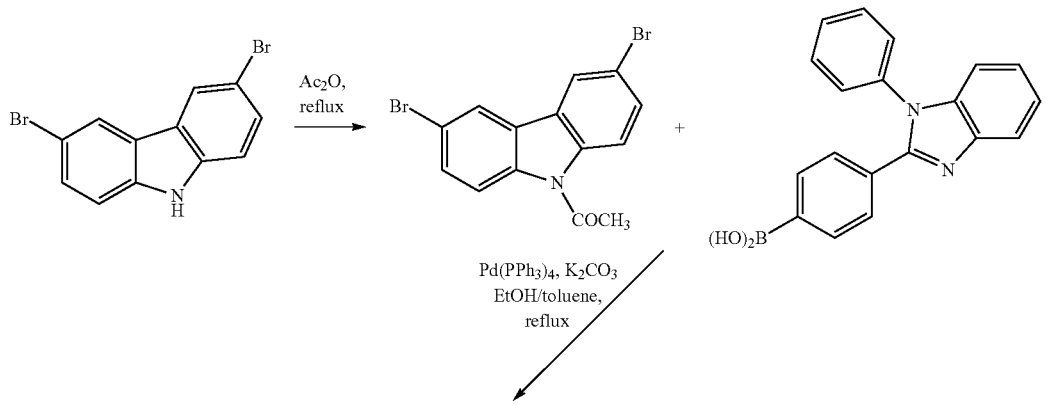

-continued
55
56
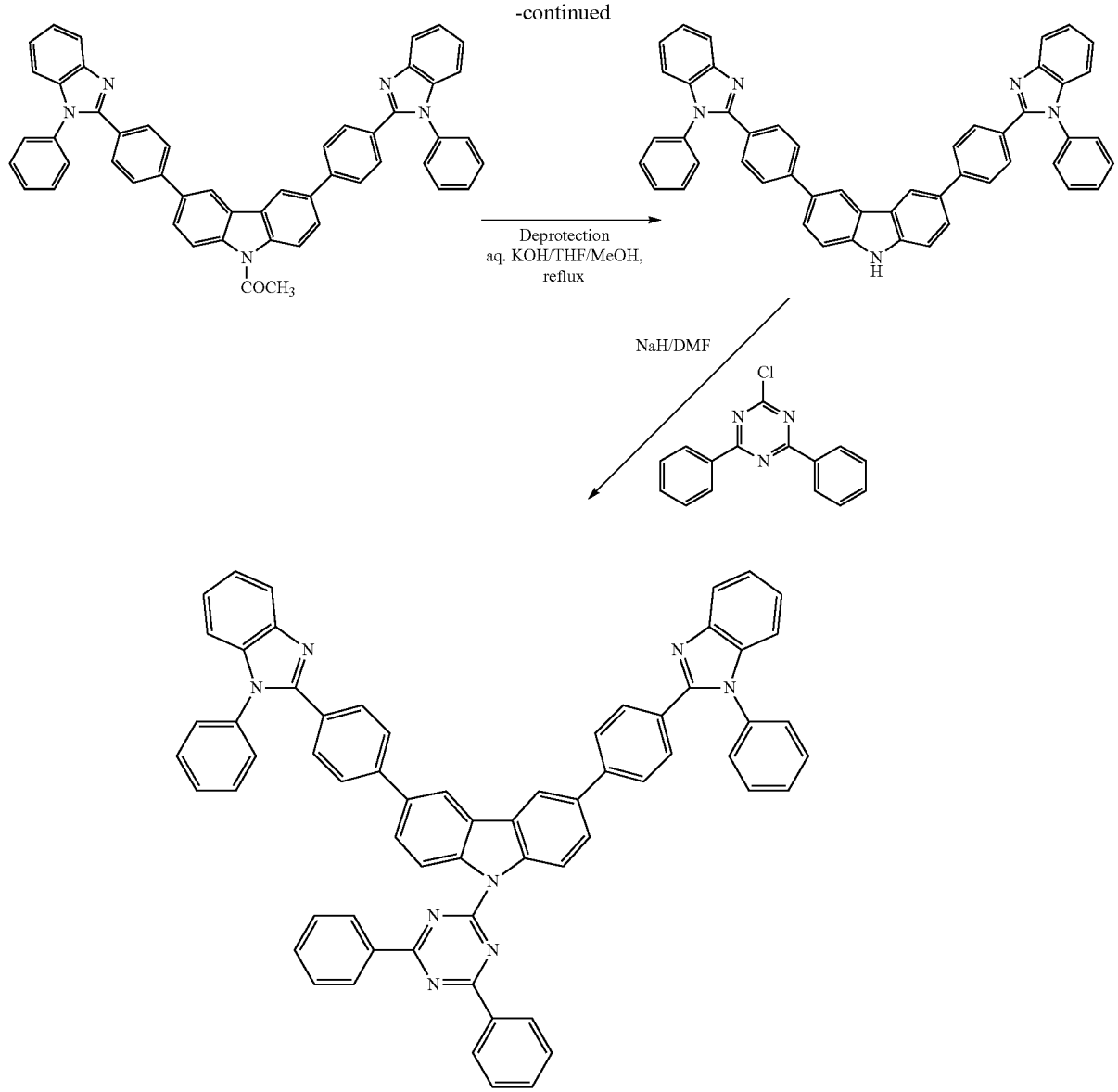
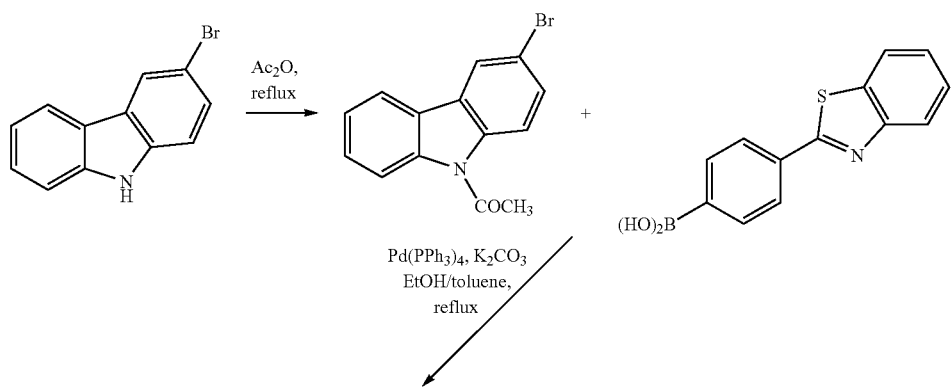
Scheme 5

-continued
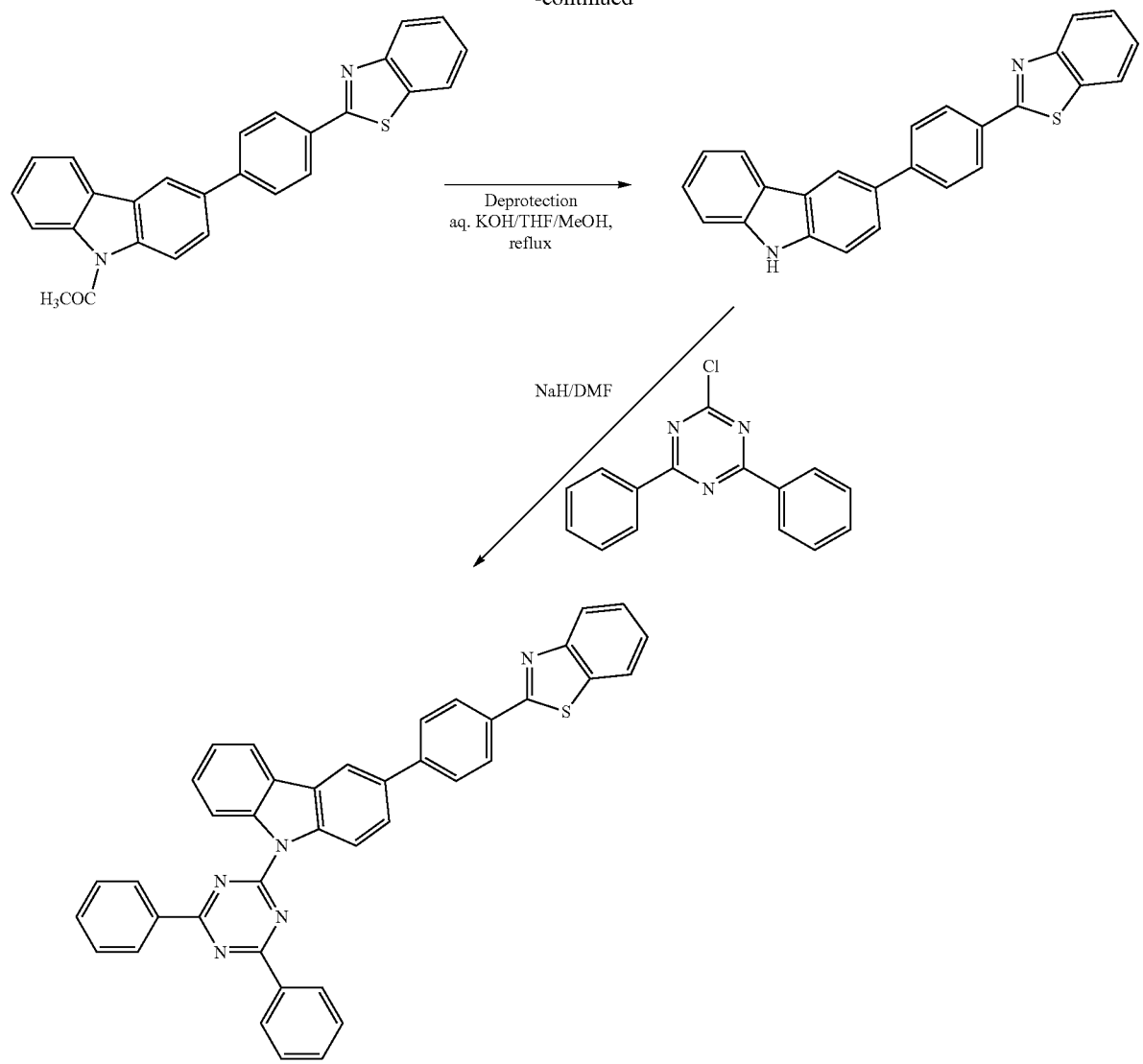
Scheme 6
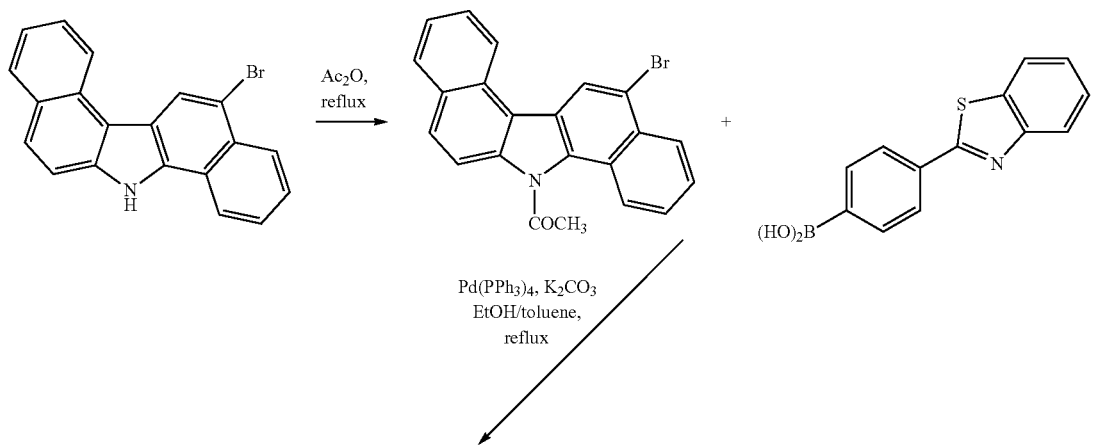

-continued
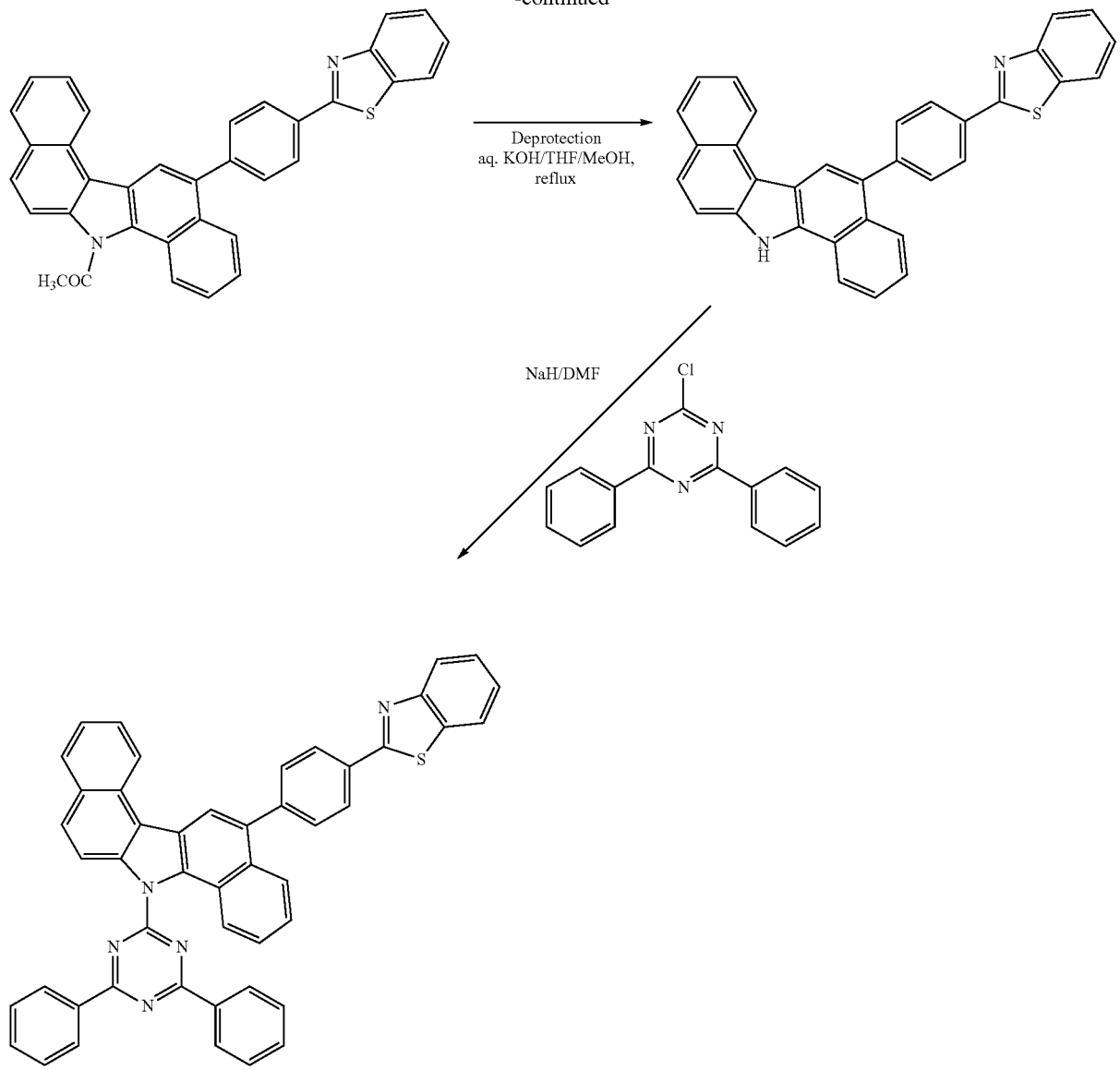
Scheme 7
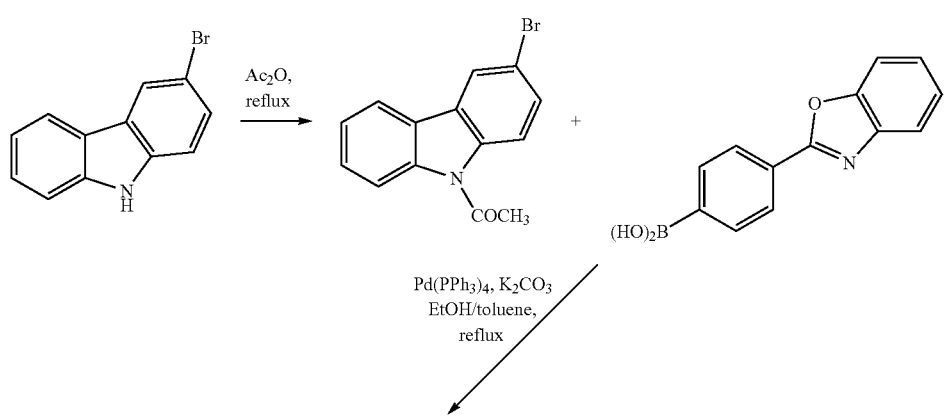

-continued
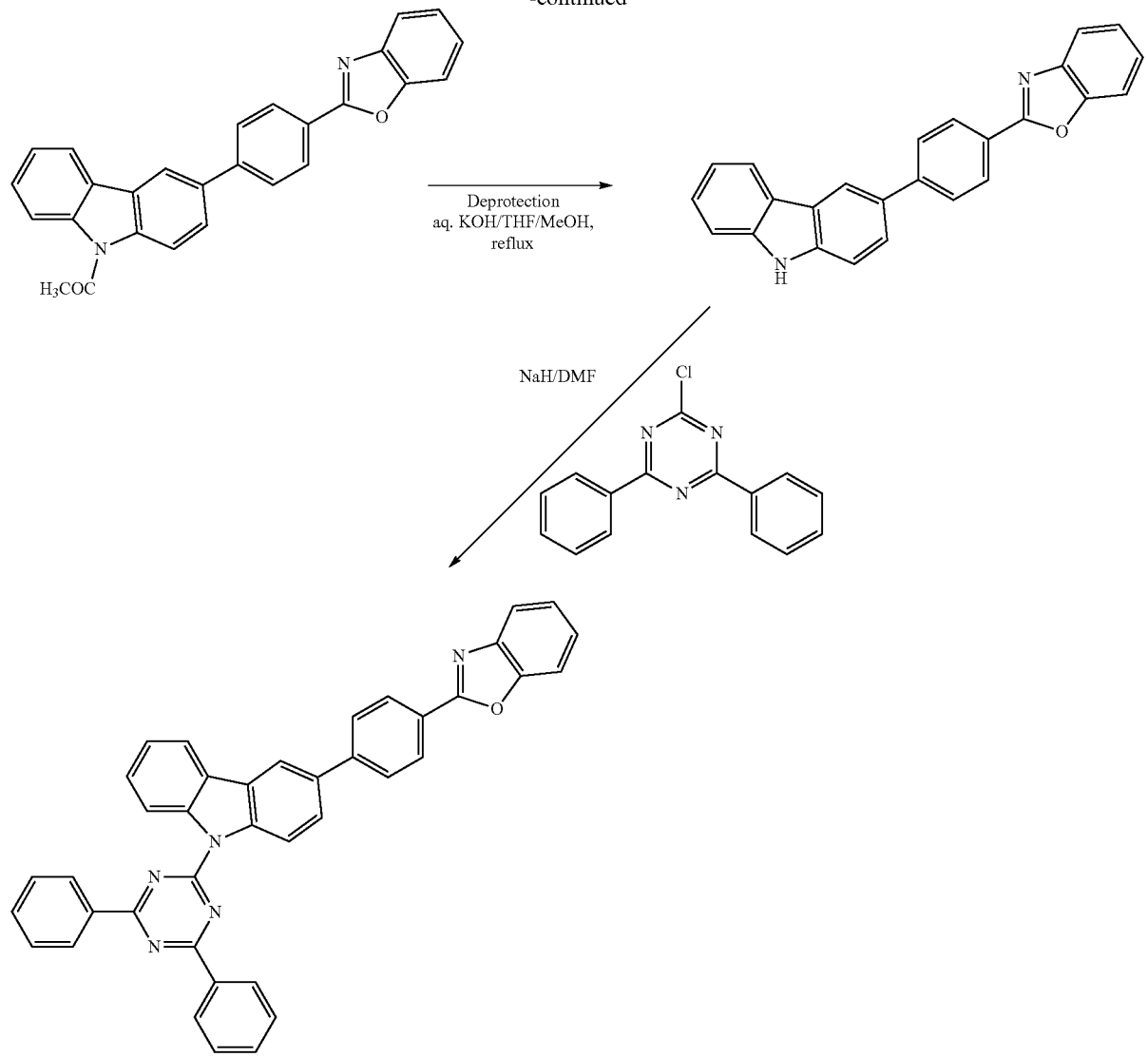
Scheme 8
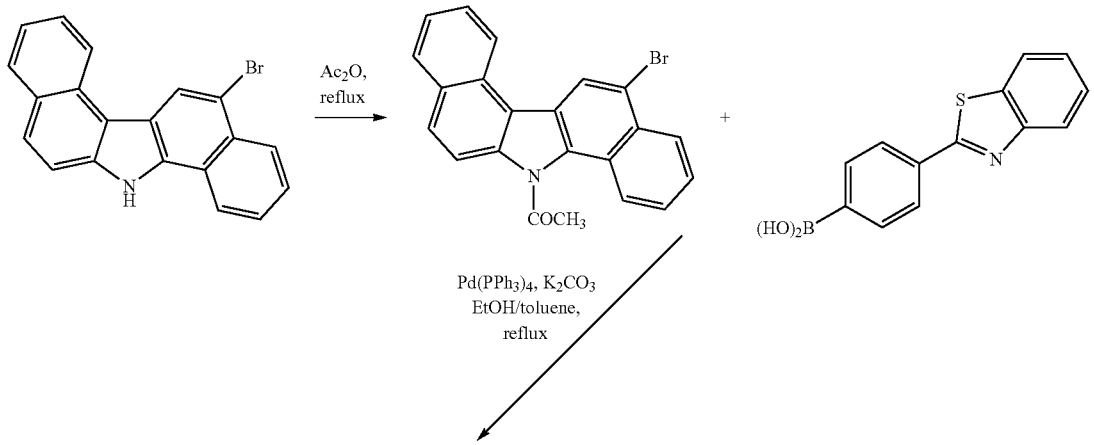

-continued

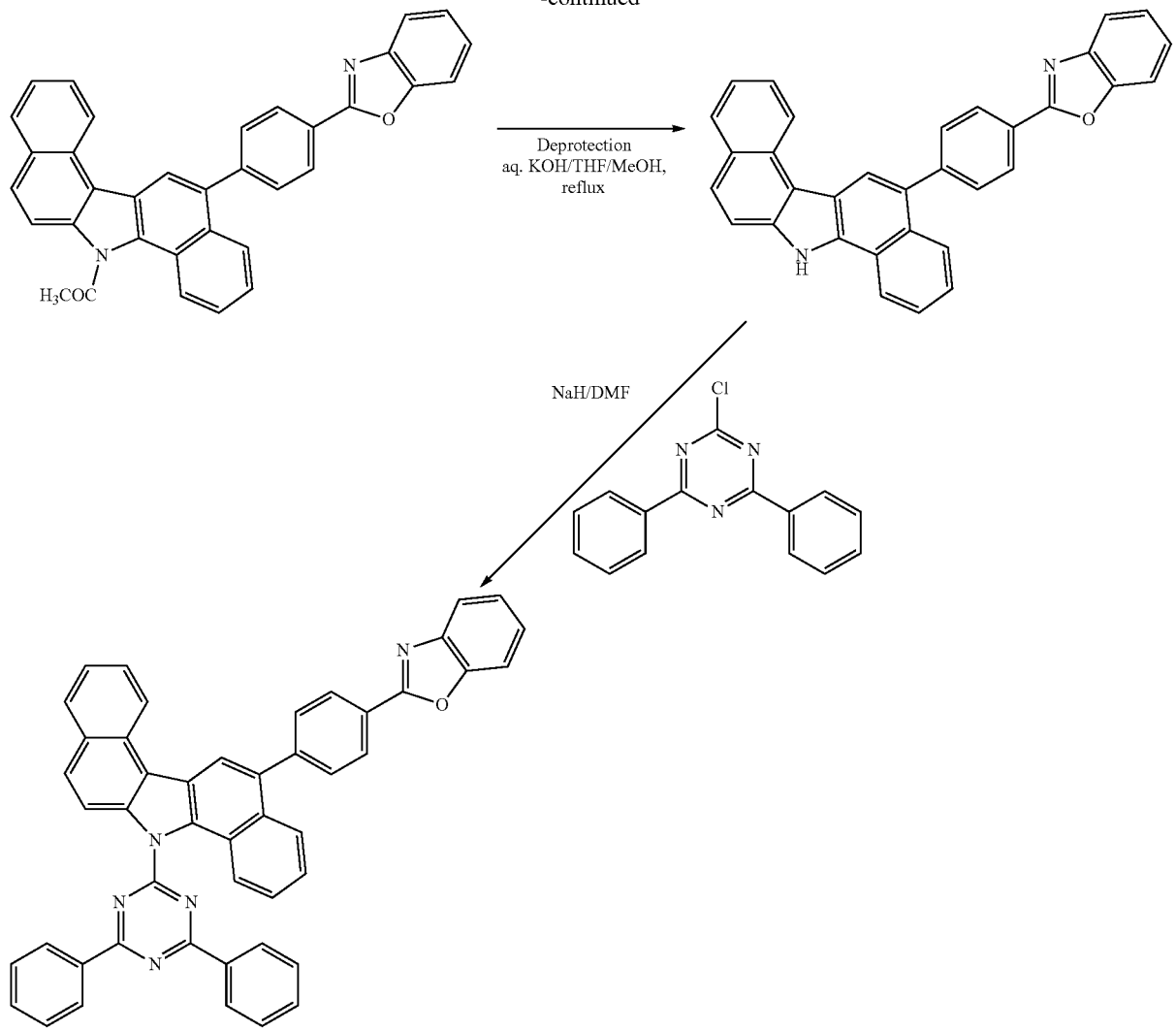

Specific examples of 2-chloro-4,6-diaryltriazines used in the preparation of the above-said compounds represented by the general formulae (I) can be readily prepared by known methods described in J. Org. Chem, 1969, No. 34, p. 4125; and Chem. Ztg, 1912, No. 36, p. 738.

Specific examples of halogen-substituted aryl benzimidazoles, benzothiazoles and benzoxazoles and their corresponding boronic acids or boronate esters, may be prepared by the synthetic procedures described by Ziyi et al in Advanced Functional Material 2008, No. 18, p. 584 and in the patent literature WO 2009126691.

Various substituted derivatives of carbazole, benzocarbazole and naphthocarbazole intermediates shown in the above schemes that are used in the synthesis of the compounds of the present invention represented by general formula (I) may be prepared by the procedures known in the literature cited elsewhere.

The compound represented by formula (I) as previously described may be included in an organic layer of an organic electroluminescent device (EL), according to the embodiment of the present invention. Therefore the organic electroluminescent device of the present invention has at least one organic layer disposed between an anode and a cathode piled one upon another on a substrate wherein the organic layer includes the aforementioned compound represented by the formula (I) as described earlier. Here the organic layer may be an emitting layer, a hole bock layer, an electron transporting layer or electron injection layer or a hole transporting layer. The organic layer including the compound represented by the formula (I) may preferably be included in the electron transport/injection layer and in combination with electrically injecting dopants (n/p type).

Electrically conducting (n/p type) dopants to be used in the electron transporting layer are preferably organic alkali/alkaline metal complexes, oxides, halides, carbonates, phosphates of alkali/alkaline group metals containing at least one metal selected from lithium, cesium or oxides of molybdenum and tungsten. Such organic metal complexes are known in the aforementioned patent documents and elsewhere and a suitable complex can be selected from them and used in this invention.

The content of the aforementioned electrically injecting dopant in the electron transport/electron injection layer is preferably in the range of 25 wt % to 75 wt %.

Further, the compound represented by any of formula (I) may be included in the layer between emitting layer and electron transporting layer. The emitting layer may include fluorescent and phosphorescent dopants and the corresponding fluorescent and phosphorescent host emitters, respectively.

Preferred Embodiments of the Invention

The structure of the organic EL device of this invention will be explained with reference to the drawing, but not limited thereto.

FIG. 1 which illustrates an embodiment, is a schematic showing an organic light emitting device 100. Device 100 may include a substrate 110, an anode 120, a hole injection layer 130, a hole transporting layer 140, an emissive layer 150, an electron transporting layer 160, an electron injection layer 170, and a cathode 180. Device 100 may be fabricated by depositing the layers described, in order.

Figure 2:
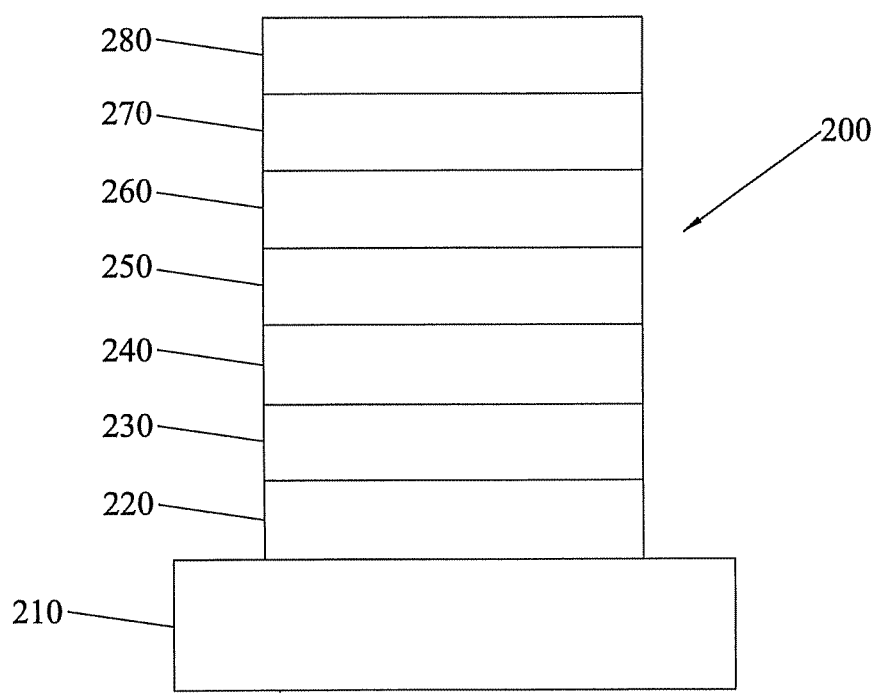
FIG. 2 is a cross-sectional view illustrating another example of an organic light emitting device according to another embodiment of the present invention.
Figure 3:
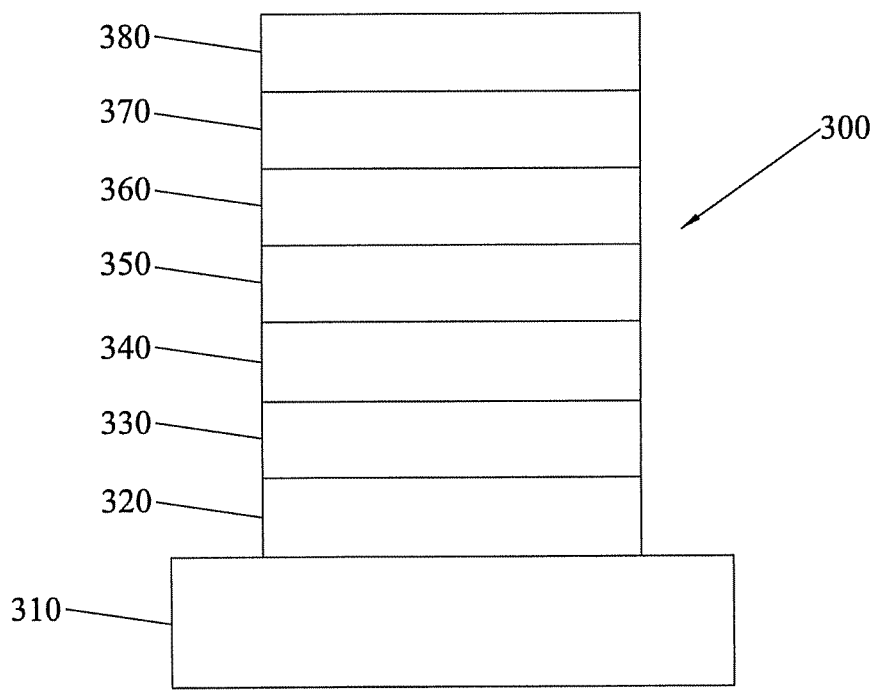
FIG. 3 is a cross-sectional view illustrating yet another example of an organic light emitting device according to another embodiment of the present invention.

FIG. 2 which illustrates an embodiment is a schematic showing an organic light emitting device 200. Device 200 may include a substrate 210, an anode 220, a hole injection layer 230, a hole transporting layer 240, an excition blocking layer 245, an emissive layer 250, an electron transporting layer 260, an electron injection layer 270, and a cathode 280;

FIG. 3 which illustrates an embodiment is a schematic showing an organic light emitting device 300. Device 300 may include a substrate 310, an anode 320, a hole injection layer 330, a hole transporting layer 340, an emissive layer 350, an exciton blocking layer 355, an electron transporting layer 360, an electron injection layer 370, and a cathode 380;

It is possible to fabricate a device with a structure that is the reverse of the one shown in FIG. 1-3. In this case of the reverse structure, a layer or layers may be added or omitted as needed. Materials used in hole injection layer, hole transporting layer, electron blocking layer, hole blocking layer, emitting layer may be selected from those reported in the literature cited elsewhere.

For example, an electron-transporting material forming the electron-transporting layer differs from the material forming the light emitting layer and has hole-transporting properties, so as to facilitate the hole mobility in the electron-transporting layer, and to prevent accumulation due to the difference in ionization potential between the light emitting layer and the electron-transporting layer can be prevented.

In addition, U.S. Pat. No. 5,844,363, which is incorporated by reference in its entirety, discloses a flexible and transparent substrate-anode combination. An example of a p-doped hole transporting layer is m-MTDATA doped with $F_4$-TCNQ at a molar ratio of 50:1, as disclosed in US Patent Application Publication No. 20030230980, which is incorporated by reference in its entirety. An example of an n-doped electron transporting layer is BPhen doped with Li at a molar ratio of 1:1, as disclosed in US Patent Application Publication No. 20030230980, which is incorporated by reference in its entirety. US Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in U.S. Pat. No. 6,097,147 and US Patent Application Publication No. 20030230980, which are incorporated by reference in their entireties. Examples of injection layers are provided in US Patent Application Publication No. 20040174116, which is incorporated by reference in its entirety. A description of protective layers may be found in US Patent Application Publication No. 20040174116, which is incorporated by reference in its entirety.

Structures and materials not specifically described may also be used, such as OLEDs comprised of polymeric materials (PLEDs) such as disclosed in U.S. Pat. No. 5,247,190, which is incorporated by reference in its entirety. Further, OLEDs having a single organic layer may be used. OLEDs may be stacked as described in U.S. Pat. No. 5,707,745, which is incorporated by reference in its entirety.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102, which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with deposition methods such as ink-jet and OVJD. Certainly, other methods may be used. The materials to be deposited may be modified to make them compatible with a particular deposition method.

Organic EL device of this invention is applicable to a single device, a device with its structure arranged in array, or a device in which the anode and the cathode are arranged in a X-Y matrix. The organic EL device of this invention produces significant improvement in lifetime stability over the conventional devices, when used as an electron transporting/injecting layer, in combination with n-type dopants, for both fluorescent or phosphorescent OLED device structures, and furthermore the organic electroluminescent device of the present invention can perform better when applied to monochrome, full-color, multicolor panels for both display and lighting applications.

EXAMPLES

This invention will be described in more detail below with reference to the examples; however, it will not be limited to these examples and it can be reduced to practice in various modes unless such practice exceeds the substance of this invention.

9-acetyl-3-bromocarbazole 20 g of 3-bromocarbazole was converted to its acetyl derivative by refluxing with acetic anhydride (3 vol) with traces of conc. sulfuric acid. Aqueous workup yielded an off-white solid, which was then washed with n-hexane and dried under vacuum to obtain 23 g 9-acetyl-3-bromocarbazole, quantitatively. And N-acetyl derivative of carbazole, benzocarbaole and dibenzocarbazoles were prepared following the same procedure.

9-bromo-11H-benzo[a]carbazole 9-bromo-11H-benzo[a]carbazole was synthesized according to the procedures given in *J. Med. Chem.*, 1986, 29 (3), p 380.

12-bromo-7H-dibenzo[a,g]carbazole 10.3 g of 7H-dibenzo[a,g]carbazole was dissolved in dichloromethane (150 mL) at 0° C. with stirring. To this was dropped a dichloromethane solution of bromine (3.1 g in dichloromethane). After being stirred at room temperature for 2 h, the solution was poured into 200 mL of water, filtered, and washed with 500 mL water. The white residue was recrystallized in ethanol and yielded 12-bromo-7H-dibenzo[a,g]carbazole as colorless crystals (10.8 g).

3,6-dibromocarbazole 3,6-dibromocarbazole was synthesized according to the procedures given in *Macromol. Chem. Phys.* 1994, 195, p 2353.

Synthesis Example 1

Synthesis of Compound 1-17

A mixture of 5.8 g of 9-Acetyl-3-bromoocarbazole and 14.0 g of 4-(1-phenyl-1H-benzo [d]imidazol-2-yl) phenylboronic acid were stirred together in 30 ml of toluene. To this was added 0.02 g of tetrakis (triphenylphosphine) palladium, 6.9 g of potassium carbonate and 10 ml of aqueous ethanol were added and refluxed under nitrogen for 6 h. The reaction was quenched with water and the toluene layer was removed and passed through a celite column.

The organic layers were combined and then evaporated in a rotary evaporator under vacuum to yield 8.3 g of 9-acetyl-3-[4-(1-phenyl-1H-benzo [d]imidazol-2-yl) phenyl]-9H-carbazole as a white solid.

The solid (8.3 g) was then taken up for further deprotection using 1.0 g KOH with THF (20 ml), methanol (10 ml) and water (6 ml) at reflux temperature. The reaction mixture was then extracted using ethyl acetate; the organic layer was dried over anhydrous sodium sulfate and evaporated to dryness under vacuum. Subsequent silica gel column chromatography using toluene:hexane (1:2) as eluent, yielded 8.0 g of 3-[4-(1-phenyl-1H-benzo [d]imidazol-2-yl) phenyl]-9H-carbazole.

Dissolved the above obtained 3-[4-(1-phenyl-1H-benzo[d]imidazol-2-yl) phenyl]-9H-carbazole (8.0 g) in 50 ml of dry N,N'-dimethylformamide under nitrogen. Added 0.9 g of sodium hydride and stirred at room temperature for 1 h. A solution of 2-chloro-4,6-diphenyl-1,3,5-triazine (6.0 g) in dry N,N'-dimethylformamide (20 ml) was then added to the reaction mixture. The reaction was further allowed to stir for another 3 h. The product was precipitated by pouring the reaction mixture into water. The solid thus obtained was then washed with methanol and dried under vacuum to obtain 8.5 g of 9-(4,6-diphenyl-1,3,5-triazin-2-yl)-3-[4-(1-phenyl-1H-benzo[d]imidazol-2-yl)phenyl]-9H-carbazole, compound 1-17 (72%).

Figure 10:
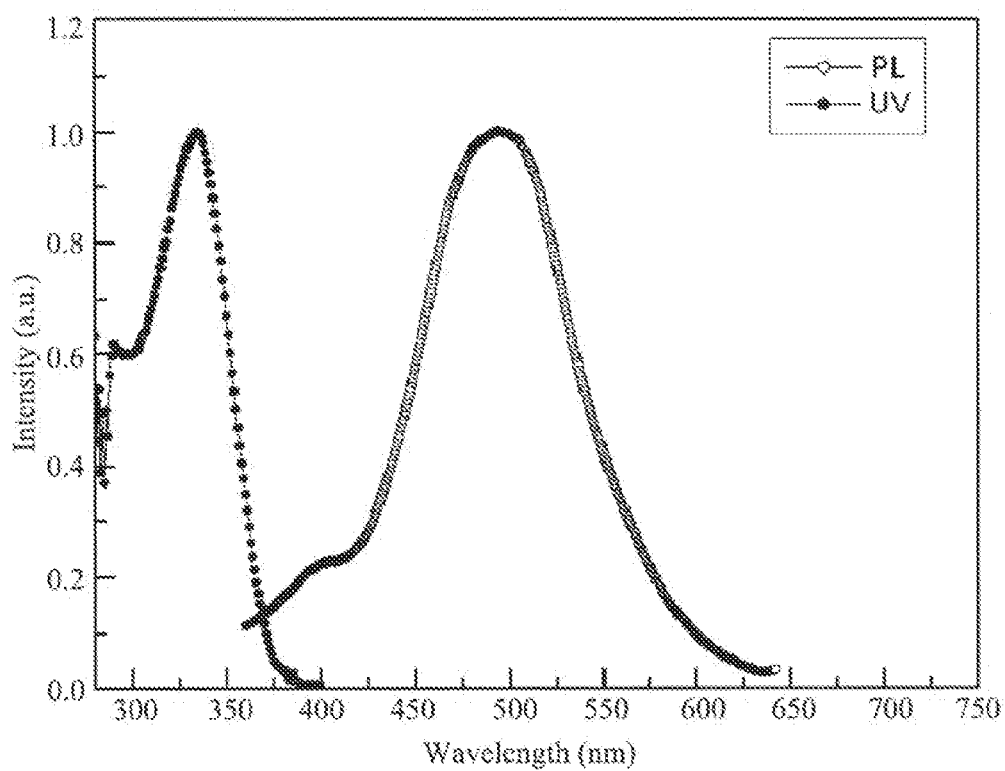
FIG. 10 shows the UV absorption spectrum and photoluminescence spectrum of compound No. 1-17 according to the present invention.

Compound 1-17 showed a melting point of 296° C. and a glass transition temperature of 141° C. UV Absorption and the photoluminescence spectra are shown in FIG. 10.

Figure 4:
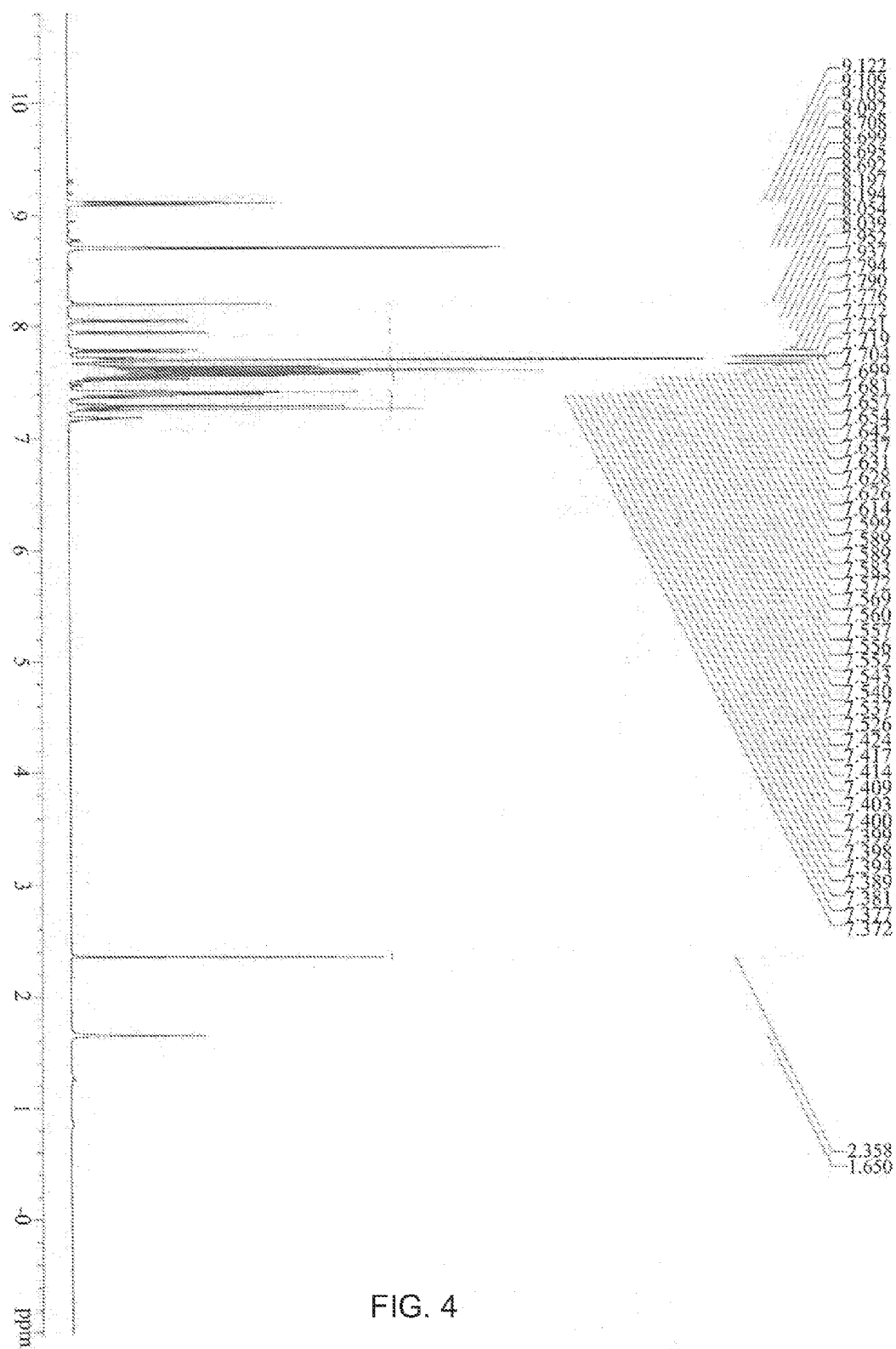
FIG. 4 shows the $^1$H-NMR spectrum of the compound No. 1-17 according to the present invention.

$^1$H-NMR is shown in FIG. 4.

$^1$H NMR (CDCl3, δ): 9.12 (dd, 2H); 8.70 (dd, 4H); 8.20 (d, 1H); 8.05 (d, 1H); 7.95 (d, 1H); 7.79 (d, 1H); 7.72 (m, 5H); 7.70 (m, 8H); 7.54 (m, 3H); 7.42 (m, 3H); 7.39 (m, 3H); 7.37 (m, 1H).

Synthesis Example 2

Synthesis of Compound 1-26

Following the above procedure, Suzuki coupling of 6.7 g of 9-bromo-11-acetyl-11H-benzo[a]carbazole and 14.0 g of 4-(1-phenyl-1H-benzo [d]imidazol-2-yl) phenylboronic acid were stirred together in 30 ml of toluene. To this was added 0.02 g of tetrakis(triphenylphosphine)palladium, 6.9 g of potassium carbonate and 10 ml of aqueous ethanol were added and refluxed under nitrogen for 6 h. The reaction was quenched with water and the toluene layer was removed and passed through a celite column. The organic layers were combined and then evaporated in a rotary evaporator under vacuum to yield 9.5 g of 11-acetyl-3-[4-(1-phenyl-1H-benzo[d] imidazol-2-yl) phenyl]-11H-benzocarbazole as a white solid.

The solid (9.5 g) was then taken up for further deprotection using 1.0 g KOH with THF (20 ml), methanol (10 ml) and water (6 ml) at reflux temperature. The reaction mixture was then extracted using ethyl acetate; the organic layer was dried over anhydrous sodium sulfate and evaporated to dryness under vacuum. Subsequent silica gel column chromatography using toluene:hexane (1:2) as eluent, yielded 9.0 g of 3-[4-(1-phenyl-1H-benzo [d]imidazol-2-yl) phenyl]-11H-benzocarbazole Dissolved the above obtained 3-[4-(1-phenyl-1H-benzo[d]imidazol-2-yl) phenyl]-11H-benzo carbazole (9.0 g) in 50 ml of dry N,N'-dimethylformamide under nitrogen. Added 1.0 g of sodium hydride and stirred at room temperature for 1 h. A solution of 2-chloro-4,6-diphenyl-1,3,5-triazine (6.0 g) in dry N,N'-dimethylformamide (20 ml) was then added to the reaction mixture. The reaction was further allowed to stir for another 3 h. The product was precipitated by pouring the reaction mixture into water. The solid thus obtained was then washed with methanol and dried under vacuum to obtain 11.0 g of 11-(4,6-diphenyl-1,3,5-triazin-2-yl)-2-[4-(1-phenyl-1H-benzo[d]imidazol-2-yl)phenyl]-11H-benzo[a]carbazole, compound 1-26 (84%).

Figure 11:
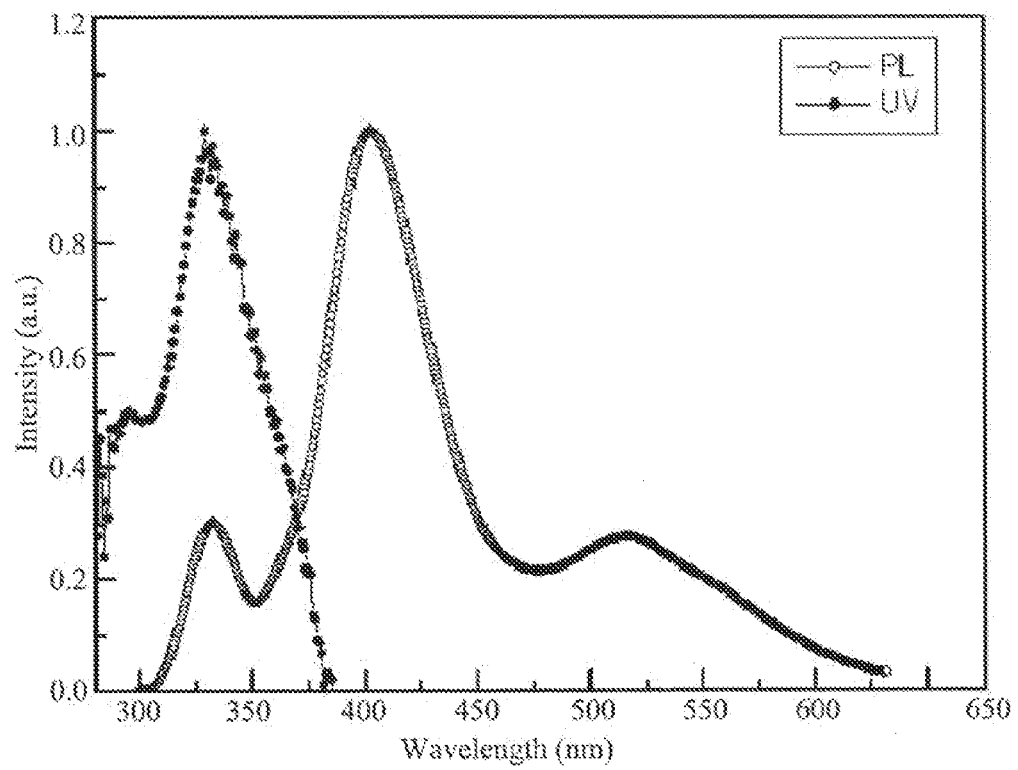
FIG. 11 shows the UV absorption spectrum and photoluminescence spectrum of compound No. 1-26 according to the present invention.

Compound 1-26 showed a melting point of 310° C. UV Absorption and the photoluminescence spectra is shown in FIG. 11.

Figure 5:
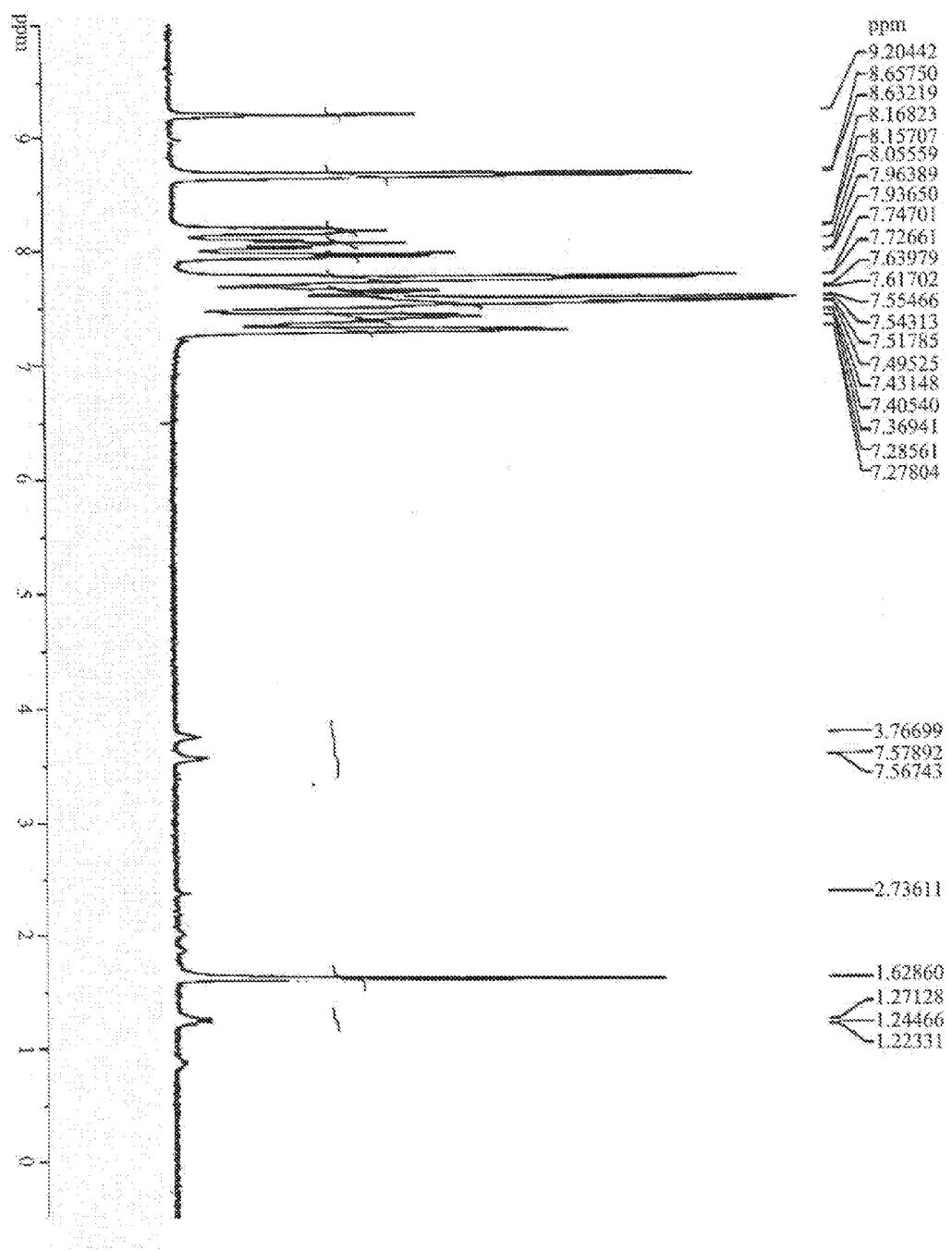
FIG. 5 shows the $^1$H-NMR spectrum of the compound No. 1-26 according to the present invention.

$^1$H-NMR is shown in FIG. 5

$^1$H NMR (CDCl3, δ): 9.20 (s, 1H); 8.65 (dd, 4H); 8.17 (m, 2H); 8.06 (t, 2H); 7.96 (d, 2H); 7.74 (m, 5H); 7.55 (m, 10H); 7.43 (m, 4H); 7.28 (m, 2H).

Synthesis Example 3

Synthesis of Compound 1-11

Following the above procedure, Suzuki coupling of 3.4 g of 7-acetyl-12-bromo-7H-dibenzo [a,g]carbazole and 3.8 g of 4-(1-phenyl-1H-benzo [d]imidazol-2-yl) phenylboronic acid were stirred together in 30 ml of toluene. To this was added 0.01 g of tetrakis(triphenylphosphine)palladium, 2.7 g of potassium carbonate and 10 ml of aqueous ethanol were added and refluxed under nitrogen for 6 h. The reaction was quenched with water and the toluene layer was removed and passed through a celite column. The organic layers were combined and then evaporated in a rotary evaporator under vacuum to yield 4.6 g of 7-acetyl-12-[4-(1-phenyl-1H-benzo [d]imidazol-2-yl)phenyl]-7H-dibenzo [a,g]carbazole as a white solid.

The solid (4.6 g) was then taken up for further deprotection using 0.5 g KOH with THF (20 ml), methanol (10 ml) and water (6 ml) at reflux temperature. The reaction mixture was then extracted using ethyl acetate; the organic layer was dried over anhydrous sodium sulfate and evaporated to dryness under vacuum. Subsequent silica gel column chromatography using toluene:hexane (1:2) as eluent, yielded 4.3 g of 12-[4-(1-phenyl-1H-benzo [d]imidazol-2-yl) phenyl]-7H-dibenzo[a,g]carbazole.

Dissolved the above obtained 12-[4-(1-phenyl-1H-benzo[d]imidazol-2-yl)phenyl]-7H-dibenzo[a,g]carbazole (4.3 g) in 50 ml of dry N,N'-dimethylformamide under nitrogen. Added 0.5 g of sodium hydride and stirred at room temperature for 1 h. A solution of 2-chloro-4,6-diphenyl-1,3,5-triazine (3.0 g) in dry N,N'-dimethylformamide (20 ml) was then added to the reaction mixture. The reaction was further allowed to stir for another 3 h. The product was precipitated by pouring the reaction mixture into water. The solid thus obtained was then washed with methanol and dried under vacuum to obtain 5.0 g of 7-(4,6-diphenyl-1,3,5-trazin-2-yl)-12-[4-(1-phenyl-1H-benzo[d]imidazol-2-yl)phenyl] -7H-dibenzo[a,g]carbazole, compound 1-11 (81%).

Compound 1-11 showed a melting point of 356° C.

Figure 6:
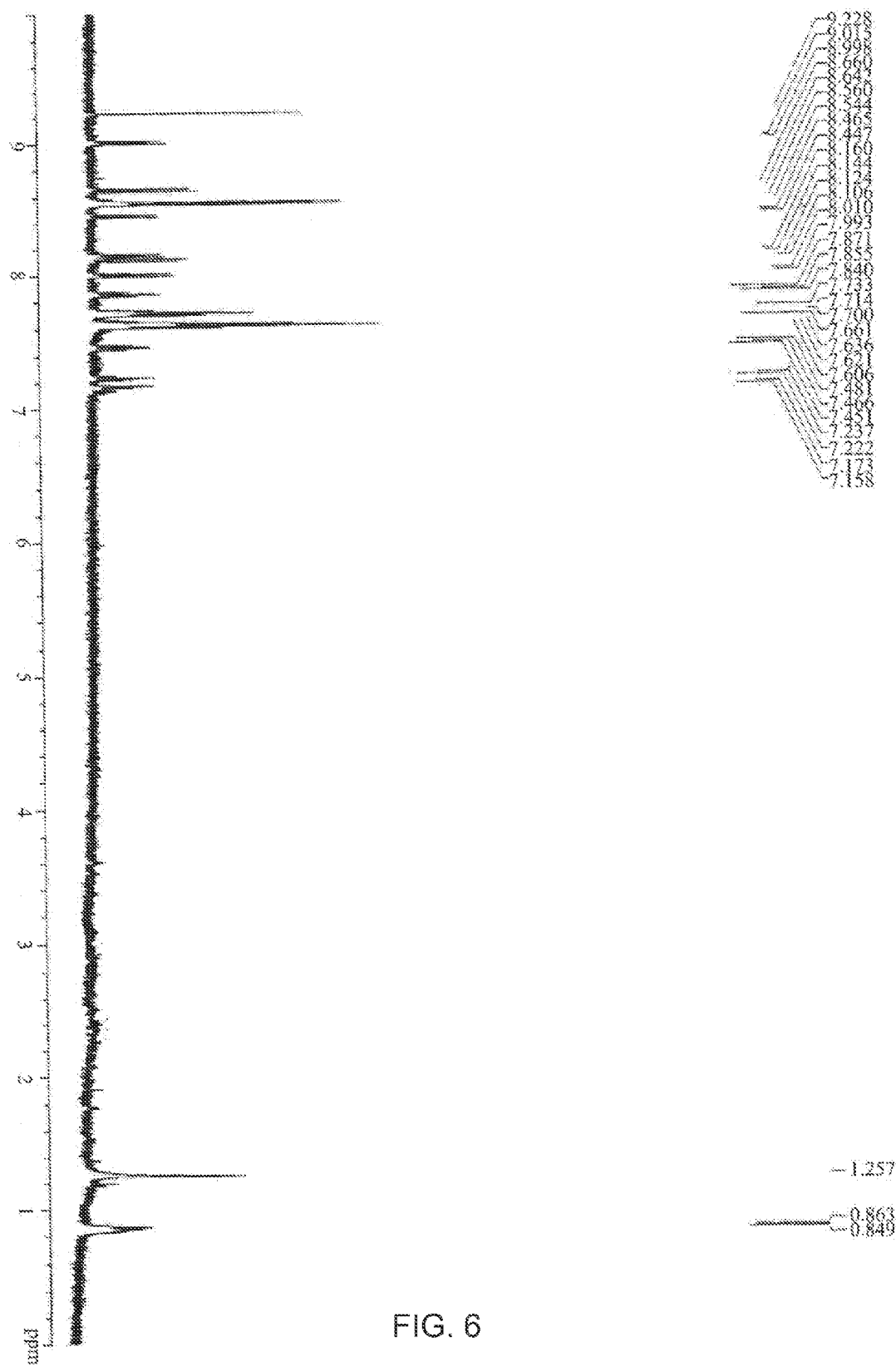
FIG. 6 shows the $^1$H-NMR spectrum of the compound No. 1-11 according to the present invention.

$^1$H-NMR is shown in FIG. 6

$^1$H NMR (CDCl3, δ): 9.23 (s, 1H); 9.01 (d, 2H); 8.66 (d, 2H); 8.56 (d, 4H); 8.46 (d, 2H); 8.16 (m, 4H); 8.01 (d, 2H); 7.87 (t, 3H); 7.73 (m, 3H); 7.63 (m, 5H); 7.48 (t, 2H); 7.23 (m, 2H); 7.17 (m, 2H).

Synthesis Example 4

Synthesis of Compound 1-35

Following the above procedure, Suzuki coupling of 7.4 g of 9-Acetyl-3,6-dibromocarbazole and 14.0 g of 4-(1-phenyl-1H-benzo [d]imidazol-2-yl) phenylboronic acid were stirred together in 30 ml of toluene. To this was added 0.03 g of tetrakis(triphenylphosphine)palladium, 7.0 g of potassium carbonate and 10 ml of aqueous ethanol were added and refluxed under nitrogen for 6 h. The reaction was quenched with water and the toluene layer was removed and passed through a celite column. The organic layers were combined and then evaporated in a rotary evaporator under vacuum to yield 10.5 g of 9-acetyl-3,6-bis[4-(1-phenyl-1H-benzo[d]imidazol-2-yl) phenyl]-9H-carbazole as a white solid.

The solid (10.5 g) was then taken up for further deprotection using 2.0 g KOH with THF (40 ml), methanol (20 ml) and water (12 ml) at reflux temperature. The reaction mixture was then extracted using ethyl acetate; the organic layer was dried over anhydrous sodium sulfate and evaporated to dryness under vacuum. Subsequent silica gel column chromatography using toluene:hexane (1:2) as eluent, yielded 9.0 g of 3,6-bis[4-(1-phenyl-1H-benzo[d]imidazole-2-yl)phenyl]-9H-carbazole.

Dissolved the above obtained 3,6-bis([-(1-phenyl-1H-benzo[d]imidazole-2-yl)phenyl]-9H-carbazole (9.0 g) in 50 ml of dry N,N'-dimethylformamide under nitrogen. Added 1.0 g of sodium hydride and stirred at room temperature for 1 h. A solution of 2-chloro-4,6-diphenyl-1,3,5-triazine (6.0 g) in dry N,N'-dimethylformamide (20 ml) was then added to the reaction mixture. The reaction was further allowed to stir for another 3 h. The product was precipitated by pouring the reaction mixture into water. The solid thus obtained was then washed with methanol and dried under vacuum to obtain 9.8 g of 9-(4,6-diphenyl-1,3,5-trazin-2-yl)-3,6-bis[4-(1-phenyl-1H-benzo[d]imidazol-2-yl)phenyl]-9H-carbazole, compound 1-35 (82%).

Figure 12:
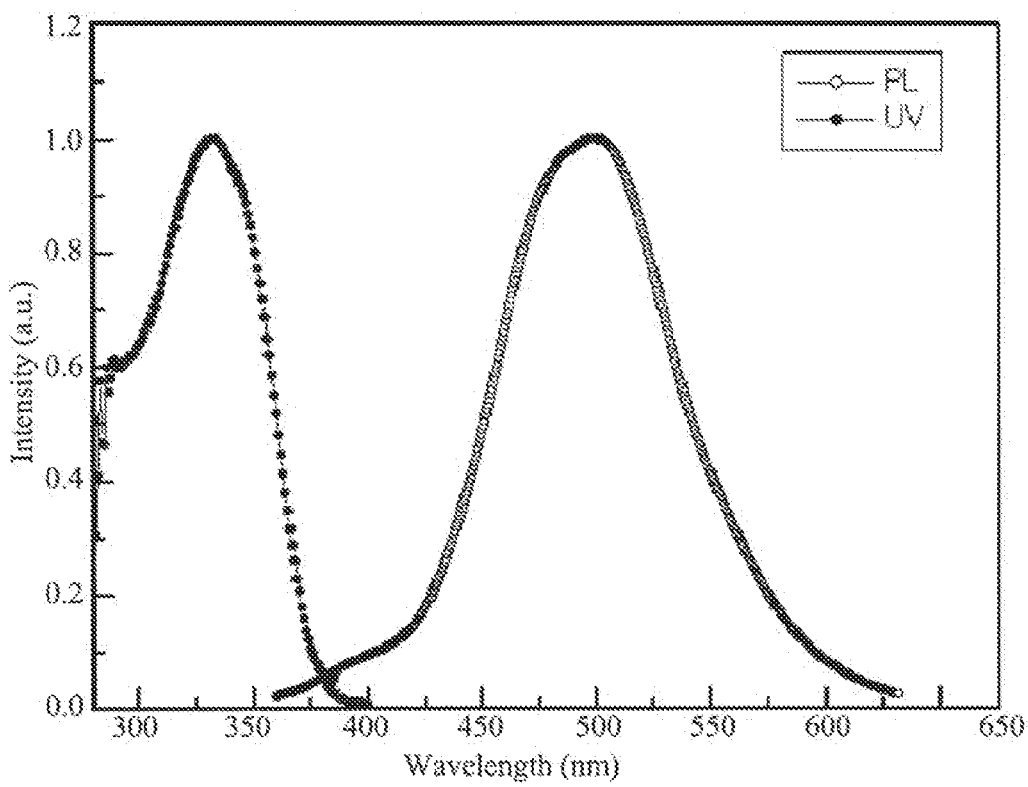
FIG. 12 shows the UV absorption spectrum and photoluminescence spectrum of compound No. 1-35 according to the present invention.

Compound 1-35 showed a glass transition temperature of 183° C. UV Absorption and the photoluminescence spectra are shown in FIG. 12.

Figure 7:
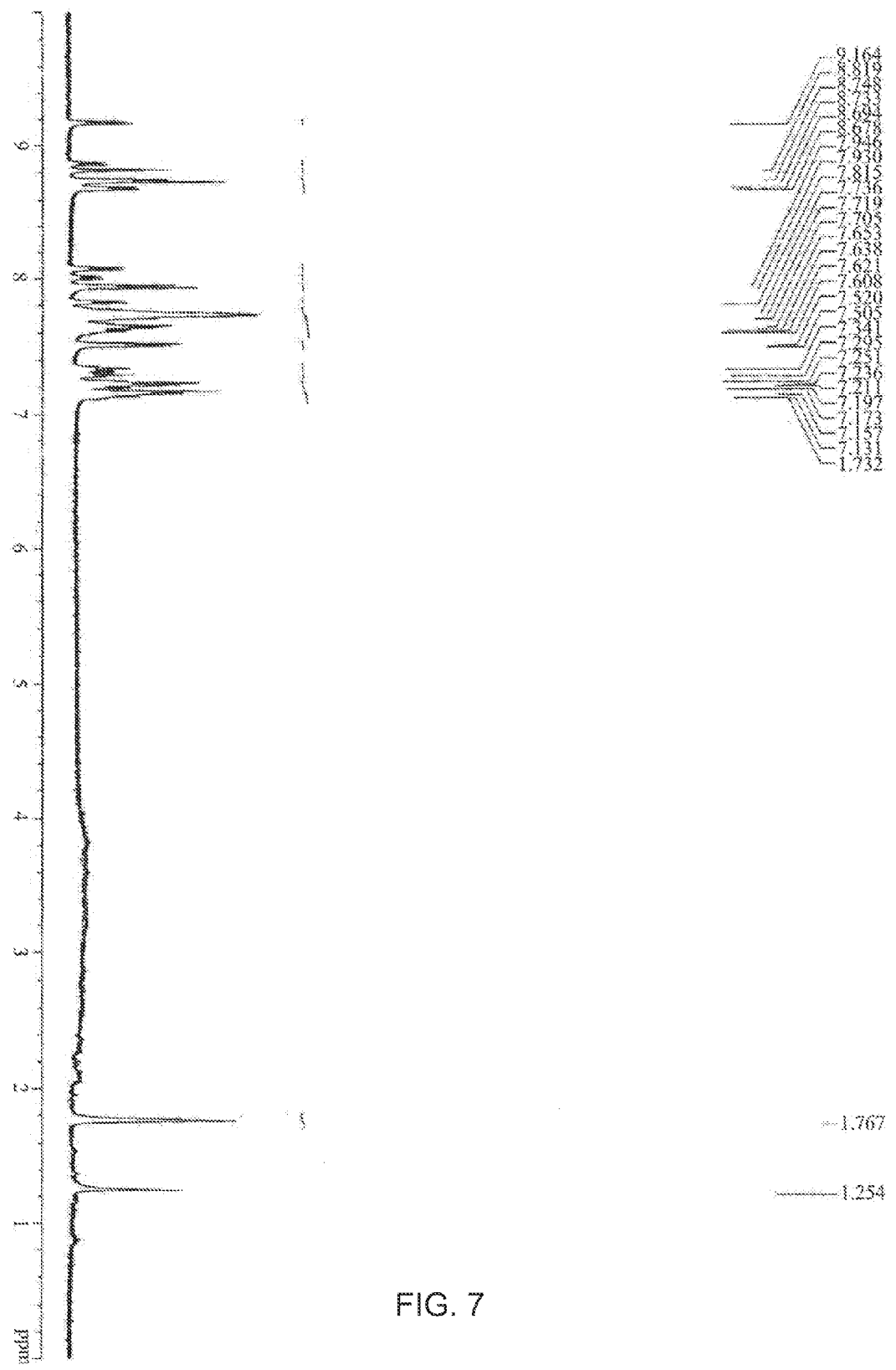
FIG. 7 shows the $^1$H-NMR spectrum of the compound No. 1-35 according to the present invention.

$^1$H-NMR is shown in FIG. 7

$^1$H NMR (CDCl3, δ): 9.16 (d, 1H); 8.82 (d, 1H); 8.74 (s, 1H); 8.73 (d, 2H); 8.69 (d, 2H); 7.94 (d, 2H); 7.81 (d, 1H); 7.73 (d, 4H); 7.71 (d, 1H); 7.70 (m, 6H); 7.65 (m, 6H); 7.52 (d, 3H); 7.34 (m, 3H) ; 7.19 (m, 9H).

Synthesis Example 5

Synthesis of Compound 1-21

A mixture of 5.8 g of 9-Acetyl-3-bromocarbazole and 5.7 g of (4-benzo[d]thiazol-2-yl) phenylboronic acid were stirred together in 30 ml of toluene. To this was added 0.03 g of tetrakis(triphenylphosphine)palladium, 4.2 g of potassium carbonate and 10 ml of aqueous ethanol were added and refluxed under nitrogen for 6 h. The reaction was quenched with water and the toluene layer was removed and passed through a celite column. The organic layers were combined and then evaporated in a rotary evaporator under vacuum to yield 6.7 g of 9-acetyl-3-[(4-benzo [d]thiazol-2-yl) phenyl]-9H-carbazole as a white solid.

The solid (6.7 g) was then taken up for further deprotection using 1.0 g KOH with THF (20 ml), methanol (10 ml) and water (6 ml) at reflux temperature. The reaction mixture was then extracted using ethyl acetate; the organic layer was dried over anhydrous sodium sulfate and evaporated to dryness under vacuum. Subsequent silica gel column chromatography using toluene:hexane (1:2) as eluent, yielded 6.4 g of 3-[(4-benzo[d]thiazol-2-yl) phenyl]-9H-carbazole.

Dissolved the above obtained 3-[(4-benzo[d]imidazol-2-yl) phenyl]-9H-carbazole (6.4 g) in 60 ml of dry N,N'-dimethylformamide under nitrogen. Added 0.9 g of sodium hydride and stirred at room temperature for 1 h. A solution of 2-chloro-4,6-diphenyl-1,3,5-triazine (5.0 g) in dry N,N'-dimethylformamide (20 ml) was then added to the reaction mixture. The reaction was further allowed to stir for another 3 h. The product was precipitated by pouring the reaction mixture into water. The solid thus obtained was then washed with methanol and dried under vacuum to obtain 7.7 g of 9-(4,6-diphenyl-1,3,5-triazin-2-yl)-3-[(4-benzo[d]thiazol-2-yl)phenyl]-9H-carbazole, compound 1-21 (75%).

Compound 1-21 showed a glass transition temperature of 193° C.

Figure 8:
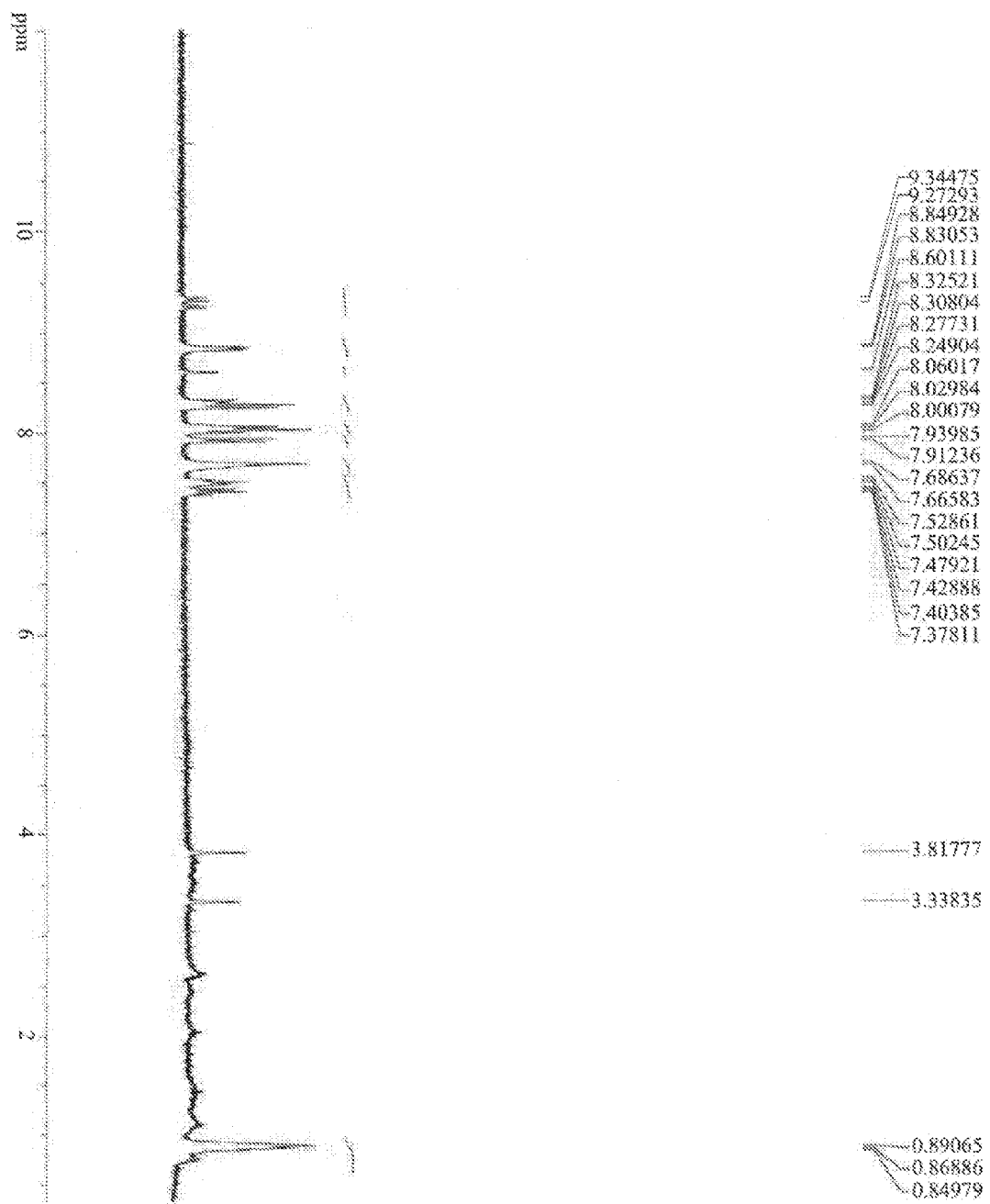
FIG. 8 shows the $^1$H-NMR spectrum of the compound No. 1-21 according to the present invention.

$^1$H-NMR is shown in FIG. 8

$^1$H NMR (CDCl3, δ): 9.34 (m, 2H); 8.85 (m, 3H); 8.60 (s, 1H); 8.30 (m, 4H); 8.03 (m, 5H); 7.94 (d, 2H); 7.68 (m, 4H); 7.43 (m, 414).

Synthesis Example 6

Synthesis of Compound 1-36

Following the above procedure, Suzuki coupling of 3.8 g of 7-acetyl-12-bromo-7H-dibenzo [a,g]carbazole and 2.7 g of (4-benzo[d]thiazol-2-yl) phenylboronic acid were stirred together in 30 ml of toluene. To this was added 0.02 g of tetrakis(triphenylphosphine)palladium, 2.1 g of potassium carbonate and 10 ml of aqueous ethanol were added and refluxed under nitrogen for 6 h. The reaction was quenched with water and the toluene layer was removed and passed through a celite column. The organic layers were combined and then evaporated in a rotary evaporator under vacuum to yield 4.1 g of 7-acetyl-12-[4-benzo[d]thiazol-2-yl) phenyl]-7H-dibenzo[a,g]carbazole as a white solid.

The solid (4.1 g) was then taken up for further deprotection using 0.5 g KOH with THF (20 ml), methanol (10 ml) and water (6 ml) at reflux temperature. The reaction mixture was then extracted using ethyl acetate; the organic layer was dried over anhydrous sodium sulfate and evaporated to dryness under vacuum. Subsequent silica gel column chromatography using toluene:hexane (1:2) as eluent, yielded 3.4 g of 12-[4-benzo[d]thiazol-2-yl) phenyl]-7H-dibenzo[a,g]carbazole.

Dissolved the above obtained 12-[4-benzo[d]thiazol-2-yl) phenyl]-7H-dibenzo[a,g]carbazole (3.4 g) in 50 ml of dry N,N'-dimethylformamide under nitrogen. Added 0.5 g of sodium hydride and stirred at room temperature for 1 h. A solution of 2-chloro-4,6-diphenyl-1,3,5-triazine (2.1 g) in dry N,N'-dimethylformamide (20 ml) was then added to the reaction mixture. The reaction was further allowed to stir for another 3 h. The product was precipitated by pouring the reaction mixture into water. The solid thus obtained was then washed with methanol and dried under vacuum to obtain 3.9 g of 7-(4,6-diphenyl-1,3,5-trazin-2-yl)-12-[4-benzo[d]thiazol-2-yl)phenyl]-7H-diben-zo[a, g]carbazole, compound 1-36 (78%).

Compound 1-36 showed a melting point of 330° C.

Figure 9:
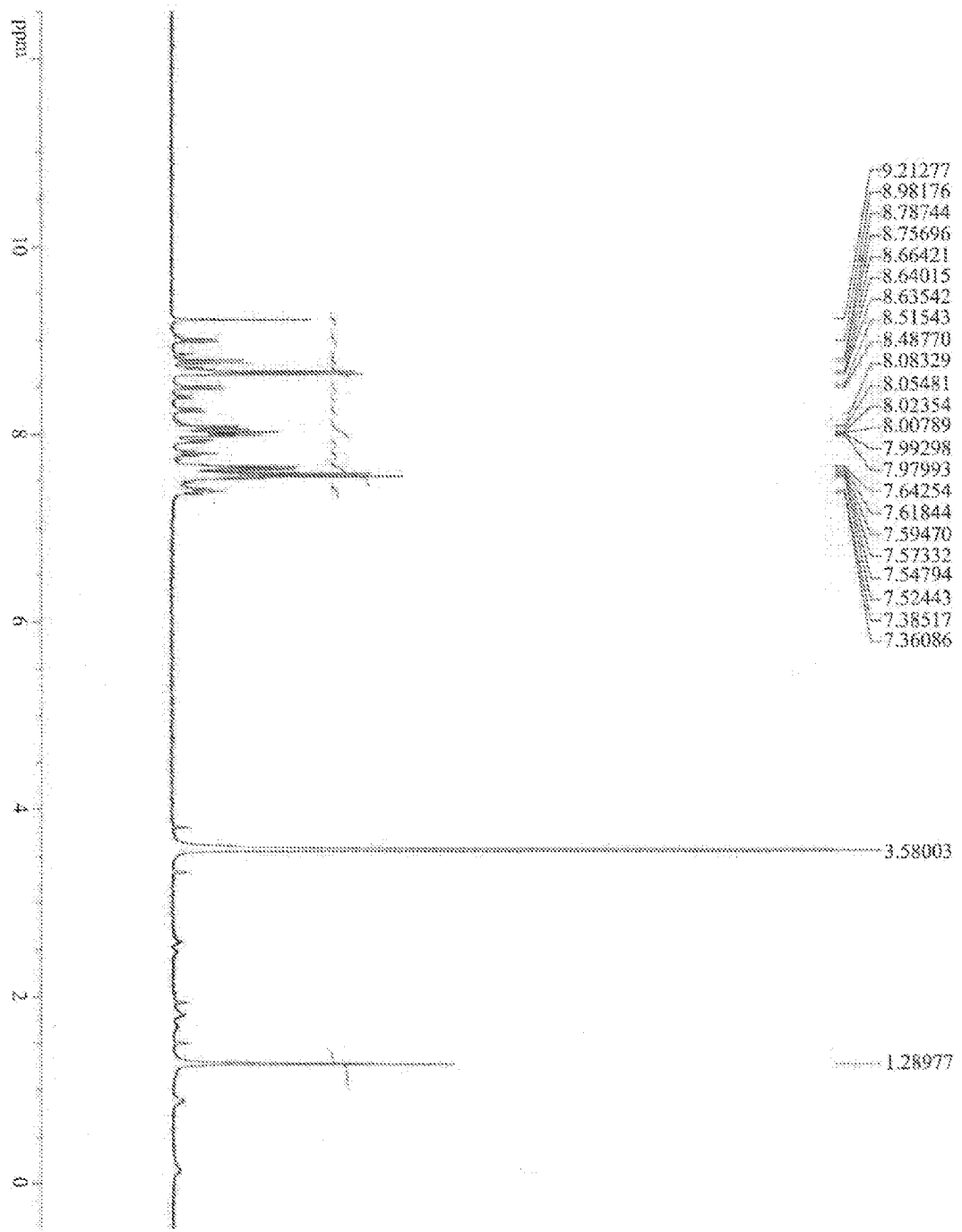
FIG. 9 shows the $^1$H-NMR spectrum of the compound No. 1-36 according to the present invention.

$^1$H-NMR is shown in FIG. 9

$^1$H NMR (CDCl3, δ): 9.21 (s, 1H); 8.99 (d, 1H); 8.78 (d, 1H); 8.66 (m, 5H); 8.52 (d, 1H); 8.08 (m, 6H); 7.64 (m, 11H); 7.39 (t, 2H).

Example 1

Fabrication of Organic EL Device

Prior to use, the substrate was degreased with solvents and cleaned in UV ozone before it was loaded into the evaporation system. The substrate was then transferred into a vacuum deposition chamber for deposition of all other layers on top of the substrate. The following layers were deposited in the following sequence, as shown in FIG. 2, by evaporation from a heated boat under a vacuum of approximately $10^{-6}$ Torr:

a) a hole injecting layer, 30 nm thick, HAT-CN, b) a hole transporting layer, 110 nm thick, N,N'-di-1-naphthyl-N,N'-diphenyl-4,4'-diaminobiphenyl (NPB);

c) a light emitting layer, 30 nm thick, comprising BH doped with 3% BD by volume;

(BH and BD from E-ray optoelectronics Tech Co. Ltd, Taiwan)

e) an electron transporting layer, 15 nm thick, including compound 1-17, doped with Liq;

f) an electron injection layer, 1 nm thick, LiF; and g) a cathode: approximately 150 nm thick, including Al.

Device structure may be denoted as: ITO/HAT-CN (30 nm)/NPB (110 nm)/BH-3% BD (30 nm)/Compound 1-17 (15 nm)/LiF (1 nm)/Al (150 nm).

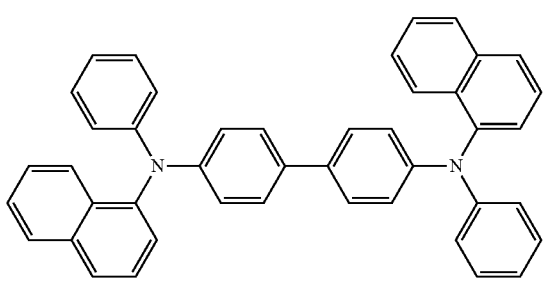

NPB

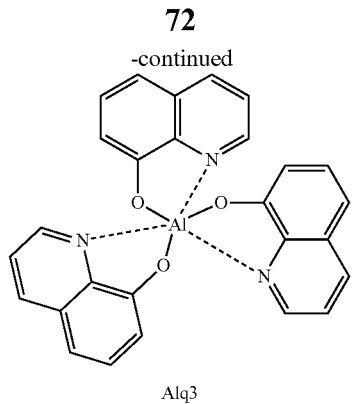

Alq3

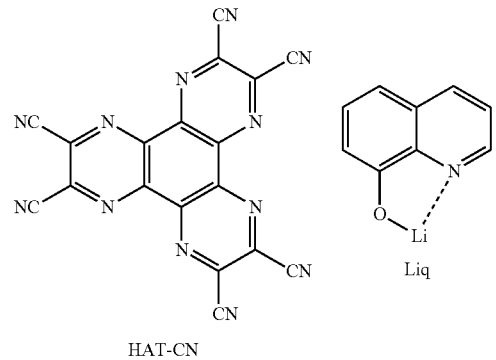

HAT-CN

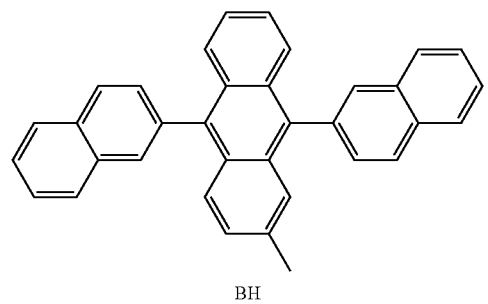

BH

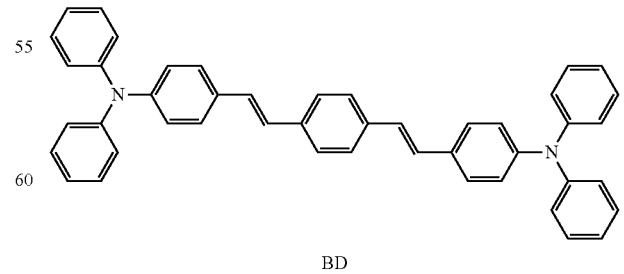

BD

After the deposition of these layers, the device was transferred from the deposition chamber into a dry box for encapsulation, and were subsequently encapsulated using an UV-curable epoxy, and a glass lid containing a moisture getter. The organic EL has an emission area of 3 mm². The organic EL device thus obtained was connected to an outside power source and, upon application of direct current voltage, emission of light with the characteristics shown in Table 2 were confirmed.

The EL characteristics of all the fabricated devices were evaluated using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.) at room temperature.

Operational lifetime (or stability) of the devices were tested at the room temperature and at various initial luminance depending on the color of the emitting layer, by driving a constant current through the devices. The color was reported using Commission Internationale de l'Eclairage (CIE) coordinates.

Example 2 and Example 3 were fabricated using the compounds 1-26 and 1-36, respectively, in the electron transporting layer following the procedure as in Example 1.

Comparative Example 1

Fabrication of Organic EL Device

Organic phosphorescent EL device was fabricated similar to the layer structure as example 1 except that Alq$_3$ was used in place of the compound 1-17, in the electron transporting layer. Device structure may be denoted as: ITO/HAT-CN (30 nm)/NPB (110 nm)/BH-3% BD (30 nm)/Alq$_3$ (15 nm)/LiF (1 nm)/Al (150 nm).

Figure 13:
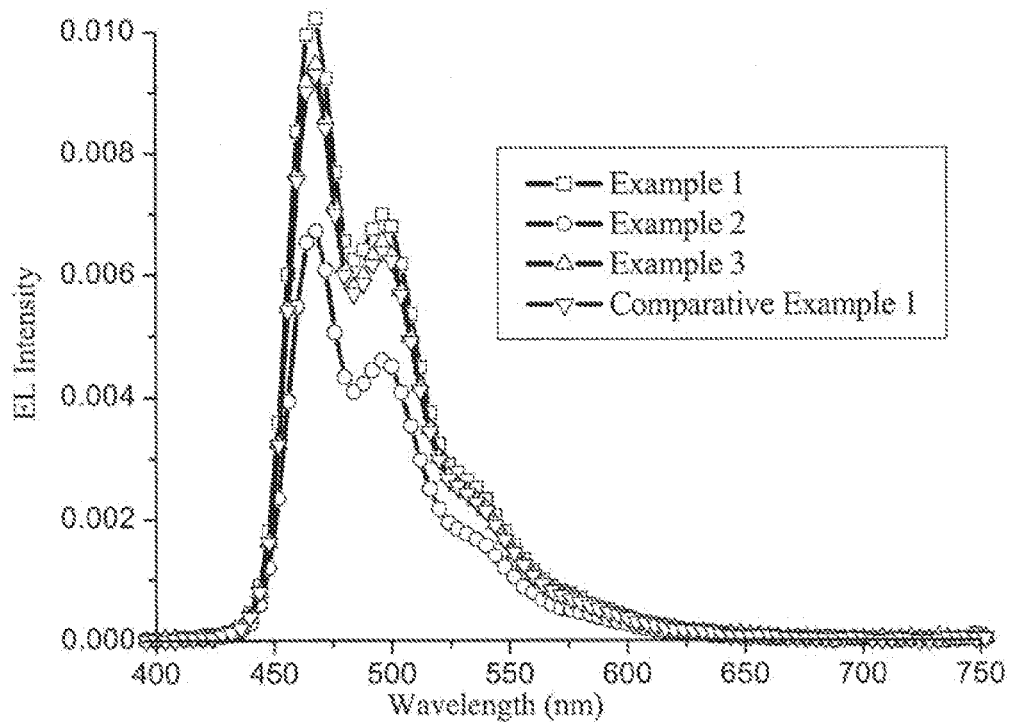
FIG. 13 shows the electroluminescent spectrum of the organic electroluminescent devices of examples 1-3 and comparative example 1 according to the present invention.
Figure 14:
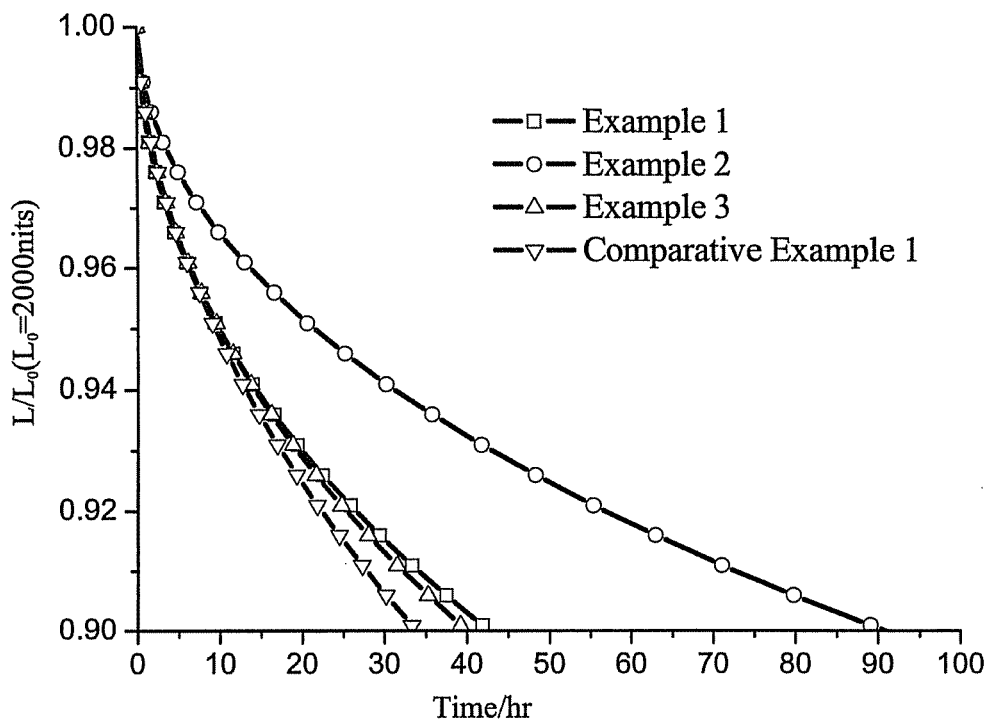
FIG. 14 shows a plot of luminance against time of the organic electroluminescent devices examples 1-3 and comparative example 1 according to the present invention.

The peak wavelength of emitted light, maximum luminance efficiency, driving voltage and power efficiency and the lifetime ($T_{90}$) at an initial luminance of 2000 nits of the organic EL devices fabricated in the examples are shown in Table 2. EL spectra and a comparison of lifetime characteristics of these organic EL devices are shown in FIG. 13 and FIG. 14.

below; PH1 and PH2 is the proprietary phosphorescent host materials from E-ray optoelectronics Tech Co. Ltd, Taiwan. Comparative Example 2 was fabricated following the above structure without the blocking layer.

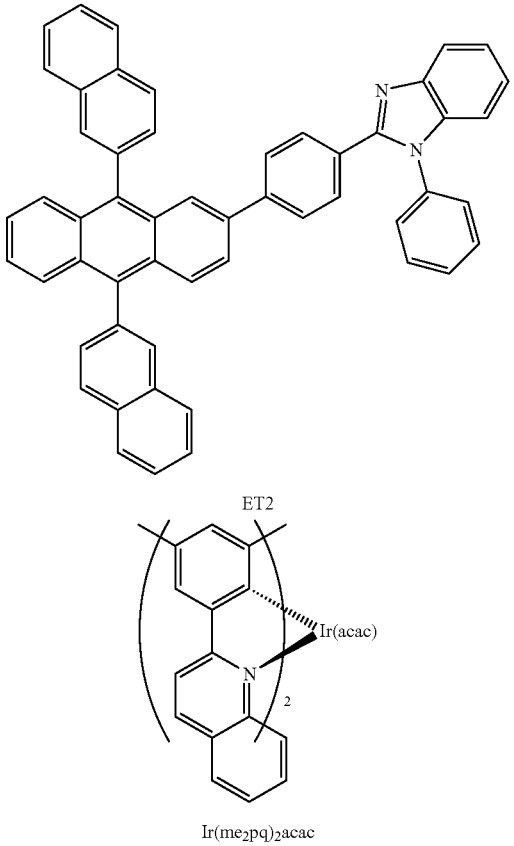

Ir(me$_2$pq)$_2$acac

TABLE 2

| | Compound of Light Emitting Layer | Driving voltage (V) | Peak Wavelength (nm) | luminance efficiency (cd/A) @ 10 mA/cm² | Power efficiency (lm/W) | $T_{90}$ (hr) @2000 nits |
|---|---|---|---|---|---|---|
| Example 1 | Compound 1-17 | 5.34 | 468 | 10.61 | 6.25 | 41.9 |
| Example 2 | Compound 1-26 | 6.26 | 468 | 7.06 | 3.54 | 89.1 |
| Example 3 | Compound 1-36 | 5.79 | 468 | 9.84 | 5.34 | 39.2 |
| Comparative Example 1 | Alq$_3$ | 5.52 | 468 | 9.74 | 5.54 | 33.3 |

Organic EL device for Example 4 was fabricated using the compound 1-17 as the blocking layer (BL) following the device structure.

Figure 15:
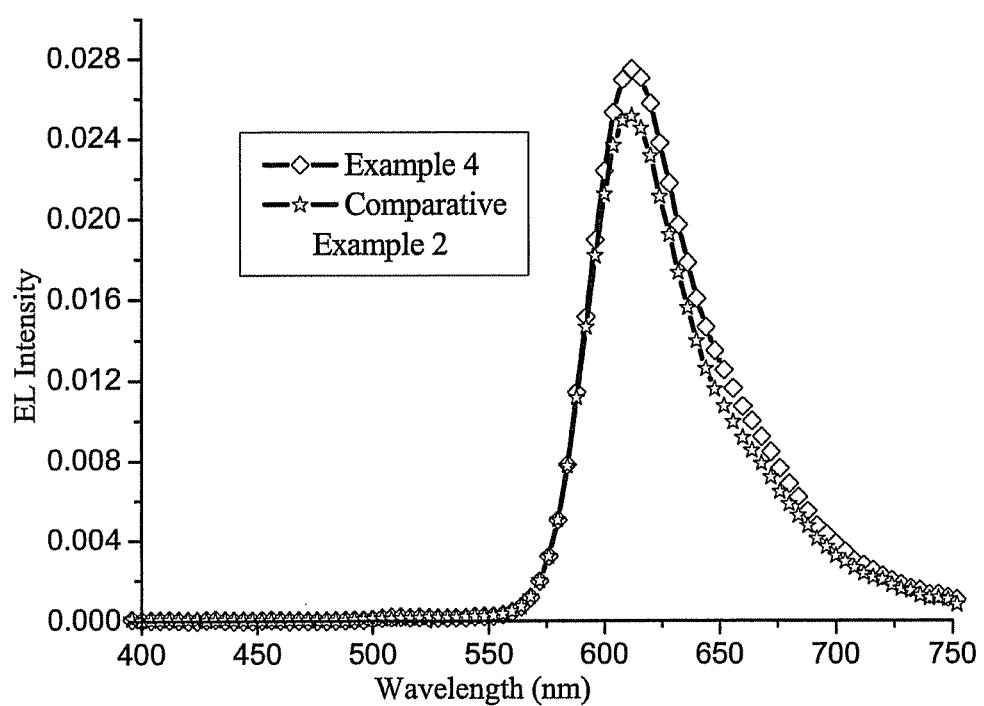
FIG. 15 shows the electroluminescent spectrum of the organic electroluminescent devices example 4 and comparative example 2 according to the present invention.
Figure 16:
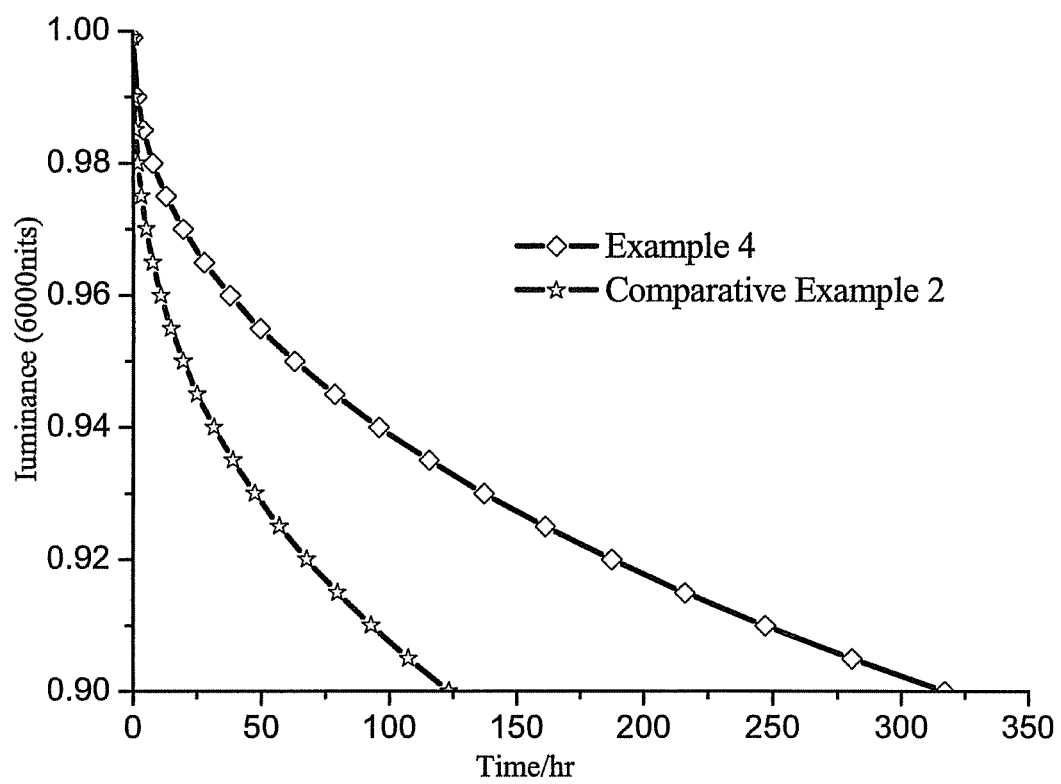
FIG. 16 shows a plot of luminance against time of the organic electroluminescent devices example 4 and comparative example 2 according to the present invention.

ITO/HAT-CN (20 nm)/NPB (160 nm)/3% PRD–PH1+PH2 (30 nm)/BL (10 nm)/50% ET2-50% Liq (30nm)/LiF (1 nm)/Al (150 nm),

Where ET2 is the electron transport material and PRD is the phosphorescent red dopant, whose structures are shown The peak wavelength of emitted light, maximum luminance efficiency, driving voltage and power efficiency and the lifetime ($T_{90}$) at an initial luminance of 6000 nits of the organic EL devices fabricated in the examples are shown in Table 3. EL spectra and a comparison of lifetime characteristics of these organic EL devices are shown in FIG. 15 and FIG. 16.

TABLE 3

| | Compound in the Blocking layer | Driving voltage (V) | Peak Wavelength (nm) | luminance efficiency (cd/A) @ 1000 nits | Power efficiency (lm/W) | $T_{90}$ (hr) @6000 nits |
|---|---|---|---|---|---|---|
| Example 4 | Compound 1-17 | 3.10 | 612 | 33.19 | 31.40 | 316.9 |
| Comparative Example 2 | — | 3.36 | 612 | 31.02 | 31.01 | 159.7 |

The invention shall not be limited by the above described embodiment, method and examples, but by all embodiments and methods within the scope and spirit of the invention as claimed.

INDUSTRIAL APPLICABILITY

As described above in detail, the organic EL device in which the material for the EL device of the present invention is used is extremely practical due to its low driving voltage and adequately long lifetime.
Therefore, the organic EL device of this invention is applicable to flat panel displays, mobile phone displays, light sources utilizing the characteristics of planar light emitters, sign-boards and has a high technical value.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:
1. A compound of formula (I) for an organic electroluminescent device:

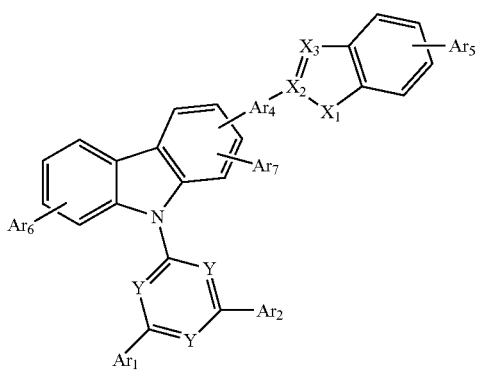

(I)

wherein $X_1$ represents a heteroatom selected from the group consisting of O and S, $X_3$ represents N, Y represents N, and $X_2$ represents C;

$Ar_1$, and $Ar_2$ each independently represent $C_{1-16}$ alkyl substituted, $C_{6-18}$ aryl substituted, unsubstituted $C_{6-14}$ aromatic hydrocarbon group; or $C_{3-15}$ heterocyclic aromatic hydrocarbon group containing heteroatoms selected from the group consisting of N, O, and S, $Ar_4$ represents unsubstituted $C_{6-14}$ aromatic hydrocarbon group, and $Ar_4$ is attached to $X_2$; and $Ar_5$, $Ar_6$, and $Ar_7$ each represent H, $C_{1-16}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

2. A blocking layer for an organic electroluminescent device, comprising:
a compound of formula (I)

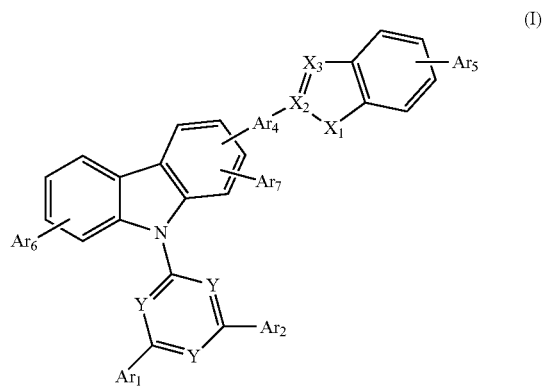

(I)

wherein $X_1$ represents a heteroatom selected from the group consisting of O and S, $X_3$ represents N, Y represents N, and $X_2$ represents C;

$Ar_1$, and $Ar_2$ each independently represent $C_{1-16}$ alkyl substituted, $C_{6-18}$ aryl substituted, unsubstituted $C_{6-14}$ aromatic hydrocarbon group; or $C_{3-15}$ heterocyclic aromatic hydrocarbon group containing heteroatoms selected from the group consisting of N, O, and S, $Ar_4$ represents unsubstituted $C_{6-14}$ aromatic hydrocarbon group, and $Ar_4$ is attached to $X_2$; and $Ar_5$, $Ar_6$, and $Ar_7$ each represent H, $C_{1-16}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

3. An organic electroluminescent device, comprising an electron transporting layer having a compound of formula (I) and an electrically injecting dopant

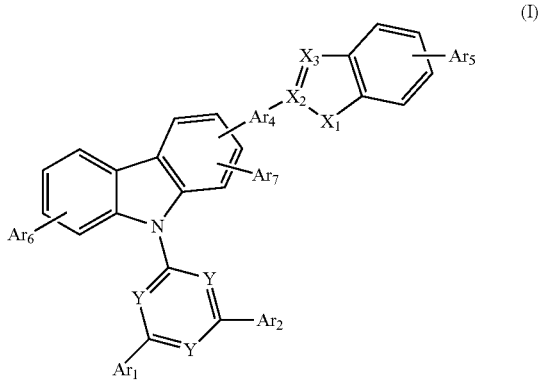

wherein $X_1$ represents a heteroatom selected from the group consisting of O and S, $X_3$ represents N, Y represents N, and $X_2$ represents C;

$Ar_1$, and $Ar_4$ each independently represent $C_{1-16}$ alkyl substituted, $C_{6-18}$ aryl substituted, unsubstituted $C_{6-14}$ aromatic hydrocarbon group; or $C_{3-15}$ heterocyclic aromatic hydrocarbon group containing heteroatoms selected from the group consisting of N, O, and S $Ar_4$ represents unsubstituted $C_{6-14}$ aromatic hydrocarbon group and $Ar_4$ is attached to $X_2$; and $Ar_5$, $Ar_6$, and $Ar_7$ each represent H, $C_{6-18}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

4. An organic electroluminescent device, comprising
a hole blocking layer; and
an electron blocking layer,
wherein one of the hole blocking layer and the electron blocking layer comprises a compound of a formula selected from formula (I)

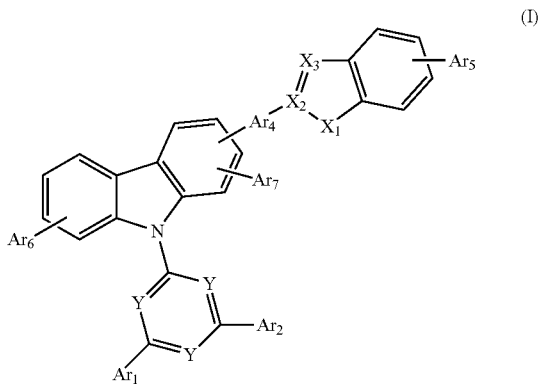

wherein $X_1$ represents a heteroatom selected from the group consisting of O and S, $X_3$ represents N, Y represents N, and $X_2$ represents C;

$Ar_1$, and $Ar_2$ each independently represent $C_{1-16}$ alkyl substituted, $C_{6-18}$ aryl substituted, unsubstituted $C_{6-14}$ aromatic hydrocarbon group; or $C_{3-15}$ heterocyclic aromatic hydrocarbon group containing heteroatoms selected from the group consisting of N, O, and S $Ar_4$ represents unsubstituted $C_{6-14}$ aromatic hydrocarbon group, and $Ar_4$ is attached to $X_2$; and $Ar_5$, $Ar_6$, and $Ar_7$ each represent H, $C_{1-16}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

5. A method for forming an organic electroluminescent device, comprising the steps of:
forming a hole injection layer on a substrate;
forming a hole transporting layer on the hole injecting layer;
forming a light emitting layer on the hole transporting layer;
forming an electron transporting layer on the light emitting layer having an electrically injecting dopant and a compound of formula (I)

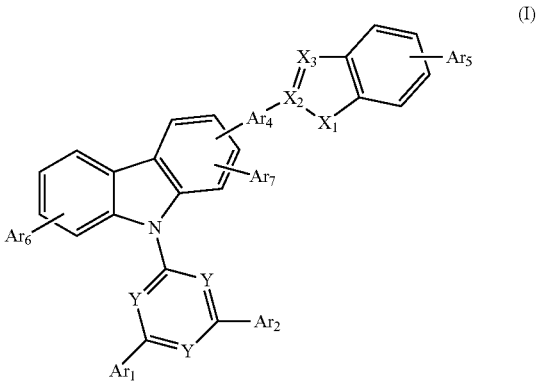

wherein $X_1$ represents a heteroatom selected from the group consisting of O and S, $X_3$ represents N, Y represents N, and $X_2$ represents C;

$Ar_1$ and $Ar_2$ each independently represent $C_{1-16}$ alkyl substituted, $C_{6-18}$ aryl substituted, unsubstituted $C_{6-14}$ aromatic hydrocarbon group; or $C_{3-15}$ heterocyclic aromatic hydrocarbon group containing heteroatoms selected from the group consisting of N, O, and S, $Ar_4$ represents unsubstituted $C_{6-14}$ aromatic hydrocarbon group, and $Ar_4$ is attached to $X_2$; and $Ar_5$, $Ar_6$, and $Ar_7$ each represent H, $C_{1-16}$ alkyl, $C_{6-18}$ aryl substituted, or unsubstituted $C_{6-14}$ aromatic hydrocarbon group; or a $C_{3-15}$ heterocyclic aromatic hydrocarbon group containing heteroatoms selected from the group consisting of N, O, and S; or $C_{1-16}$ alkyl, $C_{6-18}$ aryl substituted, or unsubstituted $C_{6-24}$ condensed polycyclic aromatic group, and may form a part of the delocalized ring.

6. The method of claim 5, wherein the electrically injecting dopant is one of Liq, CsF, $CS_2CO_3$, $MoO_3$, $W_2O_3$.

7. The method of claim 5, wherein the electrically injecting dopant is in a range from 25 wt % to 75 wt % based on total weight of the electron transporting layer.

* * * * *